US005646250A

United States Patent [19]
Suzuki

[11] Patent Number: 5,646,250
[45] Date of Patent: Jul. 8, 1997

[54] CADHERIN POLYPEPTIDES

[75] Inventor: Shintaro Suzuki, Torrance, Calif.

[73] Assignee: Doheny Eye Institute, Los Angeles, Calif.

[21] Appl. No.: 332,638

[22] Filed: Nov. 1, 1994

Related U.S. Application Data

[63] Continuation of Ser. No. 49,460, Apr. 19, 1993, abandoned, which is a continuation-in-part of Ser. No. 872,643, Apr. 17, 1992, abandoned.

[51] Int. Cl.$^6$ .................. C07K 14/435; C12N 15/12
[52] U.S. Cl. .................. 530/350; 530/360; 530/395; 435/69.1
[58] Field of Search .................. 530/350, 395, 530/300; 435/69.1

[56] References Cited

FOREIGN PATENT DOCUMENTS

WO/91/04745  4/1991  WIPO.
WO/92/08731  5/1992  WIPO.

OTHER PUBLICATIONS

Sambrook et al., "Molecular Cloning, A Lab. Manual", pp. 16.2 to 16.31, Cold Spring Harbor Lab. Press, 1989.
Ausubel et al., Eds., *Current Protocols in Molecular Biology*, Sections 6.1.1 to 6.1.4. and 6.2.1 to 6.2.3, John Wiley and Sons Ltd., New York (1987).
Behrens et al., "Dissecting Tumor Cell Invasion: Epithelial Cells Acquire Invasive Properties after the Loss of Uvomorulin–Mediated Cell–Cell Adhesion", *J. Cell. Biol.*, 108: 2435–2447 (Jun. 1989).
Blaschuk et al., "Identification of a Cadherin Cell Adhesion Recognition Sequence", *Devel. Biol.*, 139:227–229 (1990).
Collins et al., "Cloning and Sequence Analysis of Desmosomal Glycproteins 2 and 3 (Desmocollins): Cadherin–like Desmosomal Adhesion Molecules with Heterogenous Cytoplasmic Domains" *J. Cell. Biol.*, 113(2): 381–391 (Apr. 1991).
Detrick et al., "The Effects of N–Cadherin Misexpression on Morphogenesis in Xenopus Embryos", *Neuron*, 4: 493–506 (Apr. 1990).
Donalies et al., "Expression of M–cadherin, A Member of the Cadherin Multigene Family, Correlates with Differentiation of Skeletal Muscle Cells", *Proc. Natl. Acad. Sci. (USA).*, 88:8024–8028 (1991).
Franke et al., "Immunolocalization of Plakoglobin in Endothelial Junctions: Identification as a Special Type of *Zonulae adhaerentes*", *Biol. of the Cell*, 59:205–218 (1987).
Franke et al., "Molecular Cloning and Amino Acid Sequence of Human Plakoglobin, the Common Junctional Plaque Protein", *Proc. Natl. Acad. Sci. (USA)*, 86:4027–4031 (1989).
Frixen et al., "E–Cadherin–Mediated Cell–Cell Adhesion Prevents Invasiveness of Human Carcinoma Cells", *J. Cell. Biol.*, 113(1): 173–185 (Apr. 1991).

Fujimori et al., "Disruption of Epithelial Cell–Cell Adhesion by Exogenous Expression of a Mutated Nonfunctional N–Cadherin", *Molecular Biology of the Cell*, 4:37–47 (1993).
Furie et al., "Migration of Neutrophilis Across Endothelial Monolayers is Stimulated by Treatment of the Monolayers with Interleukin–1 or Tumor Necrosis Factor–$\alpha$", *J. Immunol.*, 143:3309–3317 (1989).
Furie et al., "E–Selectin (Endothelial–Leukocyte Adhesion Molecule–1) is Not Required for the Migration of Neutrophils Across IL–1 Stimulated Endothelium In Vitro", *J. Immunol.*, 148:2395–2484 (1992).
Furie et al., "Monoclonal Antibodies to Leukocyte Integrins CD1a/CD18 and CD11b/CD18 or Intercellular Adhesion Molecule–1 Inhibit Chemoattractant–Stimulated Neutrophil Transendothelial Migration In Vitro", *Blood*, 78:2089–2097 (1991).
Gallin et al., "Sequence Analysis of a cDNA Encoding the Liver Cell Adhesion Molecule, L–CAM", *Proc. Natl. Acad. Sci. (USA)*, 84:2808–2812 (1987).
Geiger et al., "Broad Spectrum Pan–Cadherin antibodies, Reactive with the C–Terminal 24 Amino Acid Residues of N–Cadherin", *J. Cell Science*, 97:607–614 (1990).
Hatta et al., "Cloning and Expression of cDNA Encoding a Neural Calcium–Dependent Cell Adhesion Molecule:Its Identity in the Cadherin Gene family", *J. Cell Biol.*, 106:873–881 (1988).
Heimark et al., "Identification of a $Ca^{2+}$–dependent Cell–Cell Adhesion Molecule in Endothelial Cells", *J. Cell Biol.*, 110:1745–1756 (1990).
Herrenkencht et al., "The Uvomorulin–Anchorage Protein $\alpha$ Catenin is a Vinculin Homologue", *Proc. Natl. Acad. Sci. (USA)*, 88:9156–9160 (1991).
Inuzuka et al., "R–Cadherin: A Novel $Ca^{2+}$–Dependent Cell–Cell Adhesion Molecule Expressed in the Retina", *Neuron.*, 7:69–79 (1991).
Kitner et al., "Regulation of Embryonic Cell Adhesion by the Cadherin Cytoplasmic Dosmain", *Cell*, 69:225–236 (1992).
Klambt et al., "The Drosophila Melanogaster 1(2)gl Gene Encodes a Protein Homologous to the Cadherin Cell–Adhesion Molecule Family", *Devel. Biol.*, 133: 425–436 (1989).

(List continued on next page.)

*Primary Examiner*—Stephen Walsh
*Assistant Examiner*—Sally P. Teng
*Attorney, Agent, or Firm*—Marshall, O'Toole, Gerstein, Murray & Borun

[57] ABSTRACT

DNA sequences encoding novel cadherins, desginated cadherins-4 through -12, are disclosed along with methods and materials for the recombinant production of the same. Antibody substances specific for the novel cadherins and cadherin peptides are disclosed as useful for modulating the natural binding and/or regulatory activities of the cadherins.

3 Claims, 1 Drawing Sheet

OTHER PUBLICATIONS

Koch et al., "Identification of Desmoglein, a Consititutive Desmosomal Glycoprotein, as a Member of the Cadherin Family of Cell Adhesion Molecules", *Eur. J. Cell Biol.*, 53:1–12 (1990).

Liaw et al., "Identification and Cloning of Two Species of Cadherins in Bovine Endothelial Cells", *EMBO J.*, 9:2701–2708 (1990).

Mahoney et al., "The fat Tumor Suppressor Gene in Drosophilia Encodes a Novel Member of the Cadherin Gene Superfamily", *Cell*, 67:853–868 (1991).

Maniatis et al., Eds., *Molecular Cloning:A Laboratory Manual*, "Guanidinium/Cesium Chloride Method", p. 196, Cold Spring Harbor Laboratory, Cold Spring Harbor, New York (1982).

Matsunaga et al., "Guidance of Optic Nerve Fibers by N–Cadherin Adhesion Molecules", *Nature*, 334:62–64 (1988).

McCrea et al., "A Homolog of the *armadillo*Proein in *Drosophila* (Plakoglobin) Associated with E–Cadherin", *Science*, 254:1359–1361 (1991).

Nagafuchi et al., "Tranformation of Cell Adhesion Properties by Exogenously Introduced E–Cadherin cDNA", *Nature*, 329:341–343 (1987).

Nagafuchi et al., "the 102 kd Cadeherin–Asociated Protein: Similarity to Vinculin and Posttranscriptional Regulation of Expression", *Cell*, 65:849–857 (1991).

Napolitano et al., "Molecular Cloning and Characterization of B–Cadherin, a Novel Chick Cadherin", *J. Cell Biol.*, 113:893–905 (1991).

Nelson et al., "Identification of a Membrane–Cytoskeletal Complex Containing the Cell Adhesion Molecule Uvomorulin (E–Cadherin) Ankyrin, and Fodrin in Madin–Darby Canine Kidney Epithlelial Cells", *J. Cell Biol.*, 110:349–357 (1990).

Nose et al., "Isolation of Placental Cadherin cDNA:Identification of a Novel Gene Family of Cell–Cell Adhesion Molecules", *EMBO J.*, 6:3655–3661 (1987).

Ozawa et al., "The Cytoplasmic Domain of the Cell Adhesion Molecule Uvomorulin Associates eith Three Independent Proteins Structurally Related in Different Species", *EMBO J.*, 8:1711–1717 (1989).

Peifer et al., "The Vertebrate Adhesive Junction Proteins β–catenin and Plakoglobin and the *Drosophila* Segment Polarity Gene *armadillo* Form a Multigene Family with Similar Properties Properties", *J. Cell Biol.*, 118:681–691 (1992).

Ranscht et al., "T–Cadherin, a Novel Cadherin Cell Adhesion Molecule in the Nervous System Lacks the Conserved Cytoplasmic Region", *Neuron*, 7:391–402 (1991).

Ringwald et al., "The Structure of Cell Adhesion Molecule Uvomorulin, Insights into the Molecular Mechanism of $Ca^{2+}$–Dependent Cell Adhesion", *EMBO J.*, 6;3647–3653 (1987).

Sacristan et al., "Evidence for the Coexistance of Two T–cadherin Forms in the Develpoing Chicken Nervous System", *J. Cell Biol.*, 111, Abstract 158a (1990).

Saiki et al., "Primer–Directed Enzymatic Amplification of DNA with a Thermostable DNA Polymerase", *Science*, 239:487–491 (1988).

Shimoyama et al., "Cadherin Dysfunction in a Human Cancer Cell Line:Possible Involvement of Loss of α–Catenin Expression in Reduced Cell–Cell Adhesiveness[1]", *Cancer Res.*, 52:5770–5774 (1992).

Suzuki et al., "Diversity of the Cadherin Family: Evidence for Eight New Cadherins in Nervous Tissue", *Cell Regulation*, 2:261–270 (1991).

Suzuki et al., "Evidence for Cadherin Superfamily", *J. Cell Biol.*, 115, Abstract 72a (1991).

Suzuki et al., "Evidence for Cadherin Superfamily", *Cell Struc. Func.*, 16:605 (1991).

Takeichi, "Cadherin Cell Adhesion Receptors as a Morphogenetic Regulator", *Science*, 251:1451–1455 (1991).

Takeichi, "Cadherins:A Molecular Family Important in Selective Cell–Cell Adhesion", *Annu. Rev. Biochem.*, 59:237–252 (1990).

Tanihara et al., "Molecular Cloning of Novel Cadherins from Neural Retina", *Invest. Opthalmol. Vis. Sci.*, 32:1013 (1991).

Thomas, "Hybridization of Denatured RNA and Small DNA Fragments Transferred to nitrocellulose", *Proc. Natl. Acad. Sci.* (USA), 77:5201–5202 (1980).

Vleminckx et al., "Genetic Manipulation of E–Cadherin Expression by Epithelial Tumor Cells Reveals an Invasion Suppressor Role", *Cell*, 66: 107–119 (Jul. 1191).

Yoshida–Noro et al., "Molecular Nature of the Calcium–Dependent Cell–Cell Adhesion System in Mouse Teratocarcinoma and Embryonic Cells Studied with a Monoclonal Antibody", *Devel. Biol.*, 101:19–27 (1984).

CADHERIN POLYPEPTIDES

This is a Rule 62 file wrapper continuation of U.S. patent application Ser. No. 08/049,460, filed Apr. 19, 1993, now abandoned, which in turn is a continuation-in-part of U.S. patent application Ser. No. 07/872,643, filed Apr. 17, 1992, now abandoned.

This invention was made with government support under grant No. 5 R01 HL45335-04 awarded by the Heart, Lung and Blood Institute of the National Institutes of Health and grant No. 7 R01 CA42571 awarded by the National Cancer Institute of the National Institutes of Health. The government has certain rights in the invention.

FIELD OF THE INVENTION

The present invention relates, in general, to materials and methods relevant to cell-cell adhesion. More particularly, the invention relates to novel $Ca^{2+}$-dependent cell adhesion proteins, referred to as cadherins, and to polynucleotide sequences encoding the cadherins. The invention also relates to methods for inhibiting binding of the cadherins to their natural ligands/antiligands.

BACKGROUND

In vivo, cell-cell adhesion plays an important role in a wide range of events including morphogenesis and organ formation, leukocyte extravasation, tumor metastasis and invasion, and the formation of cell junctions. Additionally, cell-cell adhesion is crucial for the maintenance of tissue integrity, e.g., of the intestinal epithelial barrier, of the blood brain barrier and of cardiac muscle.

Intercellular adhesion is mediated by specific cell adhesion molecules. Cell adhesion molecules have been classified into at least three superfamilies including the immunoglobulin (Ig) superfamily, the integrin superfamily and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain that determines binding specificity (the N-terminal 113 amino acids appear to be directly involved in binding), a hydrophobic membrane-spanning domain and a C-terminal cytoplasmic domain (highly conserved among the members of the superfamily) that interacts with the cytoskeleton through eatenins and other cytoskeleton-associated proteins. Some cadherins lack a cytoplasmic domain, however, and appear to function in cell-cell adhesion by a different mechanism than cadherins that do have a cytoplasmic domain. The cytoplasmic domain is required for the binding function of the extracellular domain in cadherins that do have a cytoplasmic domain. Binding between members of the cadherin family expressed on different cells is mainly homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59:237–252 (1990) and Takeichi, *Science*, 251, 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvment in $Ca^{2+}$ dependent cell adhesion and by their unique immunological characteristics and tissue localization. With the later immunological identification of N-cadherin, which was found to have a different tissue distribution from E-cadherin, it became apparent that a new family of $Ca^{2+}$-dependent cell-cell adhesion molecules had been discovered.

The molecular cloning of the genes encoding mouse E- [see Nagafuchi et al., *Nature*, 329: 341–343 (1987)], chicken N-[Hatta et al., *J. Cell Biol.*, 106: 873–881 (1988)], and mouse P-[Nose et al., *EMBO J.* 6: 3655–3661 (1987)] cadherins provided structural evidence that the cadherins comprised a family of cell adhesion molecules. Cloning of chicken L-CAM [Gallin et al., *Proc. Natl. Acad. Sci. USA*, 84: 2808–2812 (1987)] and mouse uvomorulin [Ringwald et al., *EMBO J.*, 6: 3647–3653 (1987)] revealed that they were identical to E-cadherin. Comparisons of the amino acid sequences of E-, N-, and P-cadherins showed a level of amino acid similarity of about 45%–58% among the three subclasses. Liaw et al., *EMBO J.*, 9: 2701–2708 (1990) describes the use of PCR with degenerate oligonucleotides based on one conserved region of E-, N- and P-cadherins to isolate N- and P-cadherin from a bovine microvascular endothelial cell cDNA. The Liaw et al., supra, results implied that there were only E-, N-, and P-cadherins because no new cadherins were identified. Also in 1990, it was reported in Heimark et al., *J. Cell Biol.*, 110: 1745–1756 (1990) that an antibody generated to bovine aortic endothelial cells recognized an intercellular junctional molecule designated V-cadherin which had a similar molecular weight to known cadherins and was able to inhibit $Ca^{2+}$-dependent cell endothelial cell adhesion. The article did not disclose any sequence information for the protein recognized by the antibody.

No further cadherin genes were described until the identification of eight of the novel cadherins claimed herein was reported in Suzuki et at., *Cell Regulation*, 2: 261–270 (1991). Subsequently, several other cadherins were described including chicken R-cadherin [Inuzuka et al., *Neuron*, 7: 69–79 (1991)], mouse M-cadherin [Donalies et at., *Proc. Natl. Acad. Sci. USA*, 88: 8024–8028 (1991)], chicken B-cadherin [Napolitano et al., *J. Cell. Biol.*, 113: 893–905 (1991)], and T-cadherin [chicken in Ranscht et al., *Neuron*, 7: 391–402 (1991) and chicken and human in Patent Cooperation Treaty (PCT) International Publication No. WO 92/08731 published on May 29, 1992].

The determination of the tissue expression of the various cadherins reveals that each subclass of cadherins has a unique tissue distribution pattern. For example, E-cadherin is found in epithelial tissues while N-cadherin is found in nonepithelial tissues such as neural and muscle tissue. The unique expression pattern of the different cadherins is particularly significant when the role each subclass of cadherins may play in vivo in normal events (e.g., the maintenance of the intestinal epithelial barrier) and in abnormal events (e.g., tumor metastatis or inflammation) is considered. Supression of cadherin function has been implicated in the progression of various cancers. See Shimoyama et al., *Cancer Res.*, 52: 5770–5774 (1992). Different subclasses or combinations of subclasses of cadherins are likely to be responsible for different cell-cell adhesion events in which therapeutic detection and/or intervention may be desirable. Studies have also suggested that cadherins may have some regulatory activity in addition to adhesive activity. Matsunaga et al., *Nature*, 334, 62–64 (1988) reports that N-cadherin has neurite outgrowth promoting activity and Mahoney et al., *Cell*, 67, 853–868 (1991) reports that the Drosophila fat tumor supressor gene, another member of the cadherin superfamily, appear to regulate cell growth. Expression of the cytoplasmic domain of N-cadherin without its extracellular domain has been shown in Kintner et al., *Cell*, 69:

229-236 (1992) to disrupt embryonic cell adhesion and in Fugimori et al., Mol. Biol. Cell, 4: 37-47 (1993) to disrupt epithial cell adhesion. Thus, therapeutic intervention in the regulatory activities of cadherins expressed in specific tissues may also be desirable.

There thus continues to exist a need in the art for the identification and characterization of additional cadherins participating in cell-cell adhesion and/or regulatory events. Moreover, to the extent that cadherins might form the basis for the development of therapeutic and diagnostic agents, it is essential that the genes encoding the proteins be cloned. Information about the DNA sequences and amino acid sequences encoding the cadherins would provide for the large scale production of the proteins and for the identification of the cells/tissues naturally producing the proteins, and would permit the preparation of antibody substances or other novel binding molecules specifically reactive with the cadherins that may be useful in modulating the natural ligand/antiligand binding reactions in which the cadherins are involved.

SUMMARY OF THE INVENTION

The present invention provides materials and methods that are relevant to cell-cell adhesion. In one of its aspects, the present invention provides purified and isolated polynucleotide sequences (e.g., DNA and RNA, both sense and antisense strands) encoding novel cadherins, cadherin-4 through -12. Preferred polynucleotide sequences of the invention include genomic and cDNA sequences as well as wholly or partially synthesized DNA sequences, and biological replicas thereof (i.e., copies of purified and isolated DNA sequences made in vivo or in vitro using biological reagents). Biologically active vectors comprising the polynucleotide sequences are also contemplated.

The scientific value of the information contributed through the disclosures of the DNA and amino acid sequences of the present invention is manifest. For example, knowledge of the sequence of a cDNA encoding a cadherin makes possible the isolation by DNA/DNA hybridization of genomic DNA sequences that encode the protein and that specify cadherin-specific expression regulating sequences such as promoters, enhancers and the like. DNA/DNA hybridization procedures utilizing the DNA sequences of the present invention also allow the isolation of DNAs encoding heterologous species proteins homologous to the rat and human cadherins specifically illustrated herein.

According to another aspect of the invention, host cells, especially eucaryotic and procaryotic cells, are stably transformed or transfected with the polynucleotide sequences of the invention in a manner allowing the expression of cadherin polypeptides in the cells. Host cells expressing cadherin polypeptide products, when grown in a suitable culture medium, are particularly useful for the large scale production of cadherin polypeptides, fragments and variants; thereby enabling the isolation of the desired polypeptide products from the cells or from the medium in which the cells are grown.

The novel cadherin proteins, fragments and variants of the invention may be obtained as isolates from natural tissue sources, but are preferably produced by recombinant procedures involving the host cells of the invention. The products may be obtained in fully or partially glycosylated, partially or wholly de-glycosylated or non-glycosylated forms, depending on the host cell selected or recombinant production and/or post-isolation processing.

Cadherin variants according to the invention may comprise polypeptide analogs wherein one or more of the specified (i.e., naturally encoded) amino acids is deleted or replaced or wherein one or more nonspecified amino acids are added: (1) without loss, and preferably with enhancement, of one or more of the biological activities or immunological characteristics specific for a cadherin; or (2) with specific disablement of a particular ligand/antiligand binding function of a cadherin.

Also contemplated by the present invention are antibody substances [e.g., monoclonal and polyclonal antibodies, chimeric and humanized antibodies, and antibody domains including Fab, Fab' and F(ab')$_2$, single chain antibodies, and Fv or single variable domains] and other binding proteins or peptides specifically react with cadherins of the invention. Antibody substances can be developed using isolated natural, recombinant or synthetic cadherin polypeptide products or host cells expressing such products on their surfaces. The antibody substances may be utilized for purifying polypeptides of the invention, for determining the tissue expression of the polypeptides and as antagonists of the ligand/antiligand binding activities of the cadherins. Specifically illustrating antibody substances of the invention are the monoclonal antibodies produced by the hybridomas designated 30Q8A, 30Q4H, 45A5G, 30S2F and 45C6A which were all deposited with the American Type Culture Collection (ATCC), 12301 Parklawn Drive, Rockville, Md. 20852 on Apr. 6, 1993 and were respectively assigned ATCC Deposit Nos. HB11316, HB11317, HB11318, HB11319 and HB11320. Also illustrating antibody substances of the invention is the monoclonal antibody produced by the hybridoma designated 30T11G which was deposited with the ATCC on Apr. 8, 1993 and was assigned ATCC Deposit No. HB11324.

The DNA and amino acid sequence information provided by the present invention makes possible the systematic analysis of the structure and function of the cadherins described herein and definition of those molecules with which the cadherins will interact on extracellular and intracellular levels. The idiotypes of anti-cadherin monoclonal antibodies of the invention are representative of such molecules and may mimic natural binding proteins (peptides and polypeptides) through which the intercellular and intracellular activities of cadherins are modulated. Alternately, they may represent new classes of modulators of cadherin activities. Anti-idiotypic antibodies, in turn, may represent new classes of biologically active cadherin equivalents.

Methods for modulating cadherin activity may involve contacting a cadherin with an antibody (or antibody fragment), another polypeptide or peptide ligand (including peptides derived from cadherins or other proteins, or a novel peptide), or a small molecule ligand that specifically binds to a portion (extracellular or cytoplasmic) of the cadherin.

Numerous aspects and advantages of the present invention will be apparent upon consideration of the following detailed description thereof, reference being made to the drawing wherein:

DETAILED DESCRIPTION

Figure 1:
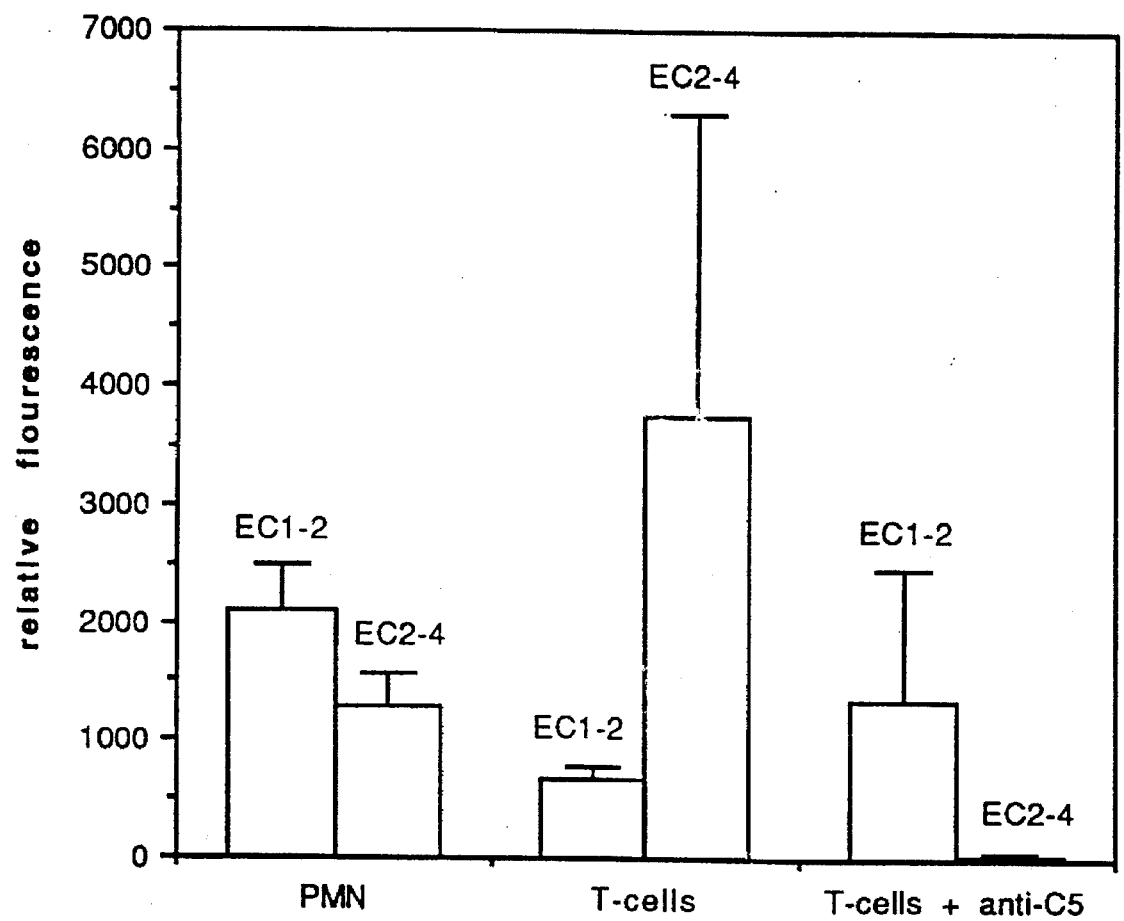
FIGURE 1 is a bar graph illustrating the binding of plymorphonuclear neutrophils and T cells to fusion proteins comprising extracellular subdomains of cadherin-5.

The present invention is illustrated by the following examples wherein Example 1 describes the isolation of cDNA sequences encoding rat cadherins-4 through -11 and -13; Example 2 describes the isolation of cDNA sequences encoding the human homologs of rat cadherins-4, -5, -6, -8, -10, -11 and -13 and the isolation of a human cadherin not identified in rat, cadherin-12; Example 3 characterizes the relationship of cadherins of the invention to previously identified cadherins in terms of amino acid sequence and structure. The generation of polyclonal and monoclonal antibodies specific for cadherins of the invention is described in Example 4. Example 5 describes the construction of expression constructs comprising cadherin-4, -5 and -8 sequences, transfection of mammalian cells with the constructs and results of cell-cell adhesion assays performed with the transfected cells. Example 6 presents the results of assays for cadherin mRNA and protein expression in various mammalian tissues, cells and cell lines. The results of in vitro transendothelial migration assays involving cadherin-5 and assays of neutrophil and T-cell binding to cadherin-5 fusion protein are described in Example 7. Example 8 describes expression of cadherin-5 in the blood-brain barrier and Example 9 describes cadherin-5 peptides that are capable of increasing endothelim permeability. Example 10 describes the association of the cytoplasmic domain of cadherin-5 with plakoglobin. The disclosures of Suzuki et al., *Cell Regulation*, supra; Suzuki et al., *J. Cell. Biol.*, 115, Abstract 72a (1991); Suzuki et al., *Cell. Struc. Funct.*, 16, 605 (1991); and Tanihara et al., *Invest. Ophthalmol. Vis. Sci.*, 32, 1013 (1991) are incorporated by reference herein for purposes of illustrating the background of the invention.

EXAMPLE 1

Partial cDNA clones encoding nine novel cadherins were isolated from rat brain and retina by PCR. Eight of the novel rat cadherin cDNAs were isolated using degenerate PCR primers based on highly conserved regions of the cytoplasmic domain of known cadherins and one was isolated using degenerate PCR primers based on moderately conserved regions of the extracellular domain of known cadherins.

A. Preparation of Rat cDNA

Total RNAs were prepared from rat brain by the guanidium isothiocyanate/cesium chloride method described in Maniatis et al., pp. 196 in *Molecular Cloning: A Laboratory Manual*, Cold Spring Harbor, N.Y.: Cold Spring Harbor Laboratory (1982). Brain poly(A)$^+$ RNAs were then isolated using an Invitrogen (San Diego, Calif.) FastTrack kit. Rat retina poly(A)$^+$ RNA was purchased from Clonetech (Palo Alto, Calif.). cDNA was synthesized from the poly(A)$^+$ RNA of both rat brain and retina using a cDNA synthesis kit (Boehringer Mannheim Corporation, Indianapolis, Ind.).

B. Design and Synthesis of PCR Primers Corresponding to Cadherin Cytoplasmic Domain A first pair of degenerate oligonucleotide primers, listed below in IUPAC nomenclature, was designed to correspond to highly conserved sequences in the cytoplasmic domain of mouse N-, E-, and P-cadherins. Underlined sequences at the end of each oligonucleotide indicate an EcoR1 site added to the primers to facilitate cloning of the fragments generated by PCR.

Degenerate Primer 1
TAPPYD (SEQ ID NO: 1)
5' GAATTCACNGCNCCNCCNTAYGA 3' (SEQ ID NO: 2)
Degenerate Primer 2
FKKLAD (SEQ ID NO: 3)
3' AARTTYTTYRANCGNCTCTTAAG 5' (SEQ ID NO: 4)
The degenerate oligonucleotides were synthesized using the Applied Biosystems model 380B DNA synthesizer (Foster City, Calif.).

C. Design and Synthesis of PCR Primers Corresponding to Cadherin Extracellular Domain A second pair of degenerate oligonucleotide primers, listed below in IUPAC nomenclature, was designed to correspond to moderately conserved sequences in the third subdomain of the extracellular domain of mouse N-, E-, and P-cadherins. The extracellular domains of the mouse N-, E- and P-cadherins have been characterized as having five internal subdomains, some of which may be involved in cadherin interaction with $Ca^{2+}$. Underlined sequences at the end of each oligonucleotide indicate an EcoR1 site added to the primers to facilitate cloning of the fragments generated by PCR.

Degenerate Primer 3
K(P/G)(L/I/V)D(F/Y)E (SEQ ID NO: 5)
5' GAATTCAARSSNNTNGAYTWYGA 3' (SEQ ID NO: 6)
Degerenate Primer 4
(N/D)E(A/P)PXF (SEQ ID NO: 7)
3' TRCTYSGNGGNNNNAARCTTAAG 5' (SEQ ID NO: 8)

D. Cloning of cDNA Encoding Eight Novel Rat Cadherins

PCR amplification reactions of rat brain and retina cDNA were carried out either with degenerate primers 1 and 2 or with degenerate primers 3 and 4 under conditions essentially the same as those described in Saiki et al., *Science*, 239, 487–491 (1988). Briefly, 100 ng of brain or retina first strand cDNA was used as template for amplification by Taq DNA polymerase (international Bioltechnology, New Haven, Conn.) using 10 μg of each primer set per reaction. PCR reactions were initiated by adding 2 units of Taq DNA polymerase to the reaction solution, after which 35 PCR reaction cycles were carried out. Reaction cycles consisted of denaturation performed at 94° C. for 1.5 minutes, oligo- nucleotide annealing at 45° C. for 2 minutes, and elongation at 72° C. for 3 minutes. The resulting PCR fragments were separated by agarose gel electrophoresis, and DNA bands of the expected size were extracted from the gel and digested with EcoR1. The fragments were then cloned into the M13 vector (Boehringer Mannheim Corp., Indianapolis, Ind.) and *E. coli* JM101 cells were transformed with the resulting constructs. Individual clones were then isolated and sequenced. Sequencing of the DNAs was carried out using a sequenase kit (United States Biochemicals, Cleveland, Ohio) and the resulting DNA and deduced amino acid sequences of the clones were compared to sequences of known cadherins using the Microgenie program (Beckman, Fullerton, Calif.).

Ten representative cDNA clones encoding cadherins were identified from the PCR reaction based on degenerate primers 1 and 2. Two clones corresponded to rat N-, and E-cadherins, but eight clones encoded previously unde- scribed cadherins, and were designated cadherins-4 through -11. The DNA and deduced amino acid sequences of the eight rat cytoplasmic domain cDNA clones are respectively set out in SEQ ID NOs: 9 and 10 (cadherin-4), SEQ ID NOs: 11 and 12 (cadherin-5), SEQ ID NOs: 13 and 14 (cadherin-6), SEQ ID NOs: 15 and 16 (cadherin-7), SEQ ID NOs: 17 and 18 (cadherin-8), SEQ ID NOs: 19 and 20 (cadherin-9), SEQ ID NOs: 21 and 22 (cadherin-10) and SEQ ID NOs: 23 and 24 (cadherin-11).

An additional novel cadherin was identified from the PCR reaction based on degenerate primers 3 and 4, and it was designated cadherin-13. The DNA and deduced amino acid sequences of the rat cadherin-13 fragment are respectively set out in SEQ ID NOs: 25 and 26.

The PCR reaction based on degenerate primers 3 and 4 also amplified sequences which were later determined to be fragments of the extracellular domains of rat cadherins-4, -5, -6, -8, -9, -10, and -11. The DNA and amino acid sequences of these extracellular fragments are respectively set out in SEQ ID NOs: 27 and 28 (cadherin-4), SEQ ID NOs: 29 and 30 (cadherin-5), SEQ ID NOs: 31 and 32 (cadherin-6), SEQ ID NOs: 33 and 34 (cadherin-8), SEQ ID NOs: 35 and 36 (cadherin-9), SEQ ID NOs: 37 and 38 (cadherin-10), SEQ ID NOs: 39 and 40 (cadherin-11).

Larger cadherin-8 and -10 cDNAs were isolated from a rat brain cDNA library made in Uni-ZAP vector (Stratagene, La Jolla, Calif.) using labelled cadherin-8 extracellular domain PCR fragment (SEQ ID NO: 17) or cadherin-10 extracellular domain fragment (SEQ ID NO: 21) as probes. Two types of cadherin-8 cDNA clones were isolated. The first type encodes a full length cadherin, but the second type encodes a truncated protein the sequence of which diverges from the first type of cadherin-8 clone near the N-terminus of the fifth extracellular subdomain (EC5). The truncated clone contains a short stretch of unique sequence in the N-terminus of EC5 but lacks the remainder of EC5, the transmembrane domain and the cytoplasmic domain. DNA and deduced amino acid sequences of the full length clone are respectively set out in SEQ ID NOs: 41 and 42 and the DNA and deduced amino acid sequences of the truncated cadherin-8 clone are set out in SEQ ID NOs: 43 and 44. The cadherin-10 cDNA clone that was isolated has an open reading frame which begins at a region corresponding to the middle of the first extracellular domain (EC1) of previously identified cadherins. The DNA and deduced amino acid sequences of the cadherin-10 clone are set out in SEQ ID NOs: 45 and 46.

EXAMPLE 2

Full length cDNAs encoding human homologs of rat cadherins-4, -8, -11 and -13 and partial cDNAs encoding human homologs of rat cadherins-6 and -10 were isolated from a human fetal brain cDNA library (λZapII vector, Stratagene). A full length cDNA encoding a human homolog of rat cadherin-5 was isolated from a human placental cDNA library (λgt11 vector, Dr. Millan, La Jolla Cancer Research Foundation, La Jolla, Calif.).

Probes for screening the human fetal brain and placental cDNA libraries were amplified by PCR from human brain cDNA (Dr. Taketani, Kansain Medical University, Moriguchi, Osaka, Japan) using the primers described in Example 1B-C. Probes consisting of human cadherin-4, -5, -6, -8, -10 and -11 sequences were generated using degenerate primers 1 and 2 and probes consisting of human cadherin-13 sequence were generated using degenerate primers 3 and 4. Amplification of the human fetal brain cDNA with degenerate primers 3 and 4 also generated a PCR fragment encoding a cadherin not isolated from rat, designated cadherin-12.

PCR fragments encoding human cadherins-4, -5, -6, -8, -10, -11, -12 and -13 were labelled with $^{32}$P and used to probe the human fetal brain and placental cDNA libraries according to the plaque hybridization method described in Ausubel et al., Eds., *Current Protocols in Molecular Biology*, Sections 6.1.1 to 6.1.4 and 6.2.1 to 6.2.3, John Wiley & Sons, New York (1987). Positives were plaque-purified and inserts were cut out using an in vivo excision method. The inserts were then subcloned into the M13 vector (Boehringer Mannheim) for sequencing.

Inserts consisting of full length cDNAs encoding human homologs of rat cadherins-4, -8, -11, -12 (putative) and -13 and partial cDNAs encoding human homologs of rat cadherins-6 and -10 were identified in clones from the human fetal brain cDNA library and a full length cDNA encoding a human homolog of rat cadherin-5 was identified in a clone from the human placental cDNA library. The DNA and deduced amino acid sequences of the human homologs are respectively set out in SEQ ID NOs: 47 and 48 (cadherin-4), SEQ ID NOs: 49 and 50 (cadherin-5), SEQ ID NOs: 51 and 52 (cadherin-6), SEQ ID NOs: 53 and 54 (cadherin-8), SEQ ID NOs: 55 and 56 (cadherin-10), SEQ ID NOs: 57 and 58 (cadherin-11), SEQ ID NOs: 59 and 60 (cadherin-12), and SEQ ID NOs: 61 and 62 (cadherin-13).

EXAMPLE 3

Comparison of the full-length sequences of the novel human cadherins described in Examples 1 and 2 with sequences of previously described cadherins and cadherin-related proteins provides support for the proposal that cadherins can be divided into at least three subgroups based on amino acid sequence identity and/or domain structure. Identity values for one possible alignment of the sequences of the extracellular domains of selected human cadherins are presented in Table 1 below.

TABLE 1

|    | N   | E   | P   | 4   | 5   | 8   | 11  | 12  | 13  |
|----|-----|-----|-----|-----|-----|-----|-----|-----|-----|
| N  | 100 | 45  | 45  | 68  | 30  | 34  | 35  | 33  | 46  |
| E  | 45  | 100 | 53  | 41  | 29  | 30  | 29  | 31  | 37  |
| P  | 45  | 53  | 100 | 29  | 30  | 29  | 31  | 31  | 38  |
| 4  | 68  | 41  | 41  | 100 | 29  | 33  | 34  | 33  | 44  |
| 5  | 30  | 29  | 30  | 29  | 100 | 40  | 41  | 39  | 32  |
| 8  | 34  | 30  | 29  | 33  | 40  | 100 | 66  | 58  | 32  |
| 11 | 35  | 29  | 31  | 34  | 41  | 66  | 100 | 58  | 31  |
| 12 | 33  | 31  | 31  | 33  | 39  | 58  | 58  | 100 | 33  |
| 13 | 46  | 37  | 38  | 44  | 32  | 32  | 31  | 33  | 100 |

Based on such sequence alignments and on the fact that certain combinations of cadherin sequences seem to have conserved stretches of amino acids when aligned, one subgroup of cadherins may include E-cadherin, N-cadherin, P-cadherin and cadherin-4, while a second subgroup may include cadherin-5, cadherin-8, cadherin-11 and cadherin-12. Cadherins-6, -7, -9 and -10 may also be included with the second subgroup based on their partial amino acid sequences disclosed herein. The amino acid sequence of cadherin-4 exhibits especially high amino acid sequence identity with that of R-cadherin (92%), indicating that cadherin-4 may be the human homolog of chicken R-cadherin. All cadherins in these two subgroups have a similar structure. Following an initiation codon, each has a signal sequence, prosequence, proteolytic cleavage site of precursor protein, an extracellular domain (which comprises five subdomains EC1-5), a transmembrane sequence and a cytoplasmic domain. For cadherin-5, these sequences/domains appear to correspond to about the following amino acid positions of SEQ ID NO: 50: 1–24 (signal sequence), 25–43 (prosequence), 44–147 (EC1), 148–254 (EC2), 255–368 (EC3), 369–475 (EC4), 476–589 (EC5), 590–616 (transmembrane sequence) and 617–780 (cytoplasmic domain).

Cadherin-13, T-cadherin and V-cadherin may be representative of a third subgroup of cadherins. Cadherin-13 consists of a cadherin-like extracellular domain, but has no domains that would correspond to the typical transmembrane or cytoplasmic domains of other cadherins. Even though about 10% of the clones obtained by PCR using degenerate primers 3 and 4 were cadherin-13 clones, none of the clones included sequences corresponding to a cytoplasmic domain. An attempt to isolate a cDNA that contained this region by PCR using a primer corresponding to the most C-terminal region of cadherin-13 available and a mixed oligonucleotide primer corresponding to a well-conserved amino acid sequence of the cytoplasmic domain of cadherins failed to generate any product with the anticipated molecular weight. A similar protein, T-cadherin, has been identified in chicken which also lacks the typical cadherin cytoplasmic domain. The amino acid sequence identity between the two molecules is about 80%. Cadherin-13 may be the human homologue of chicken T-cadherin or may be a closely related molecule. Human cadherin-13 and avian T-cadherin may also both be closely related to V-cadherin. A 29-amino acid amino terminal sequence of bovine V-cadherin is similar to the start of the precursor region of cadherin-13 (93%) and T-cadherin (79%). V-cadherin is a 135 KD protein which appears to be restricted in tissue distribution to endothelium. In constrast, mature T-cadherin has a molecular weight of 95 KD and shows a wide tissue distribution. Both V-cadherin and T-cadherin are linked to the cell membrane through phosphoinositiol.

EXAMPLE 4

Polyclonal and/or monoclonal antibodies specific for cadherins of the invention were generated.

A. Generation of Polyclonal Antibodies

Bacterial fusion proteins consisting of maltose binding protein fused to portions of cadherin extracellular subdomains (either human cadherin-4, -5 or -11, or rat cadherin-8) were generated and subsequently used for the generation of polyclonal antibodies.

A cDNA fragment corresponding to a 40 KD portion of the extracellular domain of human cadherin-5 (nucleotides 535 to 1527 of SEQ ID NO: 49) was synthesized by PCR from the full-length human cadherin-5 cDNA described in Example 2. The fragment was subcloned into the multicloning site (EcoR1-XbaI) of the pMAL-RI plasmid vector [New England Biolabs Inc. (NEB), Beverly, Mass.]. The resulting construct encodes maltose binding protein fused to the extracellular domain of cadherin-5. Constructs encoding maltose binding protein fused to the three N-terminal subdomains of human cadherin-4, rat cadherin-8 and human cadherin-11 were generated by similar methods.

E. coli NM522 cells (Stratagene) were then transformed with one of the fusion protein constructs and grown in quantity. After disruption of E. coli cells, the individual fusion proteins were purified by affinity column chromatography using amylose resin (NEB) according to the instructions of the manufacturer. When subjected to SDS-PAGE, the purified fusion proteins each showed essentially one band of the expected size.

A total of five hundred μg of a fusion protein in Freund's complete adjuvant was injected into rabbits at four subcutaneous sites. Subsequent injections were carried out at three week intervals using 100 μg of the fusion protein in Freund's incomplete adjuvant also at four subcutaneous sites. The resulting polyclonal sera generated from immunization of rabbits with cadherin-4, -5 or -8 fusion protein were collected and tested for specificity on L cells transfected with the appropriate cadherin sequence (see Example 5). Polyclonal serum generated from immunization of rabbits with cadherin-11 was also collected.

Immunoblotting of various cell types showed that the The anti-cadherin-4 polyclonal serum reacts with protein of about 130 KD in cells transfected with full length cadherin-4 cDNA and in rat brain. Cadherin-5-specific serum reacts with a protein of about 135 KD in L cells transfected with a full length cadherin-5 DNA and with a protein of about 135 KD in human umbilical vein endothelial cells (HUVEcs). The serum does not react with MDCK cells that expressed high levels of E-cadherin. In bovine aortic endothelial cells, the anti-cadherin-5 serum reacts with a protein of about 120 KD. Additionally, the anti-cadherin-5 serum reacts with a protein which has the same molecular weight in rat brain endothelial cells in culture. The cadherin-8 polyclonal antibody detected a strong band of about 90 KD and a weak band of about 130 KD in rat brain.

B. Generation of Monoclonal Antibodies Specific for Human Cadherin-5

Monoclonal antibodies to cadherin-5 were prepared using bacterial fusion proteins containing subdomains of the extracellular domain of human cadherin-5 as immunogens. The fusion proteins prepared included maltose binding protein and the extracellular subdomains 1–2 (EC1–2) or extracellular subdomains 2–4 (EC2–4) of cadherin-5 in the bacterial expression vector pMAL (NEB). The two fusion proteins were expressed in bacteria and purified on amylose-sepharose as described in foregoing section on generation of polyclonal antibodies. The purified fusion proteins were used separately to immunize mice at two subcutaneous sites (100 μg of fusion protein per mouse in Freund's complete adjuvant). The mice then were subcutaneously immunized with Freund's incomplete adjuvant.

The spleen from each mouse was removed sterility and treated in the same manner. Briefly, a single-cell suspension was formed by grinding the spleen between the frosted ends of two glass microscope slides submerged in serum free RPMI 1640 supplemented with 2 mM L-glutamine, 1 mM sodium pyruvate, 100 units/ml penicillin and 100 mg/ml streptomycin (RPMI) (Gibco, Canada). The cell suspension was filtered through a sterile 70-mesh cell strainer, and washed twice by centrifuging at 200 g for 5 minutes and resuspending the pellet in 20 ml serum free RPMI. Thymocytes taken from 3 naive Balb/c mice were prepared in a similar manner. NS-1 myeloma cells, kept in log phase in RPMI with 11% fetal bovine serum (FBS) (Hyclone Laboratories, Inc., Logan, Utah) for three days prior to fusion, were centrifuged at 200 g for 5 minutes, and the pellet was washed twice as described for the mouse spleen cells.

After washing, the spleen cells and myeloma cells were brought to a final volume of 10 ml in serum free RPMI, and 10 μl of that final volume was diluted 1:100 in serum free RPMI. Twenty μl of each dilution was removed, mixed with 20 μl 0.4% trypan blue stain in 0.85% saline, loaded onto a hemacytometer and counted. Two×$10^8$ spleen cells were combined with 4×$10^7$ NS-1 cells, centrifuged and the supernatant was aspirated. The cell pellets were dislodged by tapping the tube and 2 ml of 37° C. PEG 1500 (50% in 75 mM Hepes, pH 8.0) (Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×$10^6$ thymocytes/ml (plating medium). The suspension was dispensed into ten 96-well flat bottom tissue culture plates at 200 ml/well. Cells in plates were fed on days 2, 4, and 6 days post-fusion by aspirating approximately 100 ml from each well with an 18 G needle, and adding 100 ml/well plating medium described above except containing 10 units/ml IL-6 and lacking thymocytes.

Fusions 30 (from a mouse immunized with EC2–4) and 45 (from a mouse immunized with EC1–2) were screened initially by antibody capture ELISA, testing for presence of mouse IgG. Secondary screening of fusions 30 and 45 consisted of assays using plates coated with a monolayer of fixed endothelial cells for ELISAs. HUVEcs, Lewis rat brain endothelial cells (LeBCE), and bovine aortic endothelial cells (BAE) were allowed to grow in 96-well flat bottom tissue culture microtiter plates until the bottom of well was completely covered with a monolayer of cells. Plates were washed twice with 100 µl/well of $Ca^{2+}/Mg^{2+}$ free PBS (CMF-PBS) and aspirated completely. Cells were then fixed with 100 µl/well of 3% p-Formaldehyde, 1% Sucrose in CMF-PBS PBS at room temperature for 30 minutes. Cells were then permeablized with approximately 250 µl/well of CSK buffer (0.5% Triton 100, 100 mM NaCl, 10 mM PIPES, 2 mM MgCl) and incubated at room temperature for 30 minutes. Plates were blocked with 250 µl/well of 2% BSA in 1X CMF-PBS (blocking solution) and incubated at 37° C. for 60 minutes. Blocking solution was aspirated and 50 to 100 µl/well of supernatant from fusion plates was added. Plates were incubated at room temperature for 60 minutes and then were washed one time with 250 µl/well of 0.5% BSA in CMF-PBS (wash solution 1) and two times with 250 µl/well of CMF-PBS (wash solution 2). One hundred fifty µl of horseradish peroxidase conjugated goat anti-mouse IgG (fc) (Jackson ImmunoResearch, West Grove, Pa.) diluted 1:3500 in PBST was added and plates were incubated at room temperature for 60 minutes. Plates were washed as before and 150 µl substrate consisting of 1 mg/ml o-phenylene diamine (Sigma) and 0.1 ml/ml 30% $H_2O_2$ in 100 mM Citrate, pH 4.5 was added. The color reaction was stopped after 30 minutes with the addition of 50 µl of 15% $H_2SO_4$. $A_{490}$ was read on a plate reader (Dynatech). About 20 positive wells were identified for each fusion and were subsequently cloned.

Hybridomas were screened in cloning steps in an ELISA assay by testing for reactivity of monoclonals to the cadherin-5 EC2-4 fusion protein and excluding maltose binding protein reactive monoclonals. Immulon 4 plates (Dynatech, Cambridge, Mass.) were coated at 4° C. with 50 µl/well fusion protein diluted to 0.1 µg/well (for fusion protein) and to 0.2 µg/well (for maltose binding protein alone) in 50 mM carbonate buffer, pH 9.6. Plates were washed 3 times with PBS, 0.05% Tween 20 (PBST) and 50 µl hybridoma culture supernatant was added. After incubation at 37° C. for 30 minutes, and washing as above, 50 µl of horseradish peroxidase conjugated goat anti-mouse IgG (fc) (Jackson ImmunoReseach, West Grove, Pa.) diluted 1:3500 in PBST was added. Plates were incubated at 37° C. for 30 minutes and washed 4 times with PBST. One hundred µl substrate consisting of 1 mg/ml o-phenylene diamine (Sigma Chemical Co., St. Louis, Mo.) and 0.1 µl 30% $H_2O_2$ in 100 mM citrate, pH 4.5 was added. The color reaction was stopped after 5 minutes with the addition of 50 µl of 15% $H_2SO_4$. Absorbance at 490 nm was determined using a plate reader.

The hybridomas designated 30Q8A (ATCC HB11316), 30Q4H (ATCC HB11317), 45A5G (HB11318), 30S2F (HB11319), 45C6A (HB11320), 30T11G (ATCC HB11324), 30M8G, 30O6E and 30R1A] were identified as reactive with endothelial cells and with the cadherin-5 EC2-4 fusion protein. The hybridomas were cloned twice by limiting dilution and grown in ascites. The monoclonal antibodies produced by the hybridomas were isotyped in an ELISA assay. The results of the assay are presented in Table 2 below.

C. Subdomain Specificity of C5 Specific Monoclonal Antibodies

To determine if the hybridomas produced monoclonal antibodies reactive with unique epitopes of the extracellular domain of C5, the monoclonal antibodies were purified, biotinylated, and tested in a cross competition ELISA. Immulon IV 96-well plates were coated with either EC1-2 or EC2-4 cadherin-5 fusion protein at 0.2 µg/ml in 50 µl 50 mM $NaCO_3$, pH 9.6 overnight at 4° C. The wells were aspirated and washed three times with PBS/0.05% Tween 20. The plate was then blocked with 50 µl/well PBS, 2% BSA (Sigma) for 30 minutes at 37° C. Monoclonal antibodies were purified from hybridoma supernatants over a protein A-Sepharose column and the eluted antibody was dialyzed against 0.1M $NaCO_3$ pH 8.2. One mg/ml of antibody was reacted with 60 µl of a 1 mg/ml stock solution in DMSO of NHS-biotin (Pierce Chemical Co., Rockford, Ill.) for 1 hour at room temperature and the reaction was stopped by dialysis overnight at 4° C. against CMF/PBS. The biotinylated antibodies in PBS/0.05% Tween 20 were then added as primary antibody (50 µl/well) to a plate coated with fusion protein and incubated for 30 minutes at 37° C. The plate was then aspirated and washed three times with PBS/0.05% Tween 20. Peroxidase-conjugated strepavidin in PBS/Tween was added 50 µl/well and incubated for 30 minutes at 37° C. The plate was aspirated and washed three times in PBS/ 0.05% Tween 20, and o-phenylenediamine in 100 mM citrate buffer and hydrogen peroxide was added at 100 µl/well. The plate was developed at room temperature for 5–15 minutes. The reaction was stopped with 50 µl/well 15% sulfuric acid and the plate was read on a plate reader. Results of the assay are presented in Table 2 below.

To confirm subdomain specificity, the cadherin-5 fusion proteins EC1-2 and EC2-4 were run on SDS-PAGE (10%) and immunoblotted with the cadherin-5 specific monoclonal antibodies.

Table 2 below set outs the domain specificity and isotype of the cadherin-5 specific monoclonal antibodies.

TABLE 2

| Monoclonal Antibody | C5 Subdomain | Isotype |
|---|---|---|
| 30Q4H | 2 | $IgG_{2b}$ |
| 45A5G | 2 | $IgG_1$ |
| 45C6A | 2 | $IgG_1$ |
| 30S2F | 3–4 | $IgG_1$ |
| 30Q8A | 3–4 | $IgG_{2b}$ |
| 30T11G | 3–4 | $IgG_1$ |

Competition assays were carded out as described above for assays for binding to cadherin-5 EC2-4 fusion protein except that unlabelled primary cadherin-5 specific monoclonal antibodies (or mouse IgG) were added 30 minutes prior to addition of biotinylated cadherin-5 specific monoclonal antibodies. Monoclonal antibodies produced by the hybridomas 30M8G, 30O6E and 30RIA compete for a site that is near or identical to the binding site of the antibody produced by hybridoma 30Q4H.

EXAMPLE 5

Human cadherins-4 and -5 and rat cadherin -8 were expressed in mouse fibroblast L cells (ATCC CCL1.3) which do not normally express cadherins.

A. Construction of Expression Vectors

The cDNA sequences encoding human cadherins-4 and -5 which are described in Example 2 and the cDNA sequence encoding rat cadherin-8 which is described in Example 1 were subcloned into the multicloning site of expression vector pRC/RSV (Invitrogen).

Cadherin-4 DNA sequences were isolated by an in vivo excision procedure from the λZapII clone (described in Example 2) containing the entire coding sequence of cadherin-4. Using a helper virus, the sequences were excised from λZapII in the form of Bluescript plasmid. The plasmid was then cut with HindIII and blunt-ended with T4 polymerase. The resulting DNA fragment was redigested with SpeI to generate a cadherin-4 cDNA fragment having a blunt end and a SpeI sticky end. The fragment was purified by agarose gel electrophoresis and subcloned into the pRC/RSV expression vector that had been previously digested with SpeI and XbaI (the XbaI end was blunt-ended with T4 polymerase).

The λgt11 clone containing the entire coding sequence of cadherin-5 (described in Example 2) was cut with EcoRI and the resulting fragment containing the cadherin-5 sequences was purified by agarose gel electrophoresis. The purified fragment was then subcloned into the EcoRI site of the Bluescript plasmid. Cadherin-5 sequences were cut from the resulting construct with HincII and XbaI and subcloned into the NotI-XbaI site of the pRC/RSV vector.

The full length cDNA encoding rat cadherin-8 was excised from the Uni-ZAP clone described in Example 1 by digestion with KpnI, followed by blunt-ending and re-digestion with SpeI. The cadherin-8 encoding fragment was purified by agarose gel electrophoresis and was subcloned into the pRC/RSV vector which had been digested with XbaI, blunt-ended and redigested with SpeI.

B. Transfection of L Cells

Mouse fibroblast L cells were transfected with the human cadherin- 4 and -5 and rat cadherin-8 expression constructs by a $Ca^{2+}$ phosphate precipitation method and stable transfectants were obtained by G418 selection. Cadherin-4 and -8 transfectant cells showed a morphology similar to that of parental L cells (fibroblastic), but cadherin-5 transfectant cells exhibited a flattened morphology. Neuro 2a cells (ATCC CCL131) were also transfected by a $Ca^{2+}$ phosphate precipitation procedure with the cadherin-4 and cadherin-8 expression constructs. Cadherin-4 transfectants showed epithelial structure, suggesting that cadherin-4 has activity in epithelial structure formation and may be involved in the neural tissue development.

C. Northern and Western Blot Assays of Cadherin mRNA and Protein Expression in Transfected Cells Both cadherin-4, -5 and -8 transfectants showed mRNA of the expected size of 3.5 kb, 3.2 kb and 3 kb, respectively, in Northern blot analysis using the appropriate full length human cDNAs as a probe. (See Example 6A for a description of the Northern blot assay.)

For Western blots, cadherin-4, -5 and -8 transfectants were washed with PBS and SDS-PAGE sample buffer was added directly to the cells. SDS-PAGE (Laemmli) was carried out and and gels were blotted electrophoretically onto PVDF membrane. The membranes were incubated in TBS containing 5% skim milk for 2 hours at room temperature and then were incubated with the appropriate polyclonal antibody in TBS containing 0.05% Tween 20 for 1 hour at room temperature. After four washes (of 5 minutes each) with TBS containing 0.05% Tween 20, the membranes were incubated with alkaline phosphatase conjugated anti-rabbit IgG antibody (Promega Corp., Madison, Wis.) in TBS containing 0.05% Tween 20 for 1 hour at room temperature. The membranes were then washed again four times with TBS containing 0.05% Tween 20 at room temperature and developed by using Promega Western blue. Cadherin-4, -5 and -8 polyclonal antibodies each reacted with a band of about 130 KD.

D. Calcium Protection from Trypsin Digestion

Since cadherins have been shown to be protected from trypsin digestion by $Ca^{2+}$, the effect of $Ca^{2+}$ on trypsin treatment (0.01% soybean trypsin for 30 minutes at 37° C.) of human cadherin-4 and -5 and rat cadherin-8 expressed on the surface of transfected L cells was examined. Two mM $Ca^{2+}$ protected the cadherin-4 from the trypsin digestion, but cadherin-5 and cadherin-8 were digested easily even in the presence of 1–5 mM of $Ca^{2+}$.

E. Cell-Cell Adhesion Assay

The cell-cell adhesion activity of the transfected cells was assayed by a re-aggregation assay as described in Yoshida-Noro et al., *Devel. Biol.*, 101, 19–27 (1984). Briefly, transfectants were grown to near confluency and then dispersed into single cells with mild trypsin treatment (0.01% for 15 minutes) in the presence of 2 mM $Ca^{2+}$. After washing, the trypsinized cells were incubated in Hepes buffered saline (HBS) containing 2 mM $CaCl_2$, 1% BSA and 20 µg/ml deoxynuclease on a rotary shaker at 50 rpm for 30 to 60 minutes and then cell aggregation was monitored. Cadherin-4 transfectant cells aggregated within 30 minutes and formed relatively large aggregates, whereas cadherin-5 transfectant cells did not aggregate under the same conditions. However, cadherin-5 transfectants gradually re-aggregated and formed relatively small aggregate after prolonged incubation (4–5 hours or more). Similarly, cadherin-8 transfectants did not show significant cell adhesion activity. Parental L cells did not show cell adhesion under the same conditions. The sensitivity of cadherin-5 and cadherin-8 to trypsin digestion may account for the reduced cell adhesion seen in the reaggregation assay because the transfected L cells are initially dispersed with trypsin in the assay.

EXAMPLE 6

The expression of mRNAs encoding cadherins of the invention was examined in rat brain, kidney, liver, lung and skin and in various human cells by Northern blot analysis. The expression of cadherin protein was also examined in endothelial cells and leukocytes by immunofluorescence or immunoblotting.

A. Northern Blot Assays of Rat Tissue and Human Cells

Poly(A)$^+$ RNA from rat brain, kidney, liver, lung and skin was prepared as described in Example 1 for rat brain. The RNA preparations were then electrophoresed in an 0.8% agarose gel under denaturing conditions and transferred onto a nitrocellulose filter. Northern blot analyses were carried out according to a method described in Thomas, *Proc. Natl. Acad. Sci. USA*, 77, 5201–5202 (1980). Filters were hybridized with rat cadherin PCR fragments (described in Example 1) labeled with $^{32}P$, including fragments corresponding to cadherins-4 through -11. The final hybridization wash was in 0.2× standard saline citrate containing 0.1% sodium dodecyl sulfate at 65° C. for 10 minutes.

Cadherin-4 and cadherin-8 through -10 mRNAs were detected only in rat brain. The cadherin-8 PCR fragment hybridized to a major band of about 3.5 kb and a minor band of about 4.5 kb in rat brain. The mRNAs detected may be alternative splicing products and may correspond to the truncated and full length cadherin-8 clones described in Example 1. Cadherin-6 and -7 probes gave weak signals on rat brain mRNA even after prolonged exposure. Cadherins-5, -6 and -11 mRNAs were detected in rat brain and other rat tissues including cadherin-5 mRNA in lung and kidney, cadherin-6 mRNA in kidney, and cadherin- 11 mRNA in liver.

The expression of cadherin-8 and -11 in cultured human SK-N-SH neuroblastoma cells (ATCC HTB11), U251MG glioma cells and Y79 retinoblastoma cells (ATCC HTB18) was also assayed by Northern blot. Human cDNAs encoding cadherins-8 and -11 (described in Example 2) were labelled with $^{32}$P and used as probes of poly(A)$^+$ RNA prepared from the cells using an Invitrogen FastTrack kit.

The Northern blot procedure detected cadherin-8 RNA in the neuroblastoma and retinoblastoma cell lines, while cadherin-11 RNA was detected only in neuroblastoma cells. These results indicate that at least some of the cadherins of the invention are expressed in neurons and glial cells and/or their precursor cells.

Cadherin-5 RNA was detected by Northern blot assay of HUVECs (Clonetics), but was not detected in A431 human epidermoid carcinoma cells (ATCC CRL1555) or IMR90 human fibroblast cells (ATCC CCL186).

B. Immunoflourescence of Endothelial Cells and Immunoblotting of Leukocytes

Cultured endothelial cells isolated from bovine aorta, bovine brain microvasculature and human umbilical vein were subjected to immunofluorescence microscopy using anti-C5 polyclonal antibodies. Cadherin-5 protein at the cell junctions which was in close association with the peripheral actin microfilaments was labelled.

In contrast, when freshly isolated leukocytes (human PMN, lymphocytes and monocytes) or the monocyte-like cell line U937 were analyzed for the expression of cadherin-5 by immunoblotting using polyclonal antibodies and a monoclonal antibody (3006E) to cadherin-5, no cadherin-5 was detected. Furthermore, using a pan-cadherin antibody [Geiger et al., *J. Cell Science*, 97: 607–614 (1990)] specific for the cytoplasmic tail, no other cadherins were detected in these cell populations.

EXAMPLE 7

Three in vitro transendothelial migration assays were utilized to show that cadherin-5 may participate in the movement of leukocytes across the intercellular junctions of endothelium.

A. Transmigration Assays

The migration of leukocytes (either human polymorphonuclear neutrophils or rat T cells) was followed for specific periods of time (15 minutes for PMNs and 2 hours for T cells). Immunofluorescent labeling of leukocytes using antibodies to specific cellular markers was used distinguish between leukocytes and endothelium. The polyclonal antibodies described in Example 4 were used to measure changes in the distribution of cadherin-5. An antibody (Novocastra Laboratories Ltd., United Kingdom) to PE-CAM1 (CD31) which is an intercellular junction molecule in endothelium was used as a control.

The role of cadherin-5 in the transmigration of polymorphonuclear neutrophils (PMNs) across HUVEcs was analyzed. The system utilized, which is described in Furie et at., *J. Immunol.*, 143: 3309–3317 (1989), has been characterized with regard to electrical resistance of the endothelium and the adhesion molecules used in transmigration. HUVEcs were isolated in the absence of growth factor and cultured on human amniotic connective tissue in a two-chamber system. PMN migration on IL1β-treated HUVEcs has previously been shown to involve E-selectin and $\beta_2$ integrins (CD11/CD18). See Furie et al., *J. Immunol.*, 148: 2395–2484 (1992).

In the first assay, transmigration of PMNs was followed as an 11 minute time course on HUVEcs pretreated for four hours with IL1β (1.5 U/ml) (Collaborative Research Inc., Beford, Mass.). Prior to addition of neutrophils, antibodies to cadherin-5 heavily labelled the cell junctions of the HUVEcs in a continuous pattern. Pretreatment of the endothelial monolayer with IL1β had no effect on the distribution of cadherin-5 in the HUVEc monolayer compared to a control untreated culture. In the second assay, chemotaxis of PMNs across HUVEcs was stimulated by leukotriene B$_4$ (LTB$_4$) (Sigma) which was placed in the bottom chamber at $10^{-7}$M while neutrophils were added to the upper chamber. Chemotaxis of PMNs to LTB$_4$ across the endothelial monolayer was previously shown to be blocked by antibodies to CD11a, CD11b and ICAM-1. [See Furie et al, *Blood*, 78: 2089–2097 (1991)] In both assays, PMNs were identified with anti-CD45 antibody (Becton Dickinson, San Jose, Calif.).

In both assays during the 11-minute time course, the majority of the PMNs that adhered also transmigrated. Addition of neutrophils caused a rapid redistribution and regional loss of cadherin-5 even at the earliest time point (3 minutes). CD31 was also lost at sites of disruption of the monolayer, but in general appeared to be more stable during the transmigration process. The loss of cadherin-5 is probably the result of proteases released from the neutrophils during transmigration.

In a third assay, CD4 antigen activated rat T cells were utilized instead of PMNs (for a two-hour time course). Rat brain microvascular endothelium was grown on Transwell 5 micron polycarbonate membranes (Costar, Cambridge, Mass.). T cells were identified using an anti-CD4 antibody (Serotec, Indianapolis, Ind.). In this assay, the loss of cadherin-5 immunolabeling did not occur during transendothelial migration even though 10% of the T cells had crossed the endothelium after two hours. These results demonstrate differential effects of PMN versus T cells on intercellular junctions during tranendothelial migration. Analysis by confocal microscopy suggests that CD4 antigen-activated T cells and PMNs have a ligand that is able to interact with cadherin-5 on the endothelium during transmigration. Photomicrographs from confocal analysis show that during leukocyte transendothelial migration leukocytes can be found spanning the intercellular junction. The leukocyte separates the cell junction and cadherin-5 remains on adjacent cells even though the endothelial cells are not in contact.

B. Adhesion of PMNs and T Cells to Cadherin-5

To quantitate the binding of PMNs and activated T-cells to cadherin-5, a cell-substrate adhesion assay was developed. This assay utilized plate-bound fusion proteins containing various extracellular subdomains of cadherin-5 (EC 1-2 or EC2-4, see Example 4) and measured the binding of dye-labelled leukocytes to cadherin-5 protein using a cytofluor 2300 (Millipore, Bedford, Mass.).

The purified fusion proteins were absorbed to styrene plates and the binding of dye-labeled leukocytes to the fusion proteins was compared to binding to maltose binding protein and heat denatured bovine serum albumin (BSA) which was used to block nonspecific binding. The fusion proteins were dissolved in PBS containing Ca$^{2+}$ and Mg$^{2+}$, diluted into coating buffer and incubated overnight at 4° C. The plates were blocked with heat denatured BSA and then incubated with calcien (Molecular Probes, Eugene, Oreg.)-labelled cells for 1 hour at 37° C. Results of the assay are presented in FIGURE 1 wherein the relative fluorescence values reported are the mean value of three samples.

PMNs bound to fusion proteins comprising the EC2-4 of cadherin-5, but preferentially bound to fusion proteins comprising EC1-2. These results are consistent with presence of cadherin subdomain 2 sequences in both fusion proteins. CD4 antigen activated T cells bound EC2-4 fusion protein. All these results, which indicate that PMNs interact with a more terminal or exposed subdomain of cadherin-5, are consistent with the rate that these cell types cross the endothelium, PMNs transmigrate in a few minutes and T cells require 30–60 minutes. The binding of U937 cells could be blocked in a dose dependent manner by polyclonal antisera made to the cadherin-5 EC2-4 subdomains.

The results presented in the foregoing paragraph in combination with the results presented in Example 6B that leukocytes do not express cadherins suggests that the counter ligand to which cadherin-5 binds on leukocytes is a distantly related cadherin or is not a cadherin. Cadherin binding has previously been thought to be homotypic.

EXAMPLE 8

Expression of cadherin-5 in the blood-brain barrier in the endothelium of the cerebral cortex was assayed by Western blot and immunocytochemistry.

A SDS lysate was prepared by boiling bovine or macaque capillaries in SDS sample buffer for 2 minutes and then drawing the extract through a 25 G syringe needle. The extract was centrifuged in a microfuge for 15 minutes at 4° C. Protein concentration in the supernatant was determined by the BCA method (Pierce) using bovine serum albumin as a standard. Samples of the supernatent (75 µg) were separated by SDS-PAGE (Laemmli) and electrophoretically transferred to nitrocellulose. The nitrocellulose was blocked with 5% milk and 10% FBS in Tris-buffered saline, pH 8.0, containing 0.05% Tween 20. Cadherin-5 specific monoclonal antibodies (30Q4H and 45C6A) were added. After washing to remove unbound antibody, the filters were incubated with alkaline phosphatase-conjugated anti-mouse IgG (Promega, Madison, Wis.). Reactive bands were visualized by addition of NBT/BCIP (Sigma, St. Louis, Mo.). Expression of cadherin-5 was detected in the freshly isolated bovine and macaque capillaries.

The Western blot results were confirmed by immunocytochemistry using the cadherin-5 antibodies 30Q4H and 45C6A. Macaque cerebral cortex was incubated in 15% sucrose in PBS for 30 minutes at 4° C. and embedded in OCT compound Crissue-Tek, Elkhart, Ind.) in cryomolds and quickly frozen. Six micron sections were cut and placed on glass slides. The slides were washed with PBS and fixed in 3% p-formaldehyde for 5 minutes. To permeabilize the tissue sections the slides were immersed in −20° C. acetone for 10 minutes and air dried. The sections were blocked with 2% goat serum and 1% BSA in PBS for 30 minutes and then incubated with the primary antisera for 1 hour at room temperature. The sections were rinsed 3 times in PBS containing 0.1% BSA and incubated with biotinylated anti-rabbit or anti-mouse IgG (Vector Laboratories, Burlingame, Calif.) in 1% BSA in PBS for 30 minutes. After rinsing 3 times, strepavidin-conjugated with horseradish peroxidase (Vector Laboratories) was added for 30 minutes and washed 3 times. Immunolabeling was detected by reaction with diaminobenzoic acid in the presence of $NiCl_2$. The monoclonal antibody 45C6A only appeared to label larger vessels and the monoclonal antibody 30Q4H labeled both large and microvessels. The cell junctions of cerebral capillaries were labelled with the anti-cadherin-5 antibodies in a localized site.

These results and the results presented in Example 7 suggest cadherin-5 is involved in maintenance of the blood-brain barrier and that cadherin-5 peptides or cadherin-5 specific monoclonal antibodies may be able to open the blood-brain barrier.

EXAMPLE 9

Patent Cooperation Treaty (PCT) International Publication No. WO 91/04745 discusses fragments of cell adhesion molecules and antibodies to cell adhesion molecules which are purported to disrupt microvascular and endothelial cell tight junctions.

Three cadherin-5 peptides corresponding to the cell binding domain [HAV region, Blaschuk et al., *Devel. Biol.*, 139: 227–229 (1990)], the calcium binding region A1 and the calcium binding region B1 of E-cadherin [Ringwald et al., *EMBO J.*, 6:3647–3653 (1987)] were tested for the ability to affect the permeability of brain endothelium. The peptides utilized had the following sequences:

Peptide 1 (Amino acids 114 to 128 of SEQ ID NO: 50) LTAVIVDKDTGENLE,

Peptide 2 (Amino acids 132 to 145 of SEQ ID NO: 50) SFTIKVHDVNDNWP, and

Peptide 3 (Amino acids 168 to 178 of SEQ ID NO: 50) SVTAVDADDPT, respectively.

Permeability was measured using a two-chamber culture system (Costar). Rat brain microvascular endothelium was grown on 12 mm Transwell filters with 3 micron pores (Costar) in the culture system. When the monolayers were confluent, two weeks after plating, $^3$H-inulin (201 mCi/g) (New England Nuclear, Boston, Mass.) was added to the upper chamber. Cadherin-5 peptide at 100 µg/ml was added to both the upper and lower chambers. Radioactivity appearing in the bottom chamber was measured at 15 minute intervals over a two hour time course carried out at 37° C. and was compared to the radioactivity appearing in the bottom chamber of cultures where no peptide was added or where no endothelial cells were present.

Both peptides 1 and 3 increased endothelium permeability in comparison to control cultures. The increase in permeability obtained with peptide 3 was 2.5-fold and the increase with peptide 1 was 1.5-fold over the controls. Peptide 2 had no effect on permeability.

EXAMPLE 10

The functional properties of cadherins involve not only specific intercellular interactions, but also involve intracellular interactions with the cytoskeleton. Immunoprecipitation experiments utilizing the cadherin-5-specific rabbit polyclonal antibodies and the monoclonal antibody 30Q8A (see Example 4) were performed to determine with which proteins cadherin-5 interacts on an intracellular level.

Endothelial cells were metabolically labeled overnight with 50 µCi/ml of [$^{35}$S]-methionine and were then extracted with 0.5% Triton X-100 in 10 mM HEPES pH 7.4, 0.15M NaCl, 2 mM EDTA, 2 mM EGTA, 1 mM phenanthroline and protease inhibitors. The inhibitors included 1 mM PMSF, 10 µg/ml aprotinin, leupeptin, pepstatin A, antipain, soybean trypsin inhibitor, 100 µg/ml chymostatin and TPCK, 40 µg/ml of TPCK and bestatin, 50 µg/ml of benzamidine, 1 mM o-vanidate and 20 mM NaF. After 20 minutes on ice, the cells were scraped and centrifuged in a microfuge for 30 minutes at 4° C. The supernatant was precleared and either polyclonal anti-cadherin-5 or normal rabbit serum was added and incubated overnight at 4° C. Protein A-sepharose (Pharmacia, Piscataway, N.J.) was added for 2 hours at 4° C. and centrifuged. A first low stringency wash with 10 mM HEPES pH 7.4, 0.15M NaCl, 2 mM EDTA and 2 mM EGTA containing 1% Triton X-100, 0.5% DOC and 0.2% SDS was performed. A second high stringency wash was performed with the same buffer containing 2% SDS. A final wash was then performed with Tris-buffered saline, and the samples were boiled and analyzed on SDS/PAGE (7%). Three bands with molecular weights of 104 KD, 95 KD, and 82 KD were identified as associated with cadherin-5.

Three intracellular proteins, termed catenins, have previously been identified by their ability to bind to the cytoplasmic domain of E-cadherin. These proteins have been designated α, β, and γ catenins and have molecular weights of 102 KD, 88 KD and 80 KD, respectively [Ozawa et al., *EMBO J.* 8:1711–1717 (1989)]. The association of catenins with E-cadherin seem to be required for E-cadherin function because deletion of the cytoplasmic domain of E-cadherin results in loss of cell adhesion function and catenin binding. The molecular cloning of α-catenin has shown it to be a vinculin-like protein [Nagafuki et al., *Cell,* 65: 849–857 (1991); Herrenkenecht et al., *Proc. Natl. Acad. Sci. USA,* 88: 9156–9160 (1991)]. The amino acid sequence of the Xenopus β-catenin [McCrea et al., *Science,* 254: 1359–1361 (1991)] exhibits 63% similarity to the human protein plakoglobin [Franke et al., *Proc. Natl. Acad. Sci. USA,* 86: 4027–4031 (1989)]. Plakoglobin has been localized to both the cytoplasmic region of desmosome and adherens junctions in epithelial cells. The desmonsomal component desmoglein I interacts with plakoglobin and is a member of the cadherin superfamily [Koch et al., *Eur. J. Cell. Biol.,* 53: 1–12 (1990)]. Plakoglobin has a molecular weight of 82 KD and may be the γ-catenin [Peifer et al, *J. Cell Biol.,* 118: 681–691 (1992)]. Even though endothelial cells lack desmosome, they have been shown to contain plakoglobin-associated with intercellular junctions [Franke et al., *Biol. of the Cell,* 59: 205–218 (1987)]. Other cytoskeletal elements associated with cadherins are ankyrin and fodrin [Nelson et al., *J. Cell Biol.,* 110: 349–357 (1990)].

To identify whether plakoglobin was one of the proteins complexed to cadherin-5, an unlabeled lysate of bovine aortic endothelial cells was made and immunoprecipitation was carried out as described above using anti-cadherin-5 antibody. The unlabelled immunoprecipitates were separated by SDS/PAGE and then electrophoretically transferred to nitrocellulose. The membrane was blocked with 5% milk in Tris-buffered saline, pH 8.0, containing 0.05% Tween 20 (TBST) and then was incubated with the murine monoclonal antibody PG5.1 (IBI Research Products, Cambridge, Mass.) to plakoglobin in blocking solution (1:20) for 1 hour at room temperature. The membrane was washed with TBST and then incubated with goat anti-mouse IgG conjugated to alkaline phosphatase. An 82 KD protein was identified using NBT/BCIP under both low and high stringency wash conditions. These results demonstrate that plakoglobin is tightly associated with the cytoplasmic domain of cadherin-5 in endothelium. Immunofluorescence studies of regenerated endothelium show that cadherin-5 and plakoglobin are localized to the cell junctions and are coordinately regulated.

The interation of cadherin-5 with plakoglobin may be a target for modulation of cadherin-5 activity.

While the present invention has been described in terms of preferred embodiments, it is understood that variations and improvements will occur to those skilled in the art. Thus, only such limitations as appear in the appended claims should be placed on the scope of the invention.

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Thr  Ala  Pro  Pro  Tyr  Asp
1                   5
```

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
GAATTCACNG  CNCCNCCNTA  YGA                                    23
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Phe  Lys  Lys  Leu  Ala  Asp
    1                   5

( 2 ) INFORMATION FOR SEQ ID NO:4:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:4:

GAATTCTCNG CNAR YTT YTT RAA                                                                                23

( 2 ) INFORMATION FOR SEQ ID NO:5:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
                ( A ) NAME/KEY: Modified-site
                ( B ) LOCATION: 2
                ( D ) OTHER INFORMATION: /note="The amino acid at this
                        position is a proline or a glycine."

( i x ) FEATURE:
                ( A ) NAME/KEY: Modified-site
                ( B ) LOCATION: 3
                ( D ) OTHER INFORMATION: /note="The amino acid at this
                        position is a leucine, an isoleucine or a valine."

( i x ) FEATURE:
                ( A ) NAME/KEY: Modified-site
                ( B ) LOCATION: 5
                ( D ) OTHER INFORMATION: /note="The amino acid at this
                        position is a phenylalanine or a tyrosine."

( x i ) SEQUENCE DESCRIPTION: SEQ ID NO:5:

Lys  Xaa  Xaa  Asp  Xaa  Glu
    1                   5

( 2 ) INFORMATION FOR SEQ ID NO:6:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:6:

GAATTCAARS SNNTNGA YTW YGA                                                                                 23

( 2 ) INFORMATION FOR SEQ ID NO:7:

( i ) SEQUENCE CHARACTERISTICS:
                ( A ) LENGTH: 6 amino acids
                ( B ) TYPE: amino acid
                ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="The amino acid at this position is an asparagine or an aspartic acid."

( i x ) FEATURE:
    ( A ) NAME/KEY: Modified-site
    ( B ) LOCATION: 3
    ( D ) OTHER INFORMATION: /note="The amino acid at this position is an alanine or a proline."

( x i ) SEQUENCE DESCRIPTION: SEQ ID NO:7:

```
Xaa  Glu  Xaa  Pro  Xaa  Phe
1               5
```

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
GAATTCRAAN NNNGGNGS Y T CRT                                              23
```

( 2 ) INFORMATION FOR SEQ ID NO:9:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
TCCCTGCTGG TCTTCGACTA CGAAGGCAGC GGTTCTACTG CAGGCTCTGT CAGCTCCCTG        60
AACTCCTCCA GCTCCGGGGA TCAAGATTAC GACTACTTGA ATGACTGGGG GCCCCGG          117
```

( 2 ) INFORMATION FOR SEQ ID NO:10:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser  Leu  Leu  Val  Phe  Asp  Tyr  Glu  Gly  Ser  Gly  Ser  Thr  Ala  Gly  Ser
1                   5                        10                       15
Val  Ser  Ser  Leu  Asn  Ser  Ser  Ser  Gly  Asp  Gln  Asp  Tyr  Asp  Tyr
               20                       25                       30
Leu  Asn  Asp  Trp  Gly  Pro  Arg
               35
```

( 2 ) INFORMATION FOR SEQ ID NO:11:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ACACTGCACA TCTACGGCTA CGAGGGCACA GAGTCCATCG CAGAGTCCCT CAGCTCCTG  60

AGCACCAATT CCTCCGACTC TGACATCGAC TATGACTTCC TCAATGACTG GGGACCCAGG  120

( 2 ) INFORMATION FOR SEQ ID NO:12:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Thr Leu His Ile Tyr Gly Tyr Glu Gly Thr Glu Ser Ile Ala Glu Ser
 1               5                  10                  15

Leu Ser Ser Leu Ser Thr Asn Ser Ser Asp Ser Asp Ile Asp Tyr Asp
                20                  25                  30

Phe Leu Asn Asp Trp Gly Pro Arg
                35              40
```

( 2 ) INFORMATION FOR SEQ ID NO:13:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TCCTTGGCCA CCTATGCCTA CGAAGGAACT GGCTCGGTGG CCGACTCCCT GAGCTCACTA  60

GAATCAGTGA CCACAGATGG AGACCAAGAT TATGACTATT TGAGTGACTG GGGCCCTCGA  120

( 2 ) INFORMATION FOR SEQ ID NO:14:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Ser Leu Ala Thr Tyr Ala Tyr Glu Gly Thr Gly Ser Val Ala Asp Ser
 1               5                  10                  15

Leu Ser Ser Leu Glu Ser Val Thr Thr Asp Gly Asp Gln Asp Tyr Asp
                20                  25                  30

Tyr Leu Ser Asp Trp Gly Pro Arg
                35              40
```

( 2 ) INFORMATION FOR SEQ ID NO:15:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TCGCTTCAGA CTTATGCATT TGAAGGAAAT GGCTCAGTAG CTGAATCTCT CAGTTCTTTA  60

```
GATTCTAACA GCTCGAACTC TGATCAGAAT TATGACTACC TTAGTGACTG GGGTCCTCTC        120
```

( 2 ) INFORMATION FOR SEQ ID NO:16:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ser Leu Gln Thr Tyr Ala Phe Glu Gly Asn Gly Ser Val Ala Glu Ser
 1               5                  10                  15

Leu Ser Ser Leu Asp Ser Asn Ser Asn Ser Asp Gln Asn Tyr Asp
            20                  25                  30

Tyr Leu Ser Asp Trp Gly Pro Arg
            35                  40
```

( 2 ) INFORMATION FOR SEQ ID NO:17:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
TCCATTCAGA TTTATGGCTA TGAAGGCCGA GGGTCTGTGG CTGGCTCTCT CAGCTCGTTG         60
GAGTCCACCA CATCAGACTC AGACCAGAAT TTTGACTACC TCAGTGACTG GGGTCCCCGC        120
```

( 2 ) INFORMATION FOR SEQ ID NO:18:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Ser Ile Gln Ile Tyr Gly Tyr Glu Gly Arg Gly Ser Val Ala Gly Ser
 1               5                  10                  15

Leu Ser Ser Leu Glu Ser Thr Thr Ser Asp Ser Asp Gln Asn Phe Asp
            20                  25                  30

Tyr Leu Ser Asp Trp Gly Pro Arg
            35                  40
```

( 2 ) INFORMATION FOR SEQ ID NO:19:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
TCCTTGGCCA CTTACGCCTA TGAAGGGAAT GATTCTGTAG CCAATTCTCT CAGCTCCTTA         60
GAATCTCTCA CAGCTGATTG TACCCAGGAT TATGACTACC TTAGTGACTG GGGGCCACGC        120
```

( 2 ) INFORMATION FOR SEQ ID NO:20:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Ser Leu Ala Thr Tyr Ala Tyr Glu Gly Asn Asp Ser Val Ala Asn Ser
1               5                   10                  15
Leu Ser Ser Leu Glu Ser Leu Thr Ala Asp Cys Asn Gln Asp Tyr Asp
            20                  25                  30
Tyr Leu Ser Asp Trp Gly Pro Arg
            35                  40
```

( 2 ) INFORMATION FOR SEQ ID NO:21:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
TCGCTGGCTA CCTATGCCTA TGAAGGAAAC GACTCTGTTG CTAATCTCT  GAGCTCCTTA    60
GAATCAGGTA CCACTGAAGG AGACCAAAAC TACGATTACC TTCGAGAATG GGGGCCTCGG   120
```

( 2 ) INFORMATION FOR SEQ ID NO:22:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Ser Leu Ala Thr Tyr Ala Tyr Glu Gly Asn Asp Ser Val Ala Glu Ser
1               5                   10                  15
Leu Ser Ser Leu Glu Ser Gly Thr Thr Glu Gly Asp Gln Asn Tyr Asp
            20                  25                  30
Tyr Leu Arg Glu Trp Gly Pro Arg
            35                  40
```

( 2 ) INFORMATION FOR SEQ ID NO:23:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
TCCATCCAAA TCTATGGTTA TGAGGGCAGG GGTTCCGTGG CTGGGTCCCT GAGCTCCTTG    60
GAGTCTGCCA CCACAGATTC GGACCTGGAC TACGACTATC TACAGAACTG GGGACCTCGG   120
```

( 2 ) INFORMATION FOR SEQ ID NO:24:

( i ) SEQUENCE CHARACTERISTICS:
        ( A ) LENGTH: 40 amino acids (B) TYPE: amino acid
(D) TOPOLOGY: linear (ii) MOLECULE TYPE: protein (xi) SEQUENCE DESCRIPTION: SEQ ID NO:24:

```
Ser Ile Gln Ile Tyr Gly Tyr Glu Gly Arg Gly Ser Val Ala Gly Ser
1               5                   10                  15
Leu Ser Ser Leu Glu Ser Ala Thr Thr Asp Ser Asp Leu Asp Tyr Asp
            20                  25                  30
Tyr Leu Gln Asn Trp Gly Pro Arg
            35                  40
```

(2) INFORMATION FOR SEQ ID NO:25:

(i) SEQUENCE CHARACTERISTICS:
    (A) LENGTH: 150 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:25:

```
AAGCGGTTTG ATTACGAGAT CTCTGCCTTT CACACCCTGC TGATCAAAGT GGAGAATGAG      60
GACCCATTGG TACCCGACGT CTCCTATGGC CCCAGCTCCA CGGCCACTGT CCACATCACG     120
GTCTTGGATG TCAACGAGGG ACCAGTCTTC                                      150
```

(2) INFORMATION FOR SEQ ID NO:26:

(i) SEQUENCE CHARACTERISTICS:
    (A) LENGTH: 50 amino acids
    (B) TYPE: amino acid
    (D) TOPOLOGY: linear (ii) MOLECULE TYPE: protein (xi) SEQUENCE DESCRIPTION: SEQ ID NO:26:

```
Lys Arg Phe Asp Tyr Glu Ile Ser Ala Phe His Thr Leu Leu Ile Lys
1               5                   10                  15
Val Glu Asn Glu Asp Pro Leu Val Pro Asp Val Ser Tyr Gly Pro Ser
            20                  25                  30
Ser Thr Ala Thr Val His Ile Thr Val Leu Asp Val Asn Glu Gly Pro
            35                  40                  45
Val Phe
    50
```

(2) INFORMATION FOR SEQ ID NO:27:

(i) SEQUENCE CHARACTERISTICS:
    (A) LENGTH: 150 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:27:

```
AAGGGTATGG ATTATGAGCT GAACCGTGCC TCCATGCTGA CCATAATGGT GTCCAACCAG      60
GCGCCCCTGG CCAGCGGGAT CCAGATGTCC TTCCAGTCCA CAGTGGGGGT AACCATCTCT     120
GTCACCGATG TCAACGAAGC CCCCTACTTC                                      150
```

(2) INFORMATION FOR SEQ ID NO:28:

( i ) SEQUENCE CHARACTERISTICS:
    ( A ) LENGTH: 50 amino acids
    ( B ) TYPE: amino acid
    ( D ) TOPOLOGY: linear ( i i ) MOLECULE TYPE: protein ( x i ) SEQUENCE DESCRIPTION: SEQ ID NO:28:

```
Lys Gly Met Asp Tyr Glu Leu Asn Arg Ala Ser Met Leu Thr Ile Met
1               5                   10                  15
Val Ser Asn Gln Ala Pro Leu Ala Ser Gly Ile Gln Met Ser Phe Gln
            20                  25                  30
Ser Thr Val Gly Val Thr Ile Ser Val Thr Asp Val Asn Glu Ala Pro
        35                  40                  45
Tyr Phe
    50
```

( 2 ) INFORMATION FOR SEQ ID NO:29:

( i ) SEQUENCE CHARACTERISTICS:
    ( A ) LENGTH: 153 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:29:

```
AAACGACTGG ATTTTGAACT CATCCAGCAG TACACGTTCC ACATCGAGGC CACAGACCCC        60
ACTATCAGAC TCGGATACCT GAGCAGCACT GCGGGCAAAA ACAAAGCCAA GATCATCATC       120
AATGTCCTAG ATGTGGATGA GCCCCCTGTT TTC                                    153
```

( 2 ) INFORMATION FOR SEQ ID NO:30:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: protein ( x i ) SEQUENCE DESCRIPTION: SEQ ID NO:30:

```
Lys Arg Leu Asp Phe Glu Leu Ile Gln Gln Tyr Thr Phe His Ile Glu
1               5                   10                  15
Ala Thr Asp Pro Thr Ile Arg Leu Gly Tyr Leu Ser Ser Thr Ala Gly
            20                  25                  30
Lys Asn Lys Ala Lys Ile Ile Ile Asn Val Leu Asp Val Asp Glu Pro
        35                  40                  45
Pro Val Phe
    50
```

( 2 ) INFORMATION FOR SEQ ID NO:31:

( i ) SEQUENCE CHARACTERISTICS:
    ( A ) LENGTH: 153 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:31:

```
AAGGGTTTGG ATTTTGAAAA GAAGAAAGTG TATACCCTTA AAGTGGAAGC CTCCAATCCT        60
```

TATGTTGAGC CACGATTTCT CTACTTGGGG CCTTTCAAAG ATTCAGCCAC GGTTAGAATT    120

GTGGTGGAGG ATGTAGATGA ACCTCCTGCC TTC    153

( 2 ) INFORMATION FOR SEQ ID NO:32:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Lys Gly Leu Asp Phe Glu Lys Lys Lys Val Tyr Thr Leu Lys Val Glu
 1               5                  10                  15

Ala Ser Asn Pro Tyr Val Glu Pro Arg Phe Leu Tyr Leu Gly Pro Phe
                20                  25                  30

Lys Asp Ser Ala Thr Val Arg Ile Val Val Glu Asp Val Asp Glu Pro
                35                  40                  45

Pro Ala Phe
        50
```

( 2 ) INFORMATION FOR SEQ ID NO:33:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

AAGCCTCTGG ACTTTGAGAC CAAAAAATCC TATACTCTGA AGGTGGAGGC AGCCAATATC    60

CACATCGACC CACGTTTCAG TGGCAGGGGA CCCTTTAAAG ATACAGCAAC AGTCAAAATT    120

GTTGTAGAGG ATGCTGATGA GCCTCCGGTC TTC    153

( 2 ) INFORMATION FOR SEQ ID NO:34:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Asp Ala Leu Asp Phe Glu Thr Lys Lys Ser Tyr Thr Leu Lys Val Glu
 1               5                  10                  15

Ala Ala Asn Ile His Ile Asp Pro Arg Phe Ser Gly Arg Gly Pro Phe
                20                  25                  30

Lys Asp Thr Ala Thr Val Lys Ile Val Val Glu Asp Ala Asp Glu Pro
                35                  40                  45

Pro Val Phe
        50
```

( 2 ) INFORMATION FOR SEQ ID NO:35:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

| | | | | |
|---|---|---|---|---|
| AAGGGGGTGG | ACTATGAAGC | CAAAACAAGT | TATACCCTGC | GCATAGAAGC TGCAAATCGA | 60 |
| GATGCTGATC | CCCGGTTTCT | GAGCTTGGGT | CCATTCAGTG | ACACAACAAC AGTTAAGATA | 120 |
| ATTGTGGAAG | ACGTGGATGA | ACCCCCGTACT | C | | 152 |

( 2 ) INFORMATION FOR SEQ ID NO:36:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Lys Gly Val Asp Tyr Glu Ala Lys Thr Ser Tyr Thr Leu Arg Ile Glu
 1               5                  10                  15

Ala Ala Asn Arg Asp Ala Asp Pro Arg Phe Leu Ser Leu Gly Pro Phe
            20                  25                  30

Ser Asp Thr Thr Thr Val Lys Ile Ile Val Glu Asp Val Asp Glu Pro
        35                  40                  45

Pro Tyr Ser
    50
```

( 2 ) INFORMATION FOR SEQ ID NO:37:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

| | | | | | |
|---|---|---|---|---|---|
| AAGCCACTTG | ACTATGAGAA | CCGAAGACTA | TATACACTGA | AGGTGGAGGC AGAAAATACC | 60 |
| CATGTGGATC | CACGTTTTTA | CTATTTAGGG | CCATTCAAAG | ATACAACAAT TGTAAAAATC | 120 |
| TCCATAGAAG | ACGTGGATGA | GCCACCCCCC | TTT | | 153 |

( 2 ) INFORMATION FOR SEQ ID NO:38:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Lys Pro Leu Asp Tyr Glu Asn Arg Arg Leu Tyr Thr Leu Lys Val Glu
 1               5                  10                  15

Ala Glu Asn Thr His Val Asp Pro Arg Phe Tyr Tyr Leu Gly Pro Phe
            20                  25                  30

Lys Asp Thr Thr Ile Val Lys Ile Ser Ile Glu Asp Val Asp Glu Pro
        35                  40                  45

Pro Pro Phe
    50
```

( 2 ) INFORMATION FOR SEQ ID NO:39:

( i ) SEQUENCE CHARACTERISTICS:
    ( A ) LENGTH: 153 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:39:

| | | | | | |
|---|---|---|---|---|---|
| AGGGGTGTGG | ATTATGAAAC | CAAAAGAGCA | TATAGCTTGA | AGGTAGAGGC | GGCCAATGTA | 60 |
| CACATTGATC | CGAAGTTCAT | CAGCAATGGA | CCTTTCAAGG | ACACAGTGAC | TGTCAAGATT | 120 |
| GCAGTAGAAG | ATGCCAATGA | GCCCCCTCCC | TTC | | | 153 |

( 2 ) INFORMATION FOR SEQ ID NO:40:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: protein ( x i ) SEQUENCE DESCRIPTION: SEQ ID NO:40:

Arg Gly Val Asp Tyr Glu Thr Lys Arg Ala Tyr Ser Leu Lys Val Glu
1               5                      10                   15

Ala Ala Asn Val His Ile Asp Pro Lys Phe Ile Ser Asn Gly Pro Phe
             20                     25                    30

Lys Asp Thr Val Thr Val Lys Ile Ala Val Glu Asp Ala Asn Glu Pro
        35                     40                    45

Pro Pro Phe
50

( 2 ) INFORMATION FOR SEQ ID NO:41:

( i ) SEQUENCE CHARACTERISTICS:
    ( A ) LENGTH: 3136 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:41:

| | | | | | |
|---|---|---|---|---|---|
| GGCACGAGCG | CAAGCCGGGG | AGCGCTCGGC | CCAGAATTAG | TGGATGGATT | TGGAATCTCC | 60 |
| CTGCCTCCTC | CAAGCTCCGC | CACTGCCACT | TTAGGCAGAG | ACCTGAGCGT | CAACACGCGA | 120 |
| GCCGTACTTT | TAGGCTGCGG | ACACTGAGCC | CAGCGCGCCA | GCTTCGCATC | TCCGCACCAG | 180 |
| GCTCCACAGC | TCGGAGAGGC | ATGAACGCGA | TCCGGAGGAG | ACTACCCTGC | GCGCGGGGAT | 240 |
| CCGTGGACAT | TAGCCGCTCT | CGGGAACTGA | CCCCAGCTC | CTTCAGCCAT | TTATGAATCC | 300 |
| AGAGGCTTGA | GATTTTTTC | CGCATCCCGG | AGCCCGACCT | GAGAAATTTC | AATGAAAAGG | 360 |
| AAAGTCAATG | GATCGTGGTC | TTGGAAAAGC | TGCTTAGACA | TGTCTGTTTC | CCGGCTCTCT | 420 |
| GAACCCGTGG | CAGAGCTGTA | AGTAAGCGCT | TCACAGTGCG | TGATGAATTG | GATGGCTTCG | 480 |
| GACCCGAGGC | AAAAAAAATA | ATTGTCTCAT | TTTCGTGCTG | ATTTGCTTAA | CTGGTGGGAC | 540 |
| CATGCCAGAA | AGGCTAGCTG | AGACGCTTTT | GGACCTCTGG | ACTCCATTAA | TAATATTATG | 600 |
| GATTACTCTT | CCCTCTTTTG | TGTACATGGC | TCCGATGAAT | CAGGCTCACG | TTTTAACTAC | 660 |
| TGGATCCCCT | TTGGAACTAA | GCAGGCAGAG | TGAAGAAATG | CGGATTTTGA | ACCGCTCCAA | 720 |
| AAGAGGTTGG | GTTTGGAATC | AAATGTTTGT | TCTGGAAGAA | TTTTCTGGAC | CTGAACCGAT | 780 |
| TCTCGTTGGC | CGGTTACACA | CAGATCTGGA | TCCTGGGAGC | AAAAAAATCA | AGTATATCCT | 840 |

```
ATCGGGTGAT  GGAGCCGGCA  CAATCTTTCA  AATAAACGAT  ATAACTGGAG  ACATCCATGC   900
TATCAAAAGA  CTTGACCGAG  AGGAAAAGGC  TGAGTATACG  TTAACAGCTC  AGGCAGTGGA   960
CTGGGAGACA  AACAAACCTC  TCGAGCCTCC  TTCTGAATTT  ATTATTAAGG  TTCAAGACAT  1020
CAACGACAAT  GCCCCGAGT   TTCTCAATGG  ACCTTACCAT  GCTACTGTTC  CAGAGATGTC  1080
CATCTTGGGT  ACATCTGTCA  CTAATGTAAC  GGCCACTGAT  GCTGACGATC  CAGTTATGG   1140
AAACAGTGCA  AAGTTGGTTT  ACAGTATCTT  GGAGGGACAG  CCGTATTTTT  CCATTGAGCC  1200
TGAAACAGCT  ATTATAAAA   CTGCCCTTCC  TAACATGGAC  AGAGAGGCCA  AGGAGGAATA  1260
CCTGGTTGTA  ATTCAAGCCA  AGATATGGG   TGGGCATTCC  GGTGGTCTGT  CTGGAACCAC  1320
GACACTCACA  GTGACGCTTA  CCGATGTGAA  TGACAATCCT  CCAAAATTTG  CTCAAAGTTT  1380
GTATCACTTC  TCAGTACCAG  AAGATGTGGT  CCTTGGCACT  GCAATAGGAA  GGGTTAAAGC  1440
CAATGACCAG  GATATTGGTG  AAAATGCACA  ATCTTCCTAT  GACATCATTG  ATGGAGATGG  1500
GACAGCACTA  TTTGAAATCA  CTTCTGATGC  CCAGGCACAG  GATGGTGTTA  TAAGACTAAG  1560
AAAGCCTCTG  GACTTTGAGA  CCAAAAAATC  CTATACTCTG  AAGGTGGAGG  CAGCCAATAT  1620
CCACATCGAC  CCACGTTTCA  GTGGCAGGGG  ACCCTTTAAA  GATACAGCAA  CAGTCAAAAT  1680
TGTTGTAGAG  GATGCTGATG  AGCCTCCGGT  CTTCTCTTCA  CCGACTTACC  TCCTTGAAGT  1740
TCATGAAAAT  GCTGCCTTGA  ACTCTGTGAT  TGGCCAAGTG  ACAGCTCGTG  ACCCTGATAT  1800
CACTTCCAGC  CCAATAAGGT  TTTCCATTGA  CCGCCACACT  GACTTGGAGA  GACAGTTCAA  1860
CATCAATGCA  GATGATGGGA  AGATAACACT  GGCGACCCCA  CTGGACAGAG  AACTAAGTGT  1920
GTGGCACAAC  ATCTCCATCA  TTGCTACTGA  GATCAGGAAC  CACAGTCAGA  TATCGCGAGT  1980
GCCTGTTGCT  ATTAAAGTGC  TGGATGTCAA  TGACAACGCC  CCTGAATTCG  CGTCCGAATA  2040
TGAGGCATTT  TTATGTGAAA  ATGGAAAACC  CGGCCAAGTC  ATTCAAACAG  TAAGCGCCAT  2100
GGACAAAGAC  GATCCCAAAA  ATGGACATTT  TTTCTTGTAC  AGTCTTCTTC  AGAAATGGT   2160
CAACAACCCA  AATTTCACCA  TCAAGAAAAA  CGAAGATAAT  TCCCTGAGCA  TTCTGGCAAA  2220
ACATAATGGA  TTCAACCGCC  AGAAGCAAGA  AGTCTACCTT  CTGCCTATCG  TGATCAGTGA  2280
CAGTGGGAAC  CCCCCTCTGA  GTAGCACCAG  TACCCTGACC  ATCCGCGTCT  GTGGCTGTAG  2340
CAATGACGGC  GTGGTTCAGT  CGTGCAATGT  CGAAGCTTAT  GTCCTTCCTA  TTGGGCTCAG  2400
TATGGGCGCG  TTAATTGCTA  TATTAGCCTG  CATCATTTTG  CTGCTCGTCA  TTGTGGTTCT  2460
GTTCGTTACC  CTGAGGCGGC  ATAAAAATGA  ACCACTAATA  ATCAAAGATG  ATGAAGACGT  2520
TCGAGAAAAC  ATCATTCGCT  ACGACGACGA  AGGAGGCGGG  GAGGAGGACA  CAGAGGCTTT  2580
TGACATTGCA  ACTTTGCAAA  ACCCAGATGG  AATTAATGGA  TTTTTACCCC  GTAAGGATAT  2640
TAAACCAGAT  TTGCAGTTTA  TGCCAAGGCA  AGGGCTTGCT  CCAGTTCCAA  ATGGTGTTGA  2700
TGTCGATGAA  TTTATAAATG  TAAGGCTTCA  TGAGGCAGAT  AATGACCCCA  CGGCCCCACC  2760
ATATGACTCC  ATTCAGATTT  ATGGCTATGA  AGGCCGAGGG  TCTGTGGCTG  GCTCTCTCAG  2820
CTCGTTGGAG  TCCACCACAT  CAGACTCAGA  CCAGAATTTT  GACTACCTCA  GTGACTGGGG  2880
TCCCCGCTTT  AAGAGACTGG  GCGAACTCTA  CTCTGTTGGT  GAAAGTGACA  AGAAACTTG   2940
ACAGTGGATT  ACATAAATAA  TCAATGGAAC  TGAGCATTCT  GTAATATTCT  AGGGTCACTC  3000
CCCTTAGATG  CAACAAATGT  GGCTATTTGT  TTTAGAGGCA  AGTTTAGCAC  CAATCATCTA  3060
TAAACTCAAC  CACATTTTAA  TGTTGAACCA  AAAAAAATAA  TAAAAAATAA  AAGTATATG   3120
TTAGGAGGTG  AAAAAA                                                       3136
```

( 2 ) INFORMATION FOR SEQ ID NO:42:

( i ) SEQUENCE CHARACTERISTICS:
    ( A ) LENGTH: 799 amino acids
    ( B ) TYPE: amino acid
    ( D ) TOPOLOGY: linear ( i i ) MOLECULE TYPE: protein ( x i ) SEQUENCE DESCRIPTION: SEQ ID NO:42:

```
Met Pro Glu Arg Leu Ala Glu Thr Leu Leu Asp Leu Trp Thr Pro Leu
 1               5                  10                  15

Ile Ile Leu Trp Ile Thr Leu Pro Ser Phe Val Tyr Met Ala Pro Met
                20                  25                  30

Asn Gln Ala His Val Leu Thr Thr Gly Ser Pro Leu Glu Leu Ser Arg
            35                  40                  45

Gln Ser Glu Glu Met Arg Ile Leu Asn Arg Ser Lys Arg Gly Trp Val
     50                  55                  60

Trp Asn Gln Met Phe Val Leu Glu Glu Phe Ser Gly Pro Glu Pro Ile
 65                  70                  75                  80

Leu Val Gly Arg Leu His Thr Asp Leu Asp Pro Gly Ser Lys Lys Ile
                85                  90                  95

Lys Tyr Ile Leu Ser Gly Asp Gly Ala Gly Thr Ile Phe Gln Ile Asn
                100                 105                 110

Asp Ile Thr Gly Asp Ile His Ala Ile Lys Arg Leu Asp Arg Glu Glu
            115                 120                 125

Lys Ala Glu Tyr Thr Leu Thr Ala Gln Ala Val Asp Trp Glu Thr Asn
    130                 135                 140

Lys Pro Leu Glu Pro Pro Ser Glu Phe Ile Ile Lys Val Gln Asp Ile
145                 150                 155                 160

Asn Asp Asn Ala Pro Glu Phe Leu Asn Gly Pro Tyr His Ala Thr Val
                165                 170                 175

Pro Glu Met Ser Ile Leu Gly Thr Ser Val Thr Asn Val Thr Ala Thr
                180                 185                 190

Asp Ala Asp Asp Pro Val Tyr Gly Asn Ser Ala Lys Leu Val Tyr Ser
            195                 200                 205

Ile Leu Glu Gly Gln Pro Tyr Phe Ser Ile Glu Pro Glu Thr Ala Ile
    210                 215                 220

Ile Lys Thr Ala Leu Pro Asn Met Asp Arg Glu Ala Lys Glu Glu Tyr
225                 230                 235                 240

Leu Val Val Ile Gln Ala Lys Asp Met Gly Gly His Ser Gly Gly Leu
                245                 250                 255

Ser Gly Thr Thr Thr Leu Thr Val Thr Leu Thr Asp Val Asn Asp Asn
                260                 265                 270

Pro Pro Lys Phe Ala Gln Ser Leu Tyr His Phe Ser Val Pro Glu Asp
            275                 280                 285

Val Val Leu Gly Thr Ala Ile Gly Arg Val Lys Ala Asn Asp Gln Asp
    290                 295                 300

Ile Gly Glu Asn Ala Gln Ser Ser Tyr Asp Ile Ile Asp Gly Asp Gly
305                 310                 315                 320

Thr Ala Leu Phe Glu Ile Thr Ser Asp Ala Gln Ala Gln Asp Gly Val
                325                 330                 335

Ile Arg Leu Arg Lys Pro Leu Asp Phe Glu Thr Lys Lys Ser Tyr Thr
                340                 345                 350

Leu Lys Val Glu Ala Ala Asn Ile His Ile Asp Pro Arg Phe Ser Gly
            355                 360                 365
```

-continued

| | | | | | | | | | | | | | | |
|---|---|---|---|---|---|---|---|---|---|---|---|---|---|---|
| Arg | Gly 370 | Pro | Phe | Lys | Asp 375 | Thr | Ala | Thr | Val | Lys 380 | Ile | Val | Val | Glu | Asp |
| Ala 385 | Asp | Glu | Pro | Pro | Val 390 | Phe | Ser | Ser | Pro | Thr 395 | Tyr | Leu | Leu | Glu | Val 400 |
| His | Glu | Asn | Ala | Ala 405 | Leu | Asn | Ser | Val | Ile 410 | Gly | Gln | Val | Thr | Ala 415 | Arg |
| Asp | Pro | Asp | Ile 420 | Thr | Ser | Ser | Pro | Ile 425 | Arg | Phe | Ser | Ile | Asp 430 | Arg | His |
| Thr | Asp | Leu 435 | Glu | Arg | Gln | Phe | Asn 440 | Ile | Asn | Ala | Asp | Asp 445 | Gly | Lys | Ile |
| Thr | Leu 450 | Ala | Thr | Pro | Leu | Asp 455 | Arg | Glu | Leu | Ser | Val 460 | Trp | His | Asn | Ile |
| Ser 465 | Ile | Ile | Ala | Thr | Glu 470 | Ile | Arg | Asn | His | Ser 475 | Gln | Ile | Ser | Arg | Val 480 |
| Pro | Val | Ala | Ile | Lys 485 | Val | Leu | Asp | Val | Asn 490 | Asp | Asn | Ala | Pro | Glu 495 | Phe |
| Ala | Ser | Glu | Tyr 500 | Glu | Ala | Phe | Leu | Cys 505 | Glu | Asn | Gly | Lys | Pro 510 | Gly | Gln |
| Val | Ile | Gln 515 | Thr | Val | Ser | Ala | Met 520 | Asp | Lys | Asp | Asp | Pro 525 | Lys | Asn | Gly |
| His | Phe 530 | Phe | Leu | Tyr | Ser | Leu 535 | Leu | Pro | Glu | Met | Val 540 | Asn | Asn | Pro | Asn |
| Phe 545 | Thr | Ile | Lys | Lys | Asn 550 | Glu | Asp | Asn | Ser | Leu 555 | Ser | Ile | Leu | Ala | Lys 560 |
| His | Asn | Gly | Phe | Asn 565 | Arg | Gln | Lys | Gln | Glu 570 | Val | Tyr | Leu | Leu | Pro 575 | Ile |
| Val | Ile | Ser | Asp 580 | Ser | Gly | Asn | Pro | Pro 585 | Leu | Ser | Ser | Thr | Ser 590 | Thr | Leu |
| Thr | Ile | Arg 595 | Val | Cys | Gly | Cys | Ser 600 | Asn | Asp | Gly | Val | Val 605 | Gln | Ser | Cys |
| Asn | Val 610 | Glu | Ala | Tyr | Val | Leu 615 | Pro | Ile | Gly | Leu | Ser 620 | Met | Gly | Ala | Leu |
| Ile 625 | Ala | Ile | Leu | Ala | Cys 630 | Ile | Ile | Leu | Leu | Leu 635 | Val | Ile | Val | Val | Leu 640 |
| Phe | Val | Thr | Leu | Arg 645 | Arg | His | Lys | Asn | Glu 650 | Pro | Leu | Ile | Ile | Lys 655 | Asp |
| Asp | Glu | Asp | Val | Arg 660 | Glu | Asn | Ile | Ile | Arg 665 | Tyr | Asp | Asp | Glu 670 | Gly | Gly |
| Gly | Glu | Glu | Asp 675 | Thr | Glu | Ala | Phe | Asp 680 | Ile | Ala | Thr | Leu 685 | Gln | Asn | Pro |
| Asp | Gly 690 | Ile | Asn | Gly | Phe | Leu 695 | Pro | Arg | Lys | Asp | Ile 700 | Lys | Pro | Asp | Leu |
| Gln 705 | Phe | Met | Pro | Arg | Gln 710 | Gly | Leu | Ala | Pro | Val 715 | Pro | Asn | Gly | Val | Asp 720 |
| Val | Asp | Glu | Phe | Ile 725 | Asn | Val | Arg | Leu | His 730 | Glu | Ala | Asp | Asn | Asp 735 | Pro |
| Thr | Ala | Pro | Pro 740 | Tyr | Asp | Ser | Ile | Gln 745 | Ile | Tyr | Gly | Tyr | Glu 750 | Gly | Arg |
| Gly | Ser | Val 755 | Ala | Gly | Ser | Leu | Ser 760 | Ser | Leu | Glu | Ser | Thr 765 | Thr | Ser | Asp |
| Ser | Asp 770 | Gln | Asn | Phe | Asp | Tyr 775 | Leu | Ser | Asp | Trp | Gly 780 | Pro | Arg | Phe | Lys |
| Arg 785 | Leu | Gly | Glu | Leu | Tyr 790 | Ser | Val | Gly | Glu | Ser 795 | Asp | Lys | Glu | Thr | |

( 2 ) INFORMATION FOR SEQ ID NO:43:

( i ) SEQUENCE CHARACTERISTICS:
        ( A ) LENGTH: 3043 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
GGCACGAGCG  CAAGCCGGGG  AGCGCTCGGC  CCAGAATTAG  TGGATGGATT  TGGAATCTCC      60
CTGCCTCCTC  CAAGCTCCGC  CACTGCCACT  TTAGGCAGAG  ACCTGAGCGT  CAACACGCGA     120
GCCGTACTTT  TAGGCTGCGG  ACACTGAGCC  CAGCGCGCCA  GCTTCGCATC  TCCGCACCAG     180
GCTCCACAGC  TCGGAGAGGC  ATGAACGCGA  TCCGGAGGAG  ACTACCCTGC  GCGCGGGGAT     240
CCGTGGACAT  TAGCCGCTCT  CGGGAACTGA  CCCCCAGCTC  CTTCAGCCAT  TTATGAATCC     300
AGAGGCTTGA  GATTTTTTC   CGCATCCCGG  AGCCCGACCT  GAGAAATTTC  AATGAAAGG      360
AAAGTCAATG  GATCGTGGTC  TTGGAAAAGC  TGCTTAGACA  TGTCTGTTTC  CCGGCTCTCT     420
GAACCCGTGG  CAGAGCTGTA  AGTAAGCGCT  TCACAGTGCG  TGATGAATTG  GATGGCTTCG     480
GACCCGAGGC  AAAAAAAATA  ATTGTCTCAT  TTCGTGCTG   ATTTGCTTAA  CTGGTGGGAC     540
CATGCCAGAA  AGGCTAGCTG  AGACGCTTTT  GGACCTCTGG  ACTCCATTAA  TAATATTATG     600
GATTACTCTT  CCCTCTTTTG  TGTACATGGC  TCCGATGAAT  CAGGCTCACG  TTTTAACTAC     660
TGGATCCCCT  TTGGAACTAA  GCAGGCAGAG  TGAAGAAATG  CGGATTTTGA  ACCGCTCCAA     720
AAGAGGTTGG  GTTTGGAATC  AAATGTTTGT  TCTGGAAGAA  TTTTCTGGAC  CTGAACCGAT     780
TCTCGTTGGC  CGGTTACACA  CAGATCTGGA  TCCTGGGAGC  AAAAAAATCA  AGTATATCCT     840
ATCGGGTGAT  GGAGCCGGCA  CAATCTTTCA  AATAAACGAT  ATAACTGGAG  ACATCCATGC     900
TATCAAAAGA  CTTGACCGAG  AGGAAAAGGC  TGAGTATACG  TTAACAGCTC  AGGCAGTGGA     960
CTGGGAGACA  AACAAACCTC  TCGAGCCTCC  TTCTGAATTT  ATTATTAAGG  TTCAAGACAT    1020
CAACGACAAT  GCCCCCGAGT  TTCTCAATGG  ACCTTACCAT  GCTACTGTTC  AGAGATGTC    1080
CATCTTGGGT  ACATCTGTCA  CTAATGTAAC  GGCCACTGAT  GCTGACGATC  CAGTTTATGG    1140
AAACAGTGCA  AAGTTGGTTT  ACAGTATCTT  GGAGGGACAG  CCGTATTTTT  CCATTGAGCC    1200
TGAAACAGCT  ATTATAAAAA  CTGCCCTTCC  TAACATGGAC  AGAGAGGCCA  AGGAGGAATA    1260
CCTGGTTGTA  ATTCAAGCCA  AGATATGGG   TGGGCATTCC  GGTGGTCTGT  CTGGAACCAC    1320
GACACTCACA  GTGACGCTTA  CCGATGTGAA  TGACAATCCT  CCAAAATTTG  CTCAAAGTTT    1380
GTATCACTTC  TCAGTACCAG  AAGATGTGGT  CCTTGGCACT  GCAATAGGAA  GGGTTAAAGC    1440
CAATGACCAG  GATATTGGTG  AAAATGCACA  ATCTTCCTAT  GACATCATTG  ATGGAGATGG    1500
GACAGCACTA  TTTGAAATCA  CTTCTGATGC  CCAGGCACAG  GATGGTGTTA  TAAGACTAAG    1560
AAAGCCTCTG  GACTTTGAGA  CCAAAAAATC  CTATACTCTG  AAGGTGGAGG  CAGCCAATAT    1620
CCACATCGAC  CCACGTTTCA  GTGGCAGGGG  ACCCTTTAAA  GATACAGCAA  CAGTCAAAAT    1680
TGTTGTAGAG  GATGCTGATG  AGCCTCCGGT  CTTCTCTTCA  CCGACTTACC  TCCTTGAAGT    1740
TCATGAAAAT  GCTGCCTTGA  ACTCTGTGAT  TGGCCAAGTG  ACAGCTCGTG  ACCCTGATAT    1800
CACTTCCAGC  CCAATAAGGT  TTTCCATTGA  CCGCCACACT  GACTTGGAGA  GACAGTTCAA    1860
CATCAATGCA  GATGATGGGA  AGATAACACT  GGCGACCCCA  CTGGACAGAG  AACTAAGTGT    1920
GTGGCACAAC  ATCTCCATCA  TTGCTACTGA  GATCAGGAAC  CACAGTCAGA  TATCGCGAGT    1980
```

-continued

| | | | | | |
|---|---|---|---|---|---|
| GCCTGTTGCT | ATTAAAGTGC | TGGATGTCAA | TGACAACGCC | CCTGAATTCG | CGTCCGAATA | 2040 |
| TGAGGCATTT | TTATGTGAAA | ATGGAAAACC | CGGCCAAGTA | AATATCTCCA | TGTTGTTAAT | 2100 |
| ACTGAATATG | TTTGTATACA | ACTGTTTCCT | AGTTAATTAA | CCTGCATTAC | TTCCTGATTT | 2160 |
| TGCATTGGTT | GGATTTACAA | AGTCACAGGC | AGGAAACTCC | TCCAAGCGGT | AACAGAAGGG | 2220 |
| AATATTTGTC | TTTCTCAGAT | GTTAATTCTC | TTCTAACTTA | GGAACCAATT | GGCTCAGAAA | 2280 |
| GTGTGATGAT | CTGCTCTGCT | CTGACCCCAG | CCAAATCACT | GTCTTAAAAT | ACATCACATA | 2340 |
| TGGGTGATGG | CTGGGGACAG | TCTTACAGTG | CAGAAGGTTG | AAATCGCCAT | CAATTGGCAA | 2400 |
| GAATCTAAAG | AATAGCTCAT | GGGAAGCATG | CATTTTGTT | TTATGTTGAA | AAGAAGATTA | 2460 |
| ATGCACAAAT | GTGGAATGCA | AAAAACACA | GTAGTTTATA | GAAAGCTCTA | TGTAGTGGTA | 2520 |
| CTTATGTCTG | TACACATATT | TGCAAGTTTA | GTAAACATAA | TGTAGACATC | AAATTGTTAG | 2580 |
| ATATGCCCCT | AAGGCATTTC | AATATGTAGA | GGTAAGACTC | CTAAGGCATA | GATGGGGATA | 2640 |
| ATGAAGACAA | AAATAAAGGG | CAGAAAAATG | TATAAAATAG | AACAGACAGA | AATACACTAA | 2700 |
| AGATCTAAAG | ATAGAAGCAG | GAAAGAGGGG | AGGGAGGGAG | GGAGACAGGG | CTGGAAGAAG | 2760 |
| ATAGGGTGGG | AGGGAGGGAA | GGAGAGTCAA | GGCTCAGGGT | GTGGGGGGA | AGGTAAAATG | 2820 |
| CAAAACAAAA | TCTACAGAAA | CCACTATACT | CTGAATGTCA | AAATGCAACT | AACCTATGTA | 2880 |
| AAATCACCCA | ACCACATGTG | TAATAGATTT | ATTTAACGA | GGTGCCGGAG | TACTGTATGT | 2940 |
| TTAAGAAATT | TATCATTTTT | CAACTTCCTA | ATTTATTTCT | GGATGGTGAC | ATTTTAATTT | 3000 |
| AAATAAACAG | CAGCTGACAG | CATGAAAAAA | AAAAAAAAAA | AAA | | 3043 |

( 2 ) INFORMATION FOR SEQ ID NO:44:

( i ) SEQUENCE CHARACTERISTICS:
        ( A ) LENGTH: 532 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

```
Met Pro Glu Arg Leu Ala Glu Thr Leu Leu Asp Leu Trp Thr Pro Leu
 1               5                  10                  15

Ile Ile Leu Trp Ile Thr Leu Pro Ser Phe Val Tyr Met Ala Pro Met
            20                  25                  30

Asn Gln Ala His Val Leu Thr Thr Gly Ser Pro Leu Glu Leu Ser Arg
        35                  40                  45

Gln Ser Glu Glu Met Arg Ile Leu Asn Arg Ser Lys Arg Gly Trp Val
    50                  55                  60

Trp Asn Gln Met Phe Val Leu Glu Glu Phe Ser Gly Pro Glu Pro Ile
65                  70                  75                  80

Leu Val Gly Arg Leu His Thr Asp Leu Asp Pro Gly Ser Lys Lys Ile
                85                  90                  95

Lys Tyr Ile Leu Ser Gly Asp Gly Ala Gly Thr Ile Phe Gln Ile Asn
            100                 105                 110

Asp Ile Thr Gly Asp Ile His Ala Ile Lys Arg Leu Asp Arg Glu Glu
        115                 120                 125

Lys Ala Glu Tyr Thr Leu Thr Ala Gln Ala Val Asp Trp Glu Thr Asn
    130                 135                 140

Lys Pro Leu Glu Pro Pro Ser Glu Phe Ile Ile Lys Val Gln Asp Ile
145                 150                 155                 160

Asn Asp Asn Ala Pro Glu Phe Leu Asn Gly Pro Tyr His Ala Thr Val
                165                 170                 175
```

| | | | | | | | | | | | | | | |
|---|---|---|---|---|---|---|---|---|---|---|---|---|---|---|
|Pro|Glu|Met|Ser 180|Ile|Leu|Gly|Thr|Ser 185|Val|Thr|Asn|Val|Thr 190|Ala|Thr|
|Asp|Ala|Asp 195|Asp|Pro|Val|Tyr|Gly 200|Asn|Ser|Ala|Lys|Leu 205|Val|Tyr|Ser|
|Ile|Leu 210|Glu|Gly|Gln|Pro|Tyr 215|Phe|Ser|Ile|Glu|Pro 220|Glu|Thr|Ala|Ile|
|Ile 225|Lys|Thr|Ala|Leu|Pro 230|Asn|Met|Asp|Arg|Glu 235|Ala|Lys|Glu|Glu|Tyr 240|
|Leu|Val|Val|Ile|Gln 245|Ala|Lys|Asp|Met|Gly 250|Gly|His|Ser|Gly|Gly 255|Leu|
|Ser|Gly|Thr|Thr 260|Thr|Leu|Thr|Val|Thr 265|Leu|Thr|Asp|Val|Asn 270|Asp|Asn|
|Pro|Pro|Lys 275|Phe|Ala|Gln|Ser|Leu 280|Tyr|His|Phe|Ser|Val 285|Pro|Glu|Asp|
|Val|Val 290|Leu|Gly|Thr|Ala|Ile 295|Gly|Arg|Val|Lys|Ala 300|Asn|Asp|Gln|Asp|
|Ile 305|Gly|Glu|Asn|Ala|Gln 310|Ser|Ser|Tyr|Asp|Ile 315|Ile|Asp|Gly|Asp|Gly 320|
|Thr|Ala|Leu|Phe|Glu 325|Ile|Thr|Ser|Asp|Ala 330|Gln|Ala|Gln|Asp|Gly 335|Val|
|Ile|Arg|Leu|Arg 340|Lys|Pro|Leu|Asp|Phe 345|Glu|Thr|Lys|Lys|Ser 350|Tyr|Thr|
|Leu|Lys|Val 355|Glu|Ala|Ala|Asn|Ile 360|His|Ile|Asp|Pro|Arg 365|Phe|Ser|Gly|
|Arg|Gly 370|Pro|Phe|Lys|Asp|Thr 375|Ala|Thr|Val|Lys|Ile 380|Val|Val|Glu|Asp|
|Ala 385|Asp|Glu|Pro|Pro|Val 390|Phe|Ser|Ser|Pro|Thr 395|Tyr|Leu|Leu|Glu|Val 400|
|His|Glu|Asn|Ala|Ala 405|Leu|Asn|Ser|Val|Ile 410|Gly|Gln|Val|Thr|Ala 415|Arg|
|Asp|Pro|Asp|Ile 420|Thr|Ser|Ser|Pro|Ile 425|Arg|Phe|Ser|Ile|Asp 430|Arg|His|
|Thr|Asp|Leu 435|Glu|Arg|Gln|Phe|Asn 440|Ile|Asn|Ala|Asp|Asp 445|Gly|Lys|Ile|
|Thr|Leu|Ala 450|Thr|Pro|Leu|Asp 455|Arg|Glu|Leu|Ser|Val 460|Trp|His|Asn|Ile|
|Ser 465|Ile|Ile|Ala|Thr|Glu 470|Ile|Arg|Asn|His|Ser 475|Gln|Ile|Ser|Arg|Val 480|
|Pro|Val|Ala|Ile|Lys 485|Val|Leu|Asp|Val|Asn 490|Asp|Asn|Ala|Pro|Glu 495|Phe|
|Ala|Ser|Glu|Tyr 500|Glu|Ala|Phe|Leu|Cys 505|Glu|Asn|Gly|Lys|Pro 510|Gly|Gln|
|Val|Asn|Ile|Ser 515|Met|Leu|Leu|Ile|Leu 520|Asn|Met|Phe|Val 525|Tyr|Asn|Cys|
|Phe|Leu|Val|Asn 530| | | | | | | | | | | | |

( 2 ) INFORMATION FOR SEQ ID NO:45:

( i ) SEQUENCE CHARACTERISTICS:
        ( A ) LENGTH: 2490 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

| | | | | | | |
|---|---|---|---|---|---|---|
| GGCACGAGGG | CCAGTTGAGC | CAGAGTCAGA | ATTTGTGATC | AAAATTCACG | ATATCAACGA | 60 |
| CAATGAGCCT | ACATTCCCAG | AAGAAATTTA | TACAGCCAGC | GTTCCTGAAA | TGTCTGTTGT | 120 |
| AGGTACTTCT | GTGGTGCAAG | TCACAGCTAC | AGATGCCGAT | GACCCTTCAT | ATGGAAACAG | 180 |
| CGCCAGAGTC | ATTTACAGCA | TACTTCAAGG | GCAGCCTTAT | TTCTCTGTGG | AACCAGAAAC | 240 |
| AGGTATCATA | AGGACAGCTC | TACCAAACAT | GAACAGAGAG | AACAAGGAAC | AGTACCAGGT | 300 |
| GGTTATTCAA | GCCAAGGACA | TGGGCGGTCA | GATGGGGGGT | CTGTCTGGAA | CCACCACAGT | 360 |
| GAACATCACT | CTCACAGATG | TCAACGACAA | TCCTCCTCGC | TTCCCCCAAA | ACACCATCCA | 420 |
| TCTGCGAGTT | CTTGAATCCT | CTCCAGTTGG | CACAGCTGTG | GAAGTGTAA | AGCCACCGA | 480 |
| TGCTGACACG | GGGAAAAATG | CCGAAGTGGA | TTACCGCATT | ATTGATGGAG | ATGGCACAGA | 540 |
| TATGTTTGAC | ATTATAACTG | AGAAGGACAC | ACAGGAAGGC | ATCATCACTG | TGAAAAAGCC | 600 |
| ACTTGACTAT | GAGAACCGAA | GACTATATAC | TCTGAAGGTG | GAGGCAGAAA | ATACCCATGT | 660 |
| GGATCCACGT | TTTTACTATT | TAGGGCCATT | CAAAGATACA | ACAATTGTAA | AAATCTCCAT | 720 |
| AGAAGACGTG | GATGAGCCTC | CAGTTTTCAG | TCGATCCTCC | TATCTGTTTG | AGGTTCATGA | 780 |
| GGATATTGAA | GTGGGCACAA | TCATCGGTAC | TGTAATGGCA | AGAGACCCAG | ATTCTACTTC | 840 |
| CAGTCCCATC | AGATTTACTT | TAGATCGCCA | TACTGATCTT | GACAGGATCT | TTAACATTCA | 900 |
| TTCTGGAAAC | GGATCACTTT | ATACATCAAA | GCCACTTGAT | CGTGAACTAT | CTCAATGGCA | 960 |
| CAACCTTACC | GTCATAGCTG | CCGAGATCAA | TAATCCTAAA | GAAACAACTC | GTGTGTCTGT | 1020 |
| TTTTGTGAGG | ATTTTGGATG | TTAATGACAA | CGCTCCACAA | TTTGCTGTGT | TTATGACAC | 1080 |
| ATTTGTATGT | GAAAATGCCA | GACCAGGACA | GCTGATACAG | ACAATAAGTG | CAGTTGACAA | 1140 |
| AGATGACCCC | TTAGGTGGAC | AGAAGTTCTT | CTTCAGTTTG | GCTGCTGTGA | ATCCTAACTT | 1200 |
| CACAGTGCAA | GACAATGAAG | ACAACACTGC | CAGAATTTTA | ACCAGAAAGA | ATGGCTTCAA | 1260 |
| CCGTCATGAA | ATAAGCACCT | ACCTACTGCC | GGTAGTGATA | TCTGATAATG | ACTACCCAT | 1320 |
| TCAGAGCAGC | ACTGGCACCC | TGACGATCCG | TGTTTGCGCC | TGTGACAGCC | AGGGCAACAT | 1380 |
| GCAGTCCTGC | AGTGCCGAAG | CCCTGCTCCT | TCCTGCTGGC | CTCAGCACTG | GCGCCTTGAT | 1440 |
| CGCCATTCTT | CTCTGCATCA | TCATTCTGCT | GGTTATAGTA | GTCCTCTTTG | CAGCCCTGAA | 1500 |
| AAGGCAACGG | AAGAAAGAGC | CTCTGATTTT | ATCCAAAGAA | GACATCAGAG | ACAACATTGT | 1560 |
| GAGCTATAAC | GACGAAGGTG | GCGGAGAGGA | GGACACCCAA | CCCTTTGATA | TTGGAACCCT | 1620 |
| GAGGAATCCT | GCAGCTATCG | AGGAGAAAAA | GCTGCGGCGA | GATATCATTC | CTGAAACGTT | 1680 |
| ATTTATACCG | CGGCGGACTC | CTACGGCCCC | GGATAACACG | GATGTCCGGG | ATTTCATTAA | 1740 |
| TGAGCGCCTC | AAAGAGCACG | ACTTGGACCC | CACTGCGCCT | CCCTACGACT | CGCTGGCTAC | 1800 |
| CTATGCCTAT | GAAGGAAACG | ACTCTGTTGC | TGAATCTCTG | AGCTCCTTAG | AATCAGGTAC | 1860 |
| CACTGAAGGA | GACCAAAACT | ACGATTACCT | TCGAGAATGG | GGGCCTCGGT | TAATAAACT | 1920 |
| AGCAGAAATG | TACGGTGGTG | GTGAGAGCGA | CAAAGACGCT | TAGCCTGGCC | CCTGAGCTCT | 1980 |
| GTTCAACGAG | ATACGTAACT | TTGCAGACAT | TGTCTCCACT | TCACAATATT | TGATATTCAG | 2040 |
| GAGAAAAAAT | TCCTGCCACT | CAGCACAAGT | TTCCCACCTA | TTTCTTAATT | TGTTCATTAA | 2100 |
| TTATATTAAT | TCCTTCCTGT | AGAATGTCTC | ATGGGATATA | TACGACATTT | TATTTAATCA | 2160 |
| CTTCCAAGAG | CCAAAGCTAT | GGAAATTCAA | TGTTGCCCAT | CTTAGTAAAT | AAAAGAAACC | 2220 |
| CGAGCAGGAT | AGTTCTCCCT | TAAGCAACCT | CACGAACAAG | TCGCTTCTGT | TAGATACACG | 2280 |
| TCTTGCCCTT | GCAAATGAAG | CTTTGAAAAG | ACGAAGAAAA | CATTTAAGAT | GTATCCTGTT | 2340 |

```
CTGTACATTA AGTTTAAAAA AAAAAGTCCA TGTGGTGTTA GTAGGTGTGA TATGCAGCCT    2400

GGTATACGAG CATTCGTGCA ATTTCATTTC ATCAAATTCT ATCTGCTAAT GTTTATATT     2460

TATATTTTTG TATTTATTTT TTAAAAAAAA                                     2490
```

( 2 ) INFORMATION FOR SEQ ID NO:46:

( i ) SEQUENCE CHARACTERISTICS:
        ( A ) LENGTH: 653 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Ala  Arg  Gly  Pro  Val  Glu  Pro  Glu  Ser  Glu  Phe  Val  Ile  Lys  Ile  His
 1              5                    10                       15

Asp  Ile  Asn  Asp  Asn  Glu  Pro  Thr  Phe  Pro  Glu  Glu  Ile  Tyr  Thr  Ala
            20                   25                       30

Ser  Val  Pro  Glu  Met  Ser  Val  Val  Gly  Thr  Ser  Val  Val  Gln  Val  Thr
            35                        40                       45

Ala  Thr  Asp  Ala  Asp  Asp  Pro  Ser  Tyr  Gly  Asn  Ser  Ala  Arg  Val  Ile
 50                        55                       60

Tyr  Ser  Ile  Leu  Gln  Gly  Gln  Pro  Tyr  Phe  Ser  Val  Glu  Pro  Glu  Thr
 65                        70                       75                       80

Gly  Ile  Ile  Arg  Thr  Ala  Leu  Pro  Asn  Met  Asn  Arg  Glu  Asn  Lys  Glu
                      85                        90                       95

Gln  Tyr  Gln  Val  Val  Ile  Gln  Ala  Lys  Asp  Met  Gly  Gly  Gln  Met  Gly
                 100                      105                      110

Gly  Leu  Ser  Gly  Thr  Thr  Thr  Val  Asn  Ile  Thr  Leu  Thr  Asp  Val  Asn
                 115                      120                      125

Asp  Asn  Pro  Pro  Arg  Phe  Pro  Gln  Asn  Thr  Ile  His  Leu  Arg  Val  Leu
            130                      135                      140

Glu  Ser  Ser  Pro  Val  Gly  Thr  Ala  Val  Gly  Ser  Val  Lys  Ala  Thr  Asp
145                      150                      155                      160

Ala  Asp  Thr  Gly  Lys  Asn  Ala  Glu  Val  Asp  Tyr  Arg  Ile  Ile  Asp  Gly
                      165                      170                      175

Asp  Gly  Thr  Asp  Met  Phe  Asp  Ile  Ile  Thr  Glu  Lys  Asp  Thr  Gln  Glu
                 180                      185                      190

Gly  Ile  Ile  Thr  Val  Lys  Lys  Pro  Leu  Asp  Tyr  Glu  Asn  Arg  Arg  Leu
                 195                      200                      205

Tyr  Thr  Leu  Lys  Val  Glu  Ala  Glu  Asn  Thr  His  Val  Asp  Pro  Arg  Phe
210                      215                      220

Tyr  Tyr  Leu  Gly  Pro  Phe  Lys  Asp  Thr  Thr  Ile  Val  Lys  Ile  Ser  Ile
225                      230                      235                      240

Glu  Asp  Val  Asp  Glu  Pro  Pro  Val  Phe  Ser  Arg  Ser  Ser  Tyr  Leu  Phe
                      245                      250                      255

Glu  Val  His  Glu  Asp  Ile  Glu  Val  Gly  Thr  Ile  Ile  Gly  Thr  Val  Met
                 260                      265                      270

Ala  Arg  Asp  Pro  Asp  Ser  Thr  Ser  Ser  Pro  Ile  Arg  Phe  Thr  Leu  Asp
                 275                      280                      285

Arg  His  Thr  Asp  Leu  Asp  Arg  Ile  Phe  Asn  Ile  His  Ser  Gly  Asn  Gly
            290                      295                      300

Ser  Leu  Tyr  Thr  Ser  Lys  Pro  Leu  Asp  Arg  Glu  Leu  Ser  Gln  Trp  His
305                      310                      315                      320

Asn  Leu  Thr  Val  Ile  Ala  Ala  Glu  Ile  Asn  Asn  Pro  Lys  Glu  Thr  Thr
```

|     |     |     |     |     | 325 |     |     |     |     |     |     |     | 330 |     |     |     |     |     | 335 |
|-----|-----|-----|-----|-----|-----|-----|-----|-----|-----|-----|-----|-----|-----|-----|-----|-----|-----|-----|-----|

Arg Val Ser Val Phe Val Arg Ile Leu Asp Val Asn Asp Asn Ala Pro
                    340                         345             350

Gln Phe Ala Val Phe Tyr Asp Thr Phe Val Cys Glu Asn Ala Arg Pro
            355                 360             365

Gly Gln Leu Ile Gln Thr Ile Ser Ala Val Asp Lys Asp Asp Pro Leu
        370             375             380

Gly Gly Gln Lys Phe Phe Phe Ser Leu Ala Ala Val Asn Pro Asn Phe
385                 390                 395                 400

Thr Val Gln Asp Asn Glu Asp Asn Thr Ala Arg Ile Leu Thr Arg Lys
                405                 410              415

Asn Gly Phe Asn Arg His Glu Ile Ser Thr Tyr Leu Leu Pro Val Val
            420             425                 430

Ile Ser Asp Asn Asp Tyr Pro Ile Gln Ser Ser Thr Gly Thr Leu Thr
        435             440                 445

Ile Arg Val Cys Ala Cys Asp Ser Gln Gly Asn Met Gln Ser Cys Ser
    450             455                 460

Ala Glu Ala Leu Leu Leu Pro Ala Gly Leu Ser Thr Gly Ala Leu Ile
465             470                 475                 480

Ala Ile Leu Leu Cys Ile Ile Ile Leu Leu Val Ile Val Val Leu Phe
            485                 490                 495

Ala Ala Leu Lys Arg Gln Arg Lys Lys Glu Pro Leu Ile Leu Ser Lys
            500             505                 510

Glu Asp Ile Arg Asp Asn Ile Val Ser Tyr Asn Asp Glu Gly Gly Gly
        515             520             525

Glu Glu Asp Thr Gln Pro Phe Asp Ile Gly Thr Leu Arg Asn Pro Ala
530                 535                 540

Ala Ile Glu Glu Lys Lys Leu Arg Arg Asp Ile Ile Pro Glu Thr Leu
545             550                 555                 560

Phe Ile Pro Arg Arg Thr Pro Thr Ala Pro Asp Asn Thr Asp Val Arg
            565             570                 575

Asp Phe Ile Asn Glu Arg Leu Lys Glu His Asp Leu Asp Pro Thr Ala
            580             585                 590

Pro Pro Tyr Asp Ser Leu Ala Thr Tyr Ala Tyr Glu Gly Asn Asp Ser
        595                 600             605

Val Ala Glu Ser Leu Ser Ser Leu Glu Ser Gly Thr Thr Glu Gly Asp
    610             615                 620

Gln Asn Tyr Asp Tyr Leu Arg Glu Trp Gly Pro Arg Phe Asn Lys Leu
625             630                 635                 640

Ala Glu Met Tyr Gly Gly Gly Glu Ser Asp Lys Asp Ala
                645                 650

(2) INFORMATION FOR SEQ ID NO:47:

(i) SEQUENCE CHARACTERISTICS:
        (A) LENGTH: 3048 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

```
CGCCGGCGGG GAAGATGACC GCGGGCGCCG GCGTGCTCCT TCTGCTGCTC TCGCTCTCCG      60

GCGCGCTCCG GGCCCATAAT GAGGATCTTA CAACTAGAGA GACCTGCAAG GCTGGGTTCT     120

CTGAAGATGA TTCACGGCA TTAATCTCCC AAAATATTCT AGAAGGGGAA AAGCTACTTC      180
```

| | | | | | |
|---|---|---|---|---|---|
| AAGTCAAGTT | CAGCAGCTGT | GTGGGGACCA | AGGGGACACA | ATATGAGACC | AACAGCATGG | 240
| ACTTCAAAGT | TGGGGCAGAT | GGGACAGTCT | TCGCCACCCG | GGAGCTGCAG | GTCCCCTCCG | 300
| AGCAGGTGGC | GTTCACGGTG | ACTGCATGGG | ACAGCCAGAC | AGCAGAGAAA | TGGGACGCCG | 360
| TGGTGCGGTT | GCTGGTGGCC | CAGACCTCGT | CCCCGCACTC | TGGACACAAG | CCGCAGAAAG | 420
| GAAAGAAGGT | CGTGGCTCTG | GACCCCTCTC | CGCCTCCGAA | GGACACCCTG | CTGCCGTGGC | 480
| CCCAGCACCA | GAACGCCAAC | GGGCTGAGGC | GGCGCAAACG | GGACTGGGTC | ATCCCACCCA | 540
| TCAACGTGCC | CGAGAACTCG | CGCGGGCCCT | TCCCGCAGCA | GCTCGTGAGG | ATCCGGTCCG | 600
| ACAAAGACAA | TGACATCCCC | ATCCGGTACA | GCATCACGGG | AGTGGGTGCC | GACCAGCCCC | 660
| CCATGGAGGT | CTTCAGCATT | AACTCCATGT | CCGGCCGGAT | GTACGTCACA | AGGCCCATGG | 720
| ACCGGGAGGA | GCACGCCTCT | TACCACCTCC | GAGCCCACGC | TGTGGACATG | AATGGCAACA | 780
| AGGTGGAGAA | CCCCATCGAC | CTGTACATCT | ACGTCATCGA | CATGAATGAC | AACCACCCTG | 840
| AGTTCATCAA | CCAGGTCTAC | AACTGCTCCG | TGGACGAGGG | CTCCAAGCCA | GGCACCTACG | 900
| TGATGACCAT | CACGGCCAAC | GATGCTGACG | ACAGCACCAC | GGCCAACGGG | ATGGTGCGGT | 960
| ACCGGATCGT | GACCCAGACC | CCACAGAGCC | CGTCCCAGAA | TATGTTCACC | ATCAACAGCG | 1020
| AGACTGGAGA | TATCGTCACA | GTGGCGGCTG | GCTGGGACCG | AGAGAAAGTT | CAGCAGTACA | 1080
| CAGTCATCGT | TCAGGCCACA | GATATGGAAG | GAAATCTCAA | CTATGGCCTC | TCAAACACAG | 1140
| CCACAGCCAT | CATCACGGTG | ACAGATGTGA | ATGACAACCC | GTCAGAATTT | ACCGCCAGCA | 1200
| CGTTTGCAGG | GGAGGTCCCC | GAAAACAGCG | TGGAGACCGT | GGTCGCAAAC | CTCACGGTGA | 1260
| TGGACCGAGA | TCAGCCCCAC | TCTCCAAACT | GGAATGCCGT | TTACCGCATC | ATCAGTGGGG | 1320
| ATCCATCCGG | GCACTTCAGC | GTCCGCACAG | ACCCCGTAAC | CAACGAGGGC | ATGGTCACCG | 1380
| TGGTGAAGGC | AGTCGACTAC | GAGCTCAACA | GAGCTTTCAT | GCTGACAGTG | ATGGTGTCCA | 1440
| ACCAGGCGCC | CCTGGCCAGC | GGAATCCAGA | TGTCCTTCCA | GTCCACGGCA | GGGGTGACCA | 1500
| TCTCCATCAT | GGACATCAAC | GAGGCTCCCT | ACTTCCCCTC | AAACCACAAG | CTGATCCGCC | 1560
| TGGAGGAGGG | CGTGCCCCCC | GGCACCGTGC | TGACCACGTT | TTCAGCTGTG | GACCCTGACC | 1620
| GGTTCATGCA | GCAGGCTGTG | AGATACTCAA | AGCTGTCAGA | CCCAGCGAGC | TGGCTGCACA | 1680
| TCAATGCCAC | CAACGGCCAG | ATCACCACGG | TGGCAGTGCT | GGACCGTGAG | TCCCTCTACA | 1740
| CCAAAAACAA | CGTCTACGAG | GCCACCTTCC | TGGCAGCTGA | CAATGGGATA | CCCCGGCCA | 1800
| GCGGCACCGG | GACCCTCCAG | ATCTATCTCA | TTGACATCAA | CGACAACGCC | CCTGAGCTGC | 1860
| TGCCCAAGGA | GGCGCAGATC | TGCGAGAGGC | CCAACCTGAA | CGCCATCAAC | ATCACGGCGG | 1920
| CCGACGCTGA | CGTGCACCCC | AACATCGGCC | CCTACGTCTT | CGAGCTGCCC | TTTGTCCCGG | 1980
| CGGCCGTGCG | GAAGAACTGG | ACCATCACCC | GCCTGAACGG | TGACTATGCC | CAACTCAGCT | 2040
| TGCGCATCCT | GTACCTGGAG | GCCGGGATGT | ATGACGTCCC | CATCATCGTC | ACAGACTCTG | 2100
| GAAACCCTCC | CCTGTCCAAC | ACGTCCATCA | TCAAAGTCAA | GGTGTGCCCA | TGTGATGACA | 2160
| ACGGGGACTG | CACCACCATT | GGCGCAGTGG | CAGCGGCTGG | TCTGGGCACC | GGTGCCATCG | 2220
| TGGCCATCCT | CATCTGCATC | CTCATCCTGC | TGACCATGGT | CCTGCTGTTT | GTCATGTGGA | 2280
| TGAAGCGGCG | AGAGAAGGAG | CGCCACACGA | AGCAGCTGCT | CATTGACCCC | GAGGACGACG | 2340
| TCCGCGAAAA | GATCCTCAAG | TATGACGAGG | AAGGCGGTGG | CGAGGAGGAC | CAGGACTACG | 2400
| ACCTCAGCCA | GCTGCAGCAG | CCGGAAGCCA | TGGGGCACGT | GCCAAGCAAA | GCCCCTGGCG | 2460
| TGCGTCGCGT | GGATGAGCGG | CCGGTGGGCC | CTGAGCCCCA | GTACCCGATC | AGGCCCATGG | 2520
| TGCCGCACCC | AGGCGACATC | GGTGACTTCA | TCAATGAGGG | ACTCCGCGCT | GCTGACAACG | 2580

```
ACCCCACGGC ACCCCCCTAT GACTCCCTGC TGGTCTTCGA CTACGAGGGG AGCGGCTCCA      2640

CCGCAGGCTC CGTCAGCTCC CTGAACTCAT CCAGTTCCGG GGACCAAGAC TACGATTACC      2700

TCAACGACTG GGCCCCAGA TTCAAGAAGC TGGCGGACAT GTATGGAGGT GGTGAAGAGG       2760

ATTGACTGAC CTCGCATCTT CGGACCGAAG TGAGAGCCGT GCTCGGACGC CGGAGGAGCA      2820

GGACTGAGCA GAGGCGGCCG GTCTTCCCGA CTCCCTGCGG CTGTGTCCTT AGTGCTGTTA      2880

GGAGGCCCCC CAATCCCCAC GTTGAGCTGT CTAGCATGAG CACCCACCCC CACAGCGCCC      2940

TGCACCCGGC CGCTGCCCAG CACCGCGCTG GCTGGCACTG AAGGACAGCA GAGGCACTC       3000

TGTCTTCACT TGAATTTCCT AGAACAGAAG CACTGTTTTT AAAAAAAG                   3048
```

( 2 ) INFORMATION FOR SEQ ID NO:48:

( i ) SEQUENCE CHARACTERISTICS:
      ( A ) LENGTH: 916 amino acids
      ( B ) TYPE: amino acid
      ( D ) TOPOLOGY: linear ( i i ) MOLECULE TYPE: protein ( x i ) SEQUENCE DESCRIPTION: SEQ ID NO:48:

```
Met Thr Ala Gly Ala Gly Val Leu Leu Leu Leu Leu Ser Leu Ser Gly
 1               5                  10                  15

Ala Leu Arg Ala His Asn Glu Asp Leu Thr Thr Arg Glu Thr Cys Lys
            20                  25                  30

Ala Gly Phe Ser Glu Asp Asp Tyr Thr Ala Leu Ile Ser Gln Asn Ile
        35                  40                  45

Leu Glu Gly Glu Lys Leu Leu Gln Val Lys Phe Ser Ser Cys Val Gly
 50                  55                  60

Thr Lys Gly Thr Gln Tyr Glu Thr Asn Ser Met Asp Phe Leu Val Gly
65                  70                  75                  80

Ala Asp Gly Thr Val Phe Ala Thr Arg Glu Leu Gln Val Pro Ser Glu
            85                  90                  95

Gln Val Ala Phe Thr Val Thr Ala Trp Asp Ser Gln Thr Ala Glu Lys
        100                 105                 110

Trp Asp Ala Val Val Arg Leu Leu Val Ala Gln Thr Ser Ser Pro His
        115                 120                 125

Ser Gly His Lys Pro Gln Lys Gly Lys Lys Val Val Ala Leu Asp Pro
130                 135                 140

Ser Pro Pro Lys Asp Thr Leu Leu Pro Trp Pro Gln His Gln Asn
145                 150                 155                 160

Ala Asn Gly Leu Arg Arg Arg Lys Arg Asp Trp Val Ile Pro Pro Ile
            165                 170                 175

Asn Val Pro Glu Asn Ser Arg Gly Pro Phe Pro Gln Gln Leu Val Arg
        180                 185                 190

Ile Arg Ser Asp Lys Asp Asn Asp Ile Pro Ile Arg Tyr Ser Ile Thr
        195                 200                 205

Gly Val Gly Ala Asp Gln Pro Pro Met Glu Val Phe Ser Ile Asn Ser
210                 215                 220

Met Ser Gly Arg Met Tyr Val Thr Arg Pro Met Asp Arg Glu Glu His
225                 230                 235                 240

Ala Ser Tyr His Leu Arg Ala His Ala Val Asp Met Asn Gly Asn Lys
            245                 250                 255

Val Glu Asn Pro Ile Asp Leu Tyr Ile Tyr Val Ile Asp Met Asn Asp
        260                 265                 270
```

| | | | | | | | | | | | | | | |
|---|---|---|---|---|---|---|---|---|---|---|---|---|---|---|
| Asn | His | Pro 275 | Glu | Phe | Ile | Asn 280 | Gln | Val | Tyr | Asn | Cys 285 | Ser | Val | Asp | Glu |
| Gly | Ser 290 | Lys | Pro | Gly | Thr 295 | Tyr | Val | Met | Thr | Ile 300 | Thr | Ala | Asn | Asp | Ala |
| Asp 305 | Asp | Ser | Thr | Thr | Ala 310 | Asn | Gly | Met | Val | Arg 315 | Tyr | Arg | Ile | Val | Thr 320 |
| Gln | Thr | Pro | Gln | Ser 325 | Pro | Ser | Gln | Asn | Met 330 | Phe | Thr | Ile | Asn | Ser 335 | Glu |
| Thr | Gly | Asp | Ile 340 | Val | Thr | Val | Ala | Ala 345 | Gly | Trp | Asp | Arg | Glu 350 | Lys | Val |
| Gln | Gln | Tyr 355 | Thr | Val | Ile | Val | Gln 360 | Ala | Thr | Asp | Met | Glu 365 | Gly | Asn | Leu |
| Asn | Tyr 370 | Gly | Leu | Ser | Asn | Thr 375 | Ala | Thr | Ala | Ile | Ile 380 | Thr | Val | Thr | Asp |
| Val 385 | Asn | Asp | Asn | Pro | Ser 390 | Glu | Phe | Thr | Ala | Ser 395 | Thr | Phe | Ala | Gly | Glu 400 |
| Val | Pro | Glu | Asn | Ser 405 | Val | Glu | Thr | Val | Val 410 | Ala | Asn | Leu | Thr | Val 415 | Met |
| Asp | Arg | Asp | Gln 420 | Pro | His | Ser | Pro | Asn 425 | Trp | Asn | Ala | Val | Tyr 430 | Arg | Ile |
| Ile | Ser | Gly 435 | Asp | Pro | Ser | Gly | His 440 | Phe | Ser | Val | Arg | Thr 445 | Asp | Pro | Val |
| Thr | Asn 450 | Glu | Gly | Met | Val | Thr 455 | Val | Val | Lys | Ala | Val 460 | Asp | Tyr | Glu | Leu |
| Asn 465 | Arg | Ala | Phe | Met | Leu 470 | Thr | Val | Met | Val | Ser 475 | Asn | Gln | Ala | Pro | Leu 480 |
| Ala | Ser | Gly | Ile | Gln 485 | Met | Ser | Phe | Gln | Ser 490 | Thr | Ala | Gly | Val | Thr 495 | Ile |
| Ser | Ile | Met | Asp 500 | Ile | Asn | Glu | Ala | Pro 505 | Tyr | Phe | Pro | Ser | Asn 510 | His | Lys |
| Leu | Ile | Arg 515 | Leu | Glu | Glu | Gly | Val 520 | Pro | Pro | Gly | Thr | Val 525 | Leu | Thr | Thr |
| Phe | Ser 530 | Ala | Val | Asp | Pro | Asp 535 | Arg | Phe | Met | Gln | Gln 540 | Ala | Val | Arg | Tyr |
| Ser 545 | Lys | Leu | Ser | Asp | Pro 550 | Ala | Ser | Trp | Leu | His 555 | Ile | Asn | Ala | Thr | Asn 560 |
| Gly | Gln | Ile | Thr | Thr 565 | Val | Ala | Val | Leu | Asp 570 | Arg | Glu | Ser | Leu | Tyr 575 | Thr |
| Lys | Asn | Asn | Val 580 | Tyr | Glu | Ala | Thr | Phe 585 | Leu | Ala | Ala | Asp | Asn 590 | Gly | Ile |
| Pro | Pro | Ala 595 | Ser | Gly | Thr | Gly | Thr 600 | Leu | Gln | Ile | Tyr | Leu 605 | Ile | Asp | Ile |
| Asn | Asp 610 | Asn | Ala | Pro | Glu | Leu 615 | Leu | Pro | Lys | Glu | Ala 620 | Gln | Ile | Cys | Glu |
| Arg 625 | Pro | Asn | Leu | Asn | Ala 630 | Ile | Asn | Ile | Thr | Ala 635 | Ala | Asp | Ala | Asp 640 |
| His | Pro | Asn | Ile | Gly 645 | Pro | Tyr | Val | Phe | Glu 650 | Leu | Pro | Phe | Val | Pro 655 | Ala |
| Ala | Val | Arg | Lys 660 | Asn | Trp | Thr | Ile | Thr 665 | Arg | Leu | Asn | Gly | Asp 670 | Tyr | Ala |
| Gln | Leu | Ser 675 | Leu | Arg | Ile | Leu | Tyr 680 | Leu | Glu | Ala | Gly | Met 685 | Tyr | Asp | Val |
| Pro | Ile 690 | Ile | Val | Thr | Asp | Ser 695 | Gly | Asn | Pro | Pro | Leu 700 | Ser | Asn | Thr | Ser |

| | | | | | | | | | | | | | | |
|---|---|---|---|---|---|---|---|---|---|---|---|---|---|---|
| Ile | Ile | Lys | Val | Lys | Val | Cys | Pro | Cys | Asp | Asp | Asn | Gly | Asp | Cys | Thr |
| 705 | | | | 710 | | | | 715 | | | | | | 720 |
| Thr | Ile | Gly | Ala | Val | Ala | Ala | Ala | Gly | Leu | Gly | Thr | Gly | Ala | Ile | Val |
| | | | 725 | | | | | 730 | | | | | 735 | | |
| Ala | Ile | Leu | Ile | Cys | Ile | Leu | Ile | Leu | Thr | Met | Val | Leu | Leu | Phe | |
| | | | 740 | | | | 745 | | | | | 750 | | | |
| Val | Met | Trp | Met | Lys | Arg | Arg | Glu | Lys | Glu | Arg | His | Thr | Lys | Gln | Leu |
| | | | 755 | | | | 760 | | | | 765 | | | | |
| Leu | Ile | Asp | Pro | Glu | Asp | Val | Arg | Glu | Lys | Ile | Leu | Lys | Tyr | Asp | |
| | 770 | | | | 775 | | | | 780 | | | | | | |
| Glu | Glu | Gly | Gly | Gly | Glu | Glu | Asp | Gln | Asp | Tyr | Asp | Leu | Ser | Gln | Leu |
| 785 | | | | | 790 | | | | 795 | | | | | 800 | |
| Gln | Gln | Pro | Glu | Ala | Met | Gly | His | Val | Pro | Ser | Lys | Ala | Pro | Gly | Val |
| | | | 805 | | | | 810 | | | | | 815 | | | |
| Arg | Arg | Val | Asp | Glu | Arg | Pro | Val | Gly | Pro | Glu | Pro | Gln | Tyr | Pro | Ile |
| | | 820 | | | | 825 | | | | 830 | | | | | |
| Arg | Pro | Met | Val | Pro | His | Pro | Gly | Asp | Ile | Gly | Asp | Phe | Ile | Asn | Glu |
| | 835 | | | | | 840 | | | | | 845 | | | | |
| Gly | Leu | Arg | Ala | Ala | Asp | Asn | Asp | Pro | Thr | Ala | Pro | Pro | Tyr | Asp | Ser |
| 850 | | | | | 855 | | | | 860 | | | | | | |
| Leu | Leu | Val | Phe | Asp | Tyr | Glu | Gly | Ser | Gly | Ser | Thr | Ala | Gly | Ser | Val |
| 865 | | | | 870 | | | | | 875 | | | | | 880 | |
| Ser | Ser | Leu | Asn | Ser | Ser | Ser | Gly | Asp | Gln | Asp | Tyr | Asp | Tyr | Leu | |
| | | | 885 | | | | | 890 | | | | 895 | | | |
| Asn | Asp | Trp | Gly | Pro | Arg | Phe | Lys | Lys | Leu | Ala | Asp | Met | Tyr | Gly | Gly |
| | | 900 | | | | | 905 | | | | 910 | | | | |
| Gly | Glu | Glu | Asp | | | | | | | | | | | | |
| | | 915 | | | | | | | | | | | | | |

( 2 ) INFORMATION FOR SEQ ID NO:49:

( i ) SEQUENCE CHARACTERISTICS:
        ( A ) LENGTH: 3164 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

```
CTCCACTCAC GCTCAGCCCT GGACGGACAG GCAGTCCAAC GGAACAGAAA CATCCCTCAG      60
CCCACAGGCA CGATCTGTTC CTCCTGGGAA GATGCAGAGG CTATGATGCT CCTCGCCACA     120
TCGGGCGCCT GCCTGGGCCT GCTGGCAGTG GCAGCAGTGG CAGCAGCAGG TGCTAACCCT     180
GCCCAACGGG ACACCCACAG CCTGCTGCCC ACCCACCGGC GCCAAAGAG  AGATTGGATT     240
TGGAACCAGA TGCACATTGA TGAAGAGAAA AACACCTCAC TTCCCCATCA TGTAGGCAAG     300
ATCAAGTCAA GCGTGAGTCG CAAGAATGCC AAGTACCTGC TCAAAGGAGA ATATGTGGGC     360
AAGGTCTTCC GGGTCGATGC AGAGACAGGA GACGTGTTCG CCATTGAGAG GCTGGACCGG     420
GAGAATATCT CAGAGTACCA CCTCACTGCT GTCATTGTGG ACAAGGACAC TGGCGAAAAC     480
CTGGAGACTC CTTCCAGCTT CACCATCAAA GTTCATGACG TGAACGACAA CTGGCCTGTG     540
TTCACGCATC GGTTGTTCAA TGCGTCCGTG CCTGAGTCGT CGGCTGTGGG GACCTCAGTC     600
ATCTCTGTGA CAGCAGTGGA TGCAGACGAC CCCACTGTGG GAGACCACGC CTCTGTCATG     660
TACCAAATCC TGAAGGGGAA AGAGTATTTT GCCATCGATA ATTCTGGACG TATTATCACA     720
```

```
ATAACGAAAA GCTTGGACCG AGAGAAGCAG GCCAGGTATG AGATCGTGGT GGAAGCGCGA    780
GATGCCCAGG GCCTCCGGGG GGACTCGGGC ACGGCCACCG TGCTGGTCAC TCTGCAAGAC    840
ATCAATGACA ACTTCCCCTT CTTCACCCAG ACCAAGTACA CATTTGTCGT GCCTGAAGAC    900
ACCCGTGTGG GCACCTCTGT GGGCTCTCTG TTTGTTGAGG ACCCAGATGA GCCCCAGAAC    960
CGGATGACCA AGTACAGCAT CTTGCGGGGC GACTACCAGG ACGCTTTCAC CATTGAGACA   1020
AACCCCGCCC ACAACGAGGG CATCATCAAG CCCATGAAGC CTCTGGATTA TGAATACATC   1080
CAGCAATACA GCTTCATAGT CGAGGCCACA GACCCCACCA TCGACCTCCG ATACATGAGC   1140
CCTCCCGCGG GAAACAGAGC CCAGGTCATT ATCAACATCA CAGATGTGGA CGAGCCCCCC   1200
ATTTTCCAGC AGCCTTTCTA CCACTTCCAG CTGAAGGAAA ACCAGAAGAA GCCTCTGATT   1260
GGCACAGTGC TGGCCATGGA CCCTGATGCG GCTAGGCATA GCATTGGATA CTCCATCCGC   1320
AGGACCAGTG ACAAGGGCCA GTTCTTCCGA GTCACAAAAA AGGGGACAT TTACAATGAG    1380
AAAGAACTGG ACAGAGAAGT CTACCCCTGG TATAACCTGA CTGTGGAGGC CAAAGAACTG   1440
GATTCCACTG GAACCCCCAC AGGAAAAGAA TCCATTGTGC AAGTCCACAT TGAAGTTTTG   1500
GATGAGAATG ACAATGCCCC GGAGTTTGCC AAGCCCTACC AGCCCAAAGT GTGTGAGAAC   1560
GCTGTCCATG GCCAGCTGGT CCTGCAGATC TCCGCAATAG ACAAGGACAT AACACCACGA   1620
AACGTGAAGT TCAAATTCAT CTTGAATACT GAGAACAACT TTACCCTCAC GGATAATCAC   1680
GATAACACGG CCAACATCAC AGTCAAGTAT GGGCAGTTTG ACCGGGAGCA TACCAAGGTC   1740
CACTTCCTAC CCGTGGTCAT CTCAGACAAT GGGATGCCAA GTCGCACGGG CACCAGCACG   1800
CTGACCGTGG CCGTGTGCAA GTGCAACGAG CAGGGCGAGT TCACCTTCTG CGAGGATATG   1860
GCCGCCCAGG TGGGCGTGAG CATCCAGGCA GTGGTAGCCA TCTTACTCTG CATCCTCACC   1920
ATCACAGTGA TCACCCTGCT CATCTTCCTG CGGCGGCGGC TCCGGAAGCA GGCCCGCGCG   1980
CACGGCAAGA GCGTGCCGGA GATCCACGAG CAGCTGGTCA CCTACGACGA GGAGGGCGGC   2040
GGCGAGATGG ACACCACCAG CTACGATGTG TCGGTGCTCA ACTCGGTGCG CCGCGGCGGG   2100
GCCAAGCCCC GCGGCCCCGC GCTGGACGCC CGGCCTTCCC TCTATGCGCA GGTGCAGAAG   2160
CCACCGAGGC ACGCGCCTGG GGCACACGGA GGGCCGGGG AGATGGCAGC CATGATCGAG    2220
GTGAAGAAGG ACGAGGCGGA CCACGACGGC GACGGCCCCC CCTACGACAC GCTGCACATC   2280
TACGGCTACG AGGGCTCCGA GTCCATAGCC GAGTCCCTCA GCTCCCTGGG CACCGACTCA   2340
TCCGACTCTG ACGTGGATTA CGACTTCCTT AACGACTGGG GACCCAGGTT TAAGATGCTG   2400
GCTGAGCTGT ACGGCTCGGA CCCCCGGGAG GAGCTGCTGT ATTAGGCGGC CGAGGTCACT   2460
CTGGGCCTGG GGACCCAAAC CCCTGCAGCC CAGGCCAGT CAGACTCCAG GCACCACAGC    2520
CTCCAAAAAT GGCAGTGACT CCCCAGCCCA GCACCCCTTC CTCGTGGGTC CAGAGACCT    2580
CATCAGCCTT GGGATAGCAA ACTCCAGGTT CCTGAAATAT CCAGGAATAT ATGTCAGTGA   2640
TGACTATTCT CAAATGCTGG CAAATCCAGG CTGGTGTTCT GTCTGGGCTC AGACATCCAC   2700
ATAACCCTGT CACCCACAGA CCGCCGTCTA ACTCAAAGAC TTCCTCTGGC TCCCCAAGGC   2760
TGCAAAGCAA AACAGACTGT GTTAACTGC TGCAGGGTCT TTTTCTAGGG TCCCTGAACG    2820
CCCTGGTAAG GCTGGTGAGG TCCTGGTGCC TATCTGCCTG GAGGCAAAGG CCTGGACAGC   2880
TTGACTTGTG GGCAGGATT CTCTGCAGCC CATTCCCAAG GGAGACTGAC CATCATGCCC    2940
TCTCTCGGGA GCCCTAGCCC TGCTCCAACT CCATACTCCA CTCCAAGTGC CCCACCACTC   3000
CCCAACCCCT CTCCAGGCCT GTCAAGAGGG AGGAAGGGGC CCCATGGCAG CTCCTGACCT   3060
TGGGTCCTGA AGTGACCTCA CTGGCCTGCC ATGCCAGTAA CTGTGCTGTA CTGAGCACTG   3120
```

AACCACATTC AGGGAAATGG CTTATTAAAC TTTGAAGCAA CTGT 3164

( 2 ) INFORMATION FOR SEQ ID NO:50:

( i ) SEQUENCE CHARACTERISTICS:
        ( A ) LENGTH: 780 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

```
Met Met Leu Leu Ala Thr Ser Gly Ala Cys Leu Gly Leu Leu Ala Val
 1               5                  10                  15
Ala Ala Val Ala Ala Ala Gly Ala Asn Pro Ala Gln Arg Asp Thr His
             20                  25                  30
Ser Leu Leu Pro Thr His Arg Arg Gln Lys Arg Asp Trp Ile Trp Asn
         35                  40                  45
Gln Met His Ile Asp Glu Glu Lys Asn Thr Ser Leu Pro His His Val
     50                  55                  60
Gly Lys Ile Lys Ser Ser Val Ser Arg Lys Asn Ala Lys Tyr Leu Leu
 65                  70                  75                  80
Lys Gly Glu Tyr Val Gly Lys Val Phe Arg Val Asp Ala Glu Thr Gly
                 85                  90                  95
Asp Val Phe Ala Ile Glu Arg Leu Asp Arg Glu Asn Ile Ser Glu Tyr
             100                 105                 110
His Leu Thr Ala Val Ile Val Asp Lys Asp Thr Gly Glu Asn Leu Glu
         115                 120                 125
Thr Pro Ser Ser Phe Thr Ile Lys Val His Asp Val Asn Asp Asn Trp
    130                 135                 140
Pro Val Phe Thr His Arg Leu Phe Asn Ala Ser Val Pro Glu Ser Ser
145                 150                 155                 160
Ala Val Gly Thr Ser Val Ile Ser Val Thr Ala Val Asp Ala Asp Asp
                165                 170                 175
Pro Thr Val Gly Asp His Ala Ser Val Met Tyr Gln Ile Leu Lys Gly
            180                 185                 190
Lys Glu Tyr Phe Ala Ile Asp Asn Ser Gly Arg Ile Ile Thr Ile Thr
        195                 200                 205
Lys Ser Leu Asp Arg Glu Lys Gln Ala Arg Tyr Glu Ile Val Val Glu
    210                 215                 220
Ala Arg Asp Ala Gln Gly Leu Arg Gly Asp Ser Gly Thr Ala Thr Val
225                 230                 235                 240
Leu Val Thr Leu Gln Asp Ile Asn Asp Asn Phe Pro Phe Phe Thr Gln
                245                 250                 255
Thr Lys Tyr Thr Phe Val Val Pro Glu Asp Thr Arg Val Gly Thr Ser
            260                 265                 270
Val Gly Ser Leu Phe Val Glu Asp Pro Asp Glu Pro Gln Asn Arg Met
        275                 280                 285
Thr Lys Tyr Ser Ile Leu Arg Gly Asp Tyr Gln Asp Ala Phe Thr Ile
    290                 295                 300
Glu Thr Asn Pro Ala His Asn Glu Gly Ile Ile Lys Pro Met Lys Pro
305                 310                 315                 320
Leu Asp Tyr Glu Tyr Ile Gln Gln Tyr Ser Phe Ile Val Glu Ala Thr
                325                 330                 335
Asp Pro Thr Ile Asp Leu Arg Tyr Met Ser Pro Pro Ala Gly Asn Arg
            340                 345                 350
```

-continued

```
Ala Gln Val Ile Ile Asn Ile Thr Asp Val Asp Glu Pro Pro Ile Phe
        355                 360                 365
Gln Gln Pro Phe Tyr His Phe Gln Leu Lys Glu Asn Gln Lys Lys Pro
370                 375                 380
Leu Ile Gly Thr Val Leu Ala Met Asp Pro Asp Ala Ala Arg His Ser
385                 390                 395                 400
Ile Gly Tyr Ser Ile Arg Arg Thr Ser Asp Lys Gly Gln Phe Phe Arg
                405                 410                 415
Val Thr Lys Lys Gly Asp Ile Tyr Asn Glu Lys Glu Leu Asp Arg Glu
                420                 425                 430
Val Tyr Pro Trp Tyr Asn Leu Thr Val Glu Ala Lys Glu Leu Asp Ser
            435                 440                 445
Thr Gly Thr Pro Thr Gly Lys Glu Ser Ile Val Gln Val His Ile Glu
    450                 455                 460
Val Leu Asp Glu Asn Asp Asn Ala Pro Glu Phe Ala Lys Pro Tyr Gln
465                 470                 475                 480
Pro Lys Val Cys Glu Asn Ala Val His Gly Gln Leu Val Leu Gln Ile
                485                 490                 495
Ser Ala Ile Asp Lys Asp Ile Thr Pro Arg Asn Val Lys Phe Lys Phe
                500                 505                 510
Ile Leu Asn Thr Glu Asn Asn Phe Thr Leu Thr Asp Asn His Asp Asn
                515                 520                 525
Thr Ala Asn Ile Thr Val Lys Tyr Gly Gln Phe Asp Arg Glu His Thr
    530                 535                 540
Lys Val His Phe Leu Pro Val Val Ile Ser Asp Asn Gly Met Pro Ser
545                 550                 555                 560
Arg Thr Gly Thr Ser Thr Leu Thr Val Ala Val Cys Lys Cys Asn Glu
                565                 570                 575
Gln Gly Glu Phe Thr Phe Cys Glu Asp Met Ala Ala Gln Val Gly Val
                580                 585                 590
Ser Ile Gln Ala Val Val Ala Ile Leu Leu Cys Ile Leu Thr Ile Thr
        595                 600                 605
Val Ile Thr Leu Leu Ile Phe Leu Arg Arg Arg Leu Arg Leu Gln Ala
    610                 615                 620
Arg Ala His Gly Lys Ser Val Pro Glu Ile His Glu Gln Leu Val Thr
625                 630                 635                 640
Tyr Asp Glu Glu Gly Gly Gly Glu Met Asp Thr Thr Ser Tyr Asp Val
                645                 650                 655
Ser Val Leu Asn Ser Val Arg Arg Gly Gly Ala Lys Pro Pro Arg Pro
            660                 665                 670
Ala Leu Asp Ala Arg Pro Ser Leu Tyr Ala Gln Val Gln Lys Pro Pro
        675                 680                 685
Arg His Ala Pro Gly Ala His Gly Gly Pro Gly Glu Met Ala Ala Met
    690                 695                 700
Ile Glu Val Lys Lys Asp Glu Ala Asp His Asp Gly Asp Gly Pro Pro
705                 710                 715                 720
Tyr Asp Thr Leu His Ile Tyr Gly Tyr Glu Gly Ser Glu Ser Ile Ala
                725                 730                 735
Glu Ser Leu Ser Ser Leu Gly Thr Asp Ser Ser Asp Ser Asp Val Asp
            740                 745                 750
Tyr Asp Phe Leu Asn Asp Trp Gly Pro Arg Phe Lys Met Leu Ala Glu
            755                 760                 765
Leu Tyr Gly Ser Asp Pro Arg Glu Glu Leu Leu Tyr
770                 775                 780
```

( 2 ) INFORMATION FOR SEQ ID NO:51:

( i ) SEQUENCE CHARACTERISTICS:
        ( A ) LENGTH: 1369 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

```
TGTAGATGAG CCACCTGTCT TCAGCAAACT GGCCTACATC TTACAAATAA GAGAAGATGC      60
TCAGATAAAC ACCACAATAG GCTCCGTCAC AGCCCAAGAT CCAGATGCTG CCAGGAATCC     120
TGTCAAGTAC TCTATAGATC GACACACAGA TATGGACAGA ATATTCAACA TTGATTCTGG     180
AAATGGTTCG ATTTTTACAT CGAAACTTCT TGACCGAGAA ACACTGCTAT GGCACAACAT     240
TACAGTGATA GCAACAGAGA TCAATAATCC AAAGCAAAGT AGTCGAGTAC CTCTATATAT     300
TAAAGTTCTA GATGTCAATG ACAACGCCCC AGAATTTGCT GAGTTCTATG AAACTTTTGT     360
CTGTGAAAAA GCAAAGGCAG ATCAGTTGAT TCAGACCTTG CATGCTGTTA GCAAGGATGA     420
CCCTTATAGT GGGCACCAAT TTTCGTTTTC CTTGGCCCCT GAAGCAGCCA GTGGCTCAAA     480
CTTTACCATT CAAGACAACA AAGACAACAC GGCGGGAATC TTAACTCGGA AAAATGGCTA     540
TAATAGACAC GAGATGAGCA CCTATCTCTT GCCTGTGGTC ATTTCAGACA ACGACTACCC     600
AGTTCAAAGC AGCACTGGGA CAGTGACTGT CCGGGTCTGT GCATGTGACC ACCACGGGAA     660
CATGCAATCC TGCCATGCGG AGGCGCTCAT CCACCCCACG GGACTGAGCA CGGGGGCTCT     720
GGTTGCCATC CTTCTGTGCA TCGTGATCCT ACTAGTGACA GTGGTGCTGT TTGCAGCTCT     780
GAGGCGGCAG CGAAAAAAAG AGCCTTTGAT CATTTCCAAA GAGGACATCA GAGATAACAT     840
TGTCAGTTAC AACGACGAAG GTGGTGGAGA GGAGGACACC CAGGCTTTTG ATATCGGCAC     900
CCTGAGGAAT CCTGAAGCCA TAGAGGACAA CAAATTACGA AGGGACATTG TGCCCGAAGC     960
CCTTTTCCTA CCCCGACGGA CTCCAACAGC TCGCGACAAC ACCGATGTCA GAGATTTCAT    1020
TAACCAAAGG TTAAAGGAAA ATGACACGGA CCCCACTGCC CCGCCATACG ACTCCCTGGC    1080
CACTTACGCC TATGAAGGCA CTGGCTCCGT GGCGGATTCC CTGAGCTCGC TGGAGTCAGT    1140
GACCACGGAT GCAGATCAAG ACTATGATTA CCTTTAGTGA CTGGGACCTC GATTCAAAAA    1200
GCTTGCAGAT ATGTATGGAG GAGTGGACAG TGACAAAGAC TCCTAATCTG TTGCCTTTTT    1260
CATTTTCCAA TACGACACTG AAATATGTGA AGTGGCTATT TCTTTATATT TATCCACTAC    1320
TCCGTGAAGG CTTCTCTGTT CTACCCGTTC CAAAAGCCAA TGGCTGCAG               1369
```

( 2 ) INFORMATION FOR SEQ ID NO:52:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:52:

```
Val Asp Glu Pro Pro Val Phe Ser Lys Leu Ala Tyr Ile Leu Gln Ile
 1               5                  10                  15

Arg Glu Asp Ala Gln Ile Asn Thr Thr Ile Gly Ser Val Thr Ala Gln
                20                  25                  30

Asp Pro Asp Ala Ala Arg Asn Pro Val Lys Tyr Ser Ile Lys Arg His
            35                  40                  45
```

```
Thr  Asp  Met  Asp  Arg  Ile  Phe  Asn  Ile  Asp  Ser  Gly  Asn  Gly  Ser  Ile
     50                       55                      60

Phe  Thr  Ser  Lys  Leu  Leu  Lys  Arg  Glu  Thr  Leu  Leu  Trp  His  Asn  Ile
65                       70                      75                           80

Thr  Val  Ile  Ala  Thr  Glu  Ile  Asn  Asn  Pro  Lys  Gln  Ser  Ser  Arg  Val
                    85                       90                           95

Pro  Leu  Tyr  Ile  Lys  Val  Leu  Asp  Val  Asn  Asp  Asn  Ala  Pro  Glu  Phe
               100                      105                      110

Ala  Glu  Phe  Tyr  Glu  Thr  Phe  Val  Cys  Glu  Lys  Ala  Lys  Ala  Asp  Gln
          115                      120                      125

Leu  Ile  Gln  Thr  Leu  His  Ala  Val  Asp  Lys  Asp  Asp  Pro  Tyr  Ser  Gly
          130                      135                      140

His  Gln  Phe  Ser  Phe  Ser  Leu  Ala  Pro  Glu  Ala  Ala  Ser  Gly  Ser  Asn
145                           150                      155                     160

Phe  Thr  Ile  Gln  Asp  Asn  Lys  Asp  Asn  Thr  Ala  Gly  Ile  Leu  Thr  Arg
                    165                      170                      175

Lys  Asn  Gly  Tyr  Asn  Arg  His  Glu  Met  Ser  Thr  Tyr  Leu  Leu  Pro  Val
               180                      185                      190

Val  Ile  Ser  Asp  Asn  Asp  Tyr  Pro  Val  Gln  Ser  Ser  Thr  Gly  Thr  Val
               195                      200                      205

Thr  Val  Arg  Val  Cys  Ala  Cys  Asp  His  His  Gly  Asn  Met  Gln  Ser  Cys
     210                      215                      220

His  Ala  Glu  Ala  Leu  Ile  His  Pro  Thr  Gly  Leu  Ser  Thr  Gly  Ala  Leu
225                           230                      235                     240

Val  Ala  Ile  Leu  Leu  Cys  Ile  Val  Ile  Leu  Leu  Val  Thr  Val  Val  Leu
               245                      250                      255

Phe  Ala  Ala  Leu  Arg  Arg  Gln  Arg  Lys  Lys  Glu  Pro  Leu  Ile  Ile  Ser
               260                      265                      270

Lys  Glu  Asp  Ile  Arg  Asp  Asn  Ile  Val  Ser  Tyr  Asn  Asp  Glu  Gly  Gly
          275                      280                      285

Gly  Glu  Glu  Asp  Thr  Gln  Ala  Phe  Asp  Ile  Gly  Thr  Leu  Arg  Asn  Pro
     290                      295                      300

Glu  Ala  Ile  Glu  Asp  Asn  Lys  Leu  Arg  Arg  Asp  Ile  Val  Pro  Glu  Ala
305                           310                      315                     320

Leu  Phe  Leu  Pro  Arg  Arg  Thr  Pro  Thr  Ala  Arg  Asp  Asn  Thr  Asp  Val
               325                      330                      335

Arg  Asp  Phe  Ile  Asn  Gln  Arg  Leu  Lys  Glu  Asn  Asp  Thr  Asp  Pro  Thr
          340                      345                      350

Ala  Pro  Pro  Tyr  Asp  Ser  Leu  Ala  Thr  Tyr  Ala  Tyr  Glu  Gly  Thr  Gly
          355                      360                      365

Ser  Val  Ala  Asp  Ser  Leu  Ser  Ser  Leu  Glu  Ser  Val  Thr  Thr  Asp  Ala
     370                      375                      380

Asp  Gln  Asp  Tyr  Asp  Tyr  Leu  Ser  Asp  Trp  Gly  Pro  Arg  Phe  Lys  Lys
385                      390                      395                          400

Leu  Ala  Asp  Met  Tyr  Gly  Gly  Val  Asp  Ser  Asp  Lys  Asp  Ser
                    405                      410
```

( 2 ) INFORMATION FOR SEQ ID NO:53:

( i ) SEQUENCE CHARACTERISTICS:
      ( A ) LENGTH: 2550 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:53:

| | | | | | | |
|---|---|---|---|---|---|---|
| CAGGAAATGC | TCTTGGATCT | CTGGACTCCA | TTAATAATAT | TATGGATTAC | TCTTCCCCCT | 60 |
| TGCATTTACA | TGGCTCCGAT | GAATCAGTCT | CAAGTTTTAA | TGAGTGGATC | CCCTTTGGAA | 120 |
| CTAAACAGTC | TGGGTGAAGA | ACAGCGAATT | TTGAACCGCT | CCAAAAGAGG | CTGGGTTTGG | 180 |
| AATCAAATGT | TTGTCCTGGA | AGAGTTTTCT | GGACCTGAAC | CGATTCTTGT | TGGCCGGCTA | 240 |
| CACACAGACC | TGGATCCTGG | GAGCAAAAAA | ATCAAGTATA | TCCTATCAGG | TGATGGAGCT | 300 |
| GGGACCATAT | TTCAAATAAA | TGATGTAACT | GGAGATATCC | ATGCTATAAA | AAGACTTGAC | 360 |
| CGGGAGGAAA | AGGCTGAGTA | TACCCTAACA | GCTCAAGCAG | TGGACTGGGA | GACAAGCAAA | 420 |
| CCTCTGGAGC | CTCCTTCTGA | ATTTATTATT | AAAGTTCAAG | ACATCAATGA | CAATGCACCA | 480 |
| GAGTTTCTTA | ATGGACCCTA | TCATGCTACT | GTGCCAGAAA | TGTCCATTTT | GGGTACATCT | 540 |
| GTCACTAACG | TCACTGCGAC | CGACGCTGAT | GACCCAGTTT | ATGGAAACAG | TGCAAAGTTG | 600 |
| GTTTATAGTA | TATTGGAAGG | GCAGCCTTAT | TTTTCCATTG | AGCCTGAAAC | AGCTATTATA | 660 |
| AAAACTGCCC | TTCCCAACAT | GGACAGAGAA | GCCAAGGAGG | AGTACCTGGT | TGTTATCCAA | 720 |
| GCCAAAGATA | TGGGTGGACA | CTCTGGTGGC | CTGTCTGGGA | CCACGACACT | TACAGTGACT | 780 |
| CTTACTGATG | TTAATGACAA | TCCTCCAAAA | TTTGCACAGA | GCCTGTATCA | CTTCTCAGTA | 840 |
| CCGGAAGATG | TGGTTCTTGG | CACTGCAATA | GGAAGGGTGA | AGGCCAATGA | TCAGGATATT | 900 |
| GGTGAAAATG | CACAGTCATC | ATATGATATC | ATCGATGGAG | ATGGAACAGC | ACTTTTTGAA | 960 |
| ATCACTTCTG | ATGCCCAGGC | CCAGGATGGC | ATTATAAGGC | TAAGAAAACC | TCTGGACTTT | 1020 |
| GAGACCAAAA | AATCCTATAC | GCTAAAGGAT | GAGGCAGCCA | ATGTCCATAT | TGACCCACGC | 1080 |
| TTCAGTGGCA | GGGGGCCCTT | TAAAGACACG | GCGACAGTCA | AATCGTGGT | TGAAGATGCT | 1140 |
| GATGAGCCTC | CGGTCTTCTC | TTCACCGACT | TACCTACTTG | AAGTTCATGA | AAATGCTGCT | 1200 |
| CTAAACTCCG | TGATTGGGCA | AGTGACTGCT | CGTGACCCTG | ATATCACTTC | CAGTCCTATA | 1260 |
| AGGTTTTCCA | TCGACCGGCA | CACTGACCTG | GAGAGGCAGT | TCAACATTAA | TGCAGACGAT | 1320 |
| GGGAAGATAA | CGCTGGCAAC | ACCACTTGAC | AGAGAATTAA | GTGTATGGCA | CAACATAACA | 1380 |
| ATCATTGCTA | CTGAAATTAG | GAACCACAGT | CAGATATCAC | GAGTACCTGT | TGCTATTAAA | 1440 |
| GTGCTGGATG | TCAATGACAA | CGCCCCTGAA | TTCGCATCCG | AATATGAGGC | ATTTTATGT | 1500 |
| GAAAATGGAA | AACCCGGCCA | AGTCATTCAA | ACTGTTAGCG | CCATGGACAA | AGATGATCCC | 1560 |
| AAAAACGGAC | ATTATTTCTT | ATACAGTCTC | CTTCCAGAAA | TGGTCAACAA | TCCGAATTTC | 1620 |
| ACCATCAAGA | AAATGAAGA | TAATTCCCTC | AGTATTTTGG | CAAAGCATAA | TGGATTCAAC | 1680 |
| CGCCAGAAGC | AAGAAGTCTA | TCTTTTACCA | ATCATAATCA | GTGATAGTGG | AAATCCTCCA | 1740 |
| CTGAGCAGCA | CTAGCACCTT | GACAATCAGG | GTCTGTGGCT | GCAGCAATGA | CGGTGTCGTC | 1800 |
| CAGTCTTGCA | ATGTCGAAGC | TTATGTCCTT | CCAATTGGAC | TCAGTATGGG | CGCCTTAATT | 1860 |
| GCCATATTAG | CATGCATCAT | TTTGCTGTTA | GTCATCGTGG | TGCTGTTTGT | AACTCTACGG | 1920 |
| CGGCATCAAA | AAAATGAACC | ATTAATTATC | AAAGATGATG | AAGACGTTCG | AGAAACATC | 1980 |
| ATTCGCTACG | ATGATGAAGG | AGGAGGGGAG | GAGGACACAG | AGGCTTTTGA | CATTGCAACT | 2040 |
| TTACAAAATC | CAGATGGAAT | TAATGGATTT | TTACCCCGTA | AGGATATTAA | ACCAGATTTG | 2100 |
| CAGTTTATGC | CAAGGCAAGG | GCTTGCTCCA | GTTCCAAATG | GTGTTGATGT | CGATGAATTT | 2160 |
| ATAAATGTAA | GGCTGCATGA | GGCAGATAAT | GATCCCACAG | CCCCGCCATA | TGACTCCATT | 2220 |
| CAAATATATG | GCTATGAAGG | CCGAGGGTCA | GTGGCTGGCT | CCCTCAGCTC | CTTGGAGTCC | 2280 |
| ACCACATCAG | ACTCAGACCA | GAATTTTGAC | TACCTCAGTG | ACTGGGGTCC | CCGCTTTAAG | 2340 |

```
AGACTGGGCG AACTCTACTC TGTTGGTGAA AGTGACAAAG AAACTTGACA GTGGATTATA      2400

AATAAATCAC TGGAACTGAG CATTCTGTAA TATTCTAGGG TCACTCCCCT TAGATACAAC      2460

CAATGTGGCT ATTTGTTTAG AGGCAAGTTT AGCACCAGTC ATCTATAACT CAACCACATT      2520

TAATGTTGAC AAAAAGATAA TAAATAAAAA                                      2550
```

( 2 ) INFORMATION FOR SEQ ID NO:54:

( i ) SEQUENCE CHARACTERISTICS:
        ( A ) LENGTH: 793 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

```
Met Leu Leu Asp Leu Trp Thr Pro Leu Ile Ile Leu Trp Ile Thr Leu
 1               5                  10                  15

Pro Pro Cys Ile Tyr Met Ala Pro Met Asn Gln Ser Gln Val Leu Met
            20                  25                  30

Ser Gly Ser Pro Leu Gln Leu Asn Ser Leu Gly Glu Glu Gln Arg Ile
        35                  40                  45

Leu Asn Arg Ser Lys Arg Gly Trp Val Trp Asn Gln Met Phe Val Leu
    50                  55                  60

Glu Glu Phe Ser Gly Pro Glu Pro Ile Leu Val Gly Arg Leu His Thr
65                  70                  75                  80

Asp Leu Asp Pro Gly Ser Lys Lys Ile Lys Tyr Ile Leu Ser Gly Asp
                85                  90                  95

Gly Ala Gly Thr Ile Phe Gln Ile Asn Asp Val Thr Gly Asp Ile His
            100                 105                 110

Ala Ile Lys Arg Leu Asp Arg Glu Glu Lys Ala Glu Tyr Thr Leu Thr
        115                 120                 125

Ala Gln Ala Val Asp Trp Glu Thr Ser Lys Pro Leu Glu Pro Pro Ser
    130                 135                 140

Glu Phe Ile Ile Lys Val Gln Asp Ile Asn Asp Asn Ala Pro Glu Phe
145                 150                 155                 160

Leu Asn Gly Pro Tyr His Ala Thr Val Pro Glu Met Ser Ile Leu Gly
                165                 170                 175

Thr Ser Val Thr Asn Val Thr Ala Thr Asp Ala Asp Asp Pro Val Tyr
            180                 185                 190

Gly Asn Ser Ala Lys Leu Val Tyr Ser Ile Leu Glu Gly Gln Pro Tyr
        195                 200                 205

Phe Ser Ile Glu Pro Glu Thr Ala Ile Ile Lys Thr Ala Leu Pro Asn
    210                 215                 220

Met Asp Arg Glu Ala Lys Glu Glu Tyr Leu Val Val Ile Gln Ala Lys
225                 230                 235                 240

Asp Met Gly Gly His Ser Gly Gly Leu Ser Gly Thr Thr Thr Leu Thr
                245                 250                 255

Val Thr Leu Thr Asp Val Asn Asp Asn Pro Pro Lys Phe Ala Gln Ser
            260                 265                 270

Leu Tyr His Phe Ser Val Pro Glu Asp Val Val Leu Gly Thr Ala Ile
        275                 280                 285

Gly Arg Val Lys Ala Asn Asp Gln Asp Ile Gly Glu Asn Ala Gln Ser
    290                 295                 300

Ser Tyr Asp Ile Ile Asp Gly Asp Gly Thr Ala Leu Phe Glu Ile Thr
305                 310                 315                 320
```

```
Ser Asp Ala Gln Ala Gln Asp Gly Ile Ile Arg Leu Arg Lys Pro Leu
            325                 330                 335
Asp Phe Glu Thr Lys Lys Ser Tyr Thr Leu Lys Asp Glu Ala Ala Asn
            340                 345                 350
Val His Ile Asp Pro Arg Phe Ser Gly Arg Gly Pro Phe Lys Asp Thr
            355                 360                 365
Ala Thr Val Lys Ile Val Val Glu Asp Ala Asp Glu Pro Pro Val Phe
370                 375                 380
Ser Ser Pro Thr Tyr Leu Leu Glu Val His Glu Asn Ala Ala Leu Asn
385                 390                 395                 400
Ser Val Ile Gly Gln Val Thr Ala Arg Asp Pro Asp Ile Thr Ser Ser
            405                 410                 415
Pro Ile Arg Phe Ser Ile Asp Arg His Thr Asp Leu Glu Arg Gln Phe
            420                 425                 430
Asn Ile Asn Ala Asp Asp Gly Lys Ile Thr Leu Ala Thr Pro Leu Asp
            435                 440                 445
Arg Glu Leu Ser Val Trp His Asn Ile Thr Ile Ile Ala Thr Glu Ile
450                 455                 460
Arg Asn His Ser Gln Ile Ser Arg Val Pro Val Ala Ile Lys Val Leu
465                 470                 475                 480
Asp Val Asn Asp Asn Ala Pro Glu Phe Ala Ser Glu Tyr Glu Ala Phe
                485                 490                 495
Leu Cys Glu Asn Gly Lys Pro Gly Gln Val Ile Gln Thr Val Ser Ala
            500                 505                 510
Met Asp Lys Asp Asp Pro Lys Asn Gly His Tyr Phe Leu Tyr Ser Leu
        515                 520                 525
Leu Pro Glu Met Val Asn Asn Pro Asn Phe Thr Ile Lys Lys Asn Glu
    530                 535                 540
Asp Asn Ser Leu Ser Ile Leu Ala Lys His Asn Gly Phe Asn Arg Gln
545                 550                 555                 560
Lys Gln Glu Val Tyr Leu Leu Pro Ile Ile Ile Ser Asp Ser Gly Asn
                565                 570                 575
Pro Pro Leu Ser Ser Thr Ser Thr Leu Thr Ile Arg Val Cys Gly Cys
            580                 585                 590
Ser Asn Asp Gly Val Val Gln Ser Cys Asn Val Glu Ala Tyr Val Leu
        595                 600                 605
Pro Ile Gly Leu Ser Met Gly Ala Leu Ile Ala Ile Leu Ala Cys Ile
    610                 615                 620
Ile Leu Leu Leu Val Ile Val Val Leu Phe Val Thr Leu Arg Arg His
625                 630                 635                 640
Gln Lys Asn Glu Pro Leu Ile Ile Lys Asp Asp Glu Asp Val Arg Glu
                645                 650                 655
Asn Ile Ile Arg Tyr Asp Asp Glu Gly Gly Gly Glu Glu Asp Thr Glu
            660                 665                 670
Ala Phe Asp Ile Ala Thr Leu Gln Asn Pro Asp Gly Ile Asn Gly Phe
        675                 680                 685
Leu Pro Arg Lys Asp Ile Lys Pro Asp Leu Gln Phe Met Pro Arg Gln
    690                 695                 700
Gly Leu Ala Pro Val Pro Asn Gly Val Asp Val Asp Glu Phe Ile Asn
705                 710                 715                 720
Val Arg Leu His Glu Ala Asp Asn Asp Pro Thr Ala Pro Pro Tyr Asp
                725                 730                 735
Ser Ile Gln Ile Tyr Gly Tyr Glu Gly Arg Gly Ser Val Ala Gly Ser
```

| | 740 | | | | 745 | | | | | 750 | | |
|---|---|---|---|---|---|---|---|---|---|---|---|---|
| Leu | Ser | Ser | Leu | Glu | Ser | Thr | Thr | Ser | Asp | Ser | Asp | Gln | Asn | Phe | Asp |
| | | 755 | | | | 760 | | | | 765 | | |

| Tyr | Leu | Ser | Asp | Trp | Gly | Pro | Arg | Phe | Lys | Arg | Leu | Gly | Glu | Leu | Tyr |
|---|---|---|---|---|---|---|---|---|---|---|---|---|---|---|---|
| | 770 | | | | 775 | | | | | 780 | | |

| Ser | Val | Gly | Glu | Ser | Asp | Lys | Glu | Thr |
|---|---|---|---|---|---|---|---|---|
| 785 | | | | | 790 | | | |

( 2 ) INFORMATION FOR SEQ ID NO:55:

( i ) SEQUENCE CHARACTERISTICS:
        ( A ) LENGTH: 730 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..730

( x i ) SEQUENCE DESCRIPTION: SEQ ID NO:55:

| G | AAT | TCG | AGC | TCG | GTA | CCC | GGG | GAT | CCT | CTA | GAG | TCG | ACC | TGC | AGT | 46 |
|---|---|---|---|---|---|---|---|---|---|---|---|---|---|---|---|---|
| | Asn | Ser | Ser | Ser | Val | Pro | Gly | Asp | Pro | Leu | Glu | Ser | Thr | Cys | Ser | |
| | 1 | | | | 5 | | | | | 10 | | | | | 15 | |

| GCT | GAA | GCC | CTG | CTC | CTC | CCT | GCC | GGC | CTC | AGC | ACT | GGG | GCC | TTG | ATC | 94 |
|---|---|---|---|---|---|---|---|---|---|---|---|---|---|---|---|---|
| Ala | Glu | Ala | Leu | Leu | Leu | Pro | Ala | Gly | Leu | Ser | Thr | Gly | Ala | Leu | Ile | |
| | | | | 20 | | | | | 25 | | | | | 30 | | |

| GCC | ATC | CTC | CTC | TGC | ATC | ATC | ATT | CTA | CTG | GTT | ATA | GTA | GTA | CTG | TTT | 142 |
|---|---|---|---|---|---|---|---|---|---|---|---|---|---|---|---|---|
| Ala | Ile | Leu | Leu | Cys | Ile | Ile | Ile | Leu | Leu | Val | Ile | Val | Val | Leu | Phe | |
| | | | 35 | | | | | 40 | | | | | 45 | | | |

| GCA | GCT | CTG | AAA | AGA | CAG | CGA | AAA | AAA | GAG | CCT | CTG | ATC | TTG | TCA | AAA | 190 |
|---|---|---|---|---|---|---|---|---|---|---|---|---|---|---|---|---|
| Ala | Ala | Leu | Lys | Arg | Gln | Arg | Lys | Lys | Glu | Pro | Leu | Ile | Leu | Ser | Lys | |
| | | 50 | | | | | 55 | | | | | 60 | | | | |

| GAA | GAT | ATC | AGA | GAC | AAC | ATT | GTG | AGC | TAT | AAC | GAT | GAG | GGT | GGT | GGA | 238 |
|---|---|---|---|---|---|---|---|---|---|---|---|---|---|---|---|---|
| Glu | Asp | Ile | Arg | Asp | Asn | Ile | Val | Ser | Tyr | Asn | Asp | Glu | Gly | Gly | Gly | |
| | 65 | | | | | 70 | | | | | 75 | | | | | |

| GAG | GAG | GAC | ACC | CAG | GCC | TTT | GAT | ATC | GGC | ACC | CTG | AGG | AAT | CCT | GCA | 286 |
|---|---|---|---|---|---|---|---|---|---|---|---|---|---|---|---|---|
| Glu | Glu | Asp | Thr | Gln | Ala | Phe | Asp | Ile | Gly | Thr | Leu | Arg | Asn | Pro | Ala | |
| 80 | | | | | 85 | | | | | 90 | | | | | 95 | |

| GCC | ATT | GAG | GAA | AAA | AAG | CTC | CGG | CGA | GAT | ATT | ATT | CCA | GAA | ACG | TTA | 334 |
|---|---|---|---|---|---|---|---|---|---|---|---|---|---|---|---|---|
| Ala | Ile | Glu | Glu | Lys | Lys | Leu | Arg | Arg | Asp | Ile | Ile | Pro | Glu | Thr | Leu | |
| | | | | 100 | | | | | 105 | | | | | 110 | | |

| TTT | ATT | CCT | CGG | AGG | ACT | CCT | ACA | GCT | CCA | GAT | AAC | ACG | GAC | GTC | CGG | 382 |
|---|---|---|---|---|---|---|---|---|---|---|---|---|---|---|---|---|
| Phe | Ile | Pro | Arg | Arg | Thr | Pro | Thr | Ala | Pro | Asp | Asn | Thr | Asp | Val | Arg | |
| | | | 115 | | | | | 120 | | | | | 125 | | | |

| GAT | TTC | ATT | AAT | GAA | AGG | CTA | AAA | GAG | CAT | GAT | CTT | GAC | CCC | ACC | GCA | 430 |
|---|---|---|---|---|---|---|---|---|---|---|---|---|---|---|---|---|
| Asp | Phe | Ile | Asn | Glu | Arg | Leu | Lys | Glu | His | Asp | Leu | Asp | Pro | Thr | Ala | |
| | | 130 | | | | | 135 | | | | | 140 | | | | |

| CCC | CCC | TAC | GAC | TCA | CTT | GCA | ACC | TAT | GCC | TAT | GAA | GGA | AAT | GAT | TCC | 478 |
|---|---|---|---|---|---|---|---|---|---|---|---|---|---|---|---|---|
| Pro | Pro | Tyr | Asp | Ser | Leu | Ala | Thr | Tyr | Ala | Tyr | Glu | Gly | Asn | Asp | Ser | |
| | 145 | | | | | 150 | | | | | 155 | | | | | |

| ATT | GCT | GAA | TCT | CTG | AGT | TCA | TTA | GAA | TCA | GGT | ACT | ACT | GAA | GGA | GAC | 526 |
|---|---|---|---|---|---|---|---|---|---|---|---|---|---|---|---|---|
| Ile | Ala | Glu | Ser | Leu | Ser | Ser | Leu | Glu | Ser | Gly | Thr | Thr | Glu | Gly | Asp | |
| 160 | | | | | 165 | | | | | 170 | | | | | 175 | |

| CAA | AAC | TAC | GAT | TAC | CTC | CGA | GAA | TGG | GGC | CCT | CGG | TTT | AAT | AAG | CTA | 574 |
|---|---|---|---|---|---|---|---|---|---|---|---|---|---|---|---|---|
| Gln | Asn | Tyr | Asp | Tyr | Leu | Arg | Glu | Trp | Gly | Pro | Arg | Phe | Asn | Lys | Leu | |
| | | | | 180 | | | | | 185 | | | | | 190 | | |

| GCA | GAA | ATG | TAT | GGT | GGT | GGG | GAA | AGT | GAC | AAA | GAC | TCT | TAA | CGT | AGG | 622 |
|---|---|---|---|---|---|---|---|---|---|---|---|---|---|---|---|---|
| Ala | Glu | Met | Tyr | Gly | Gly | Gly | Glu | Ser | Asp | Lys | Asp | Ser | * | Arg | Arg | |
| | | | 195 | | | | | 200 | | | | | 205 | | | |

```
ATA  TAT  GTT  CTG  TTC  AAA  CAA  GAG  AAA  GTA  ACT  CTA  CCC  ATG  CTG  TCT        670
Ile  Tyr  Val  Leu  Phe  Lys  Gln  Glu  Lys  Val  Thr  Leu  Pro  Met  Leu  Ser
          210                 215                      220

CCA  CTT  CAC  AAT  ATT  TGA  TAT  TCA  GGA  GCA  TTT  CCT  GCA  GTC  AGC  ACA        718
Pro  Leu  His  Asn  Ile   *   Tyr  Ser  Gly  Ala  Phe  Pro  Ala  Val  Ser  Thr
          225                      230                      235

ATT  TTT  TTC  TCA                                                                     730
Ile  Phe  Phe  Ser
240
```

( 2 ) INFORMATION FOR SEQ ID NO:56:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Asn  Ser  Ser  Ser  Val  Pro  Gly  Asp  Pro  Leu  Glu  Ser  Thr  Cys  Ser  Ala
 1              5                        10                       15

Glu  Ala  Leu  Leu  Leu  Pro  Ala  Gly  Leu  Ser  Thr  Gly  Ala  Leu  Ile  Ala
          20                       25                       30

Ile  Leu  Leu  Cys  Ile  Ile  Ile  Leu  Val  Ile  Val  Val  Leu  Phe  Ala
          35                  40                       45

Ala  Leu  Lys  Arg  Gln  Arg  Lys  Lys  Glu  Pro  Leu  Ile  Leu  Ser  Lys  Glu
      50                  55                       60

Asp  Ile  Arg  Asp  Asn  Ile  Val  Ser  Tyr  Asn  Asp  Glu  Gly  Gly  Gly  Glu
 65                       70                  75                            80

Glu  Asp  Thr  Gln  Ala  Phe  Asp  Ile  Gly  Thr  Leu  Arg  Asn  Pro  Ala  Ala
                85                       90                       95

Ile  Glu  Glu  Lys  Lys  Leu  Arg  Arg  Asp  Ile  Ile  Pro  Glu  Thr  Leu  Phe
                100                      105                      110

Ile  Pro  Arg  Arg  Thr  Pro  Thr  Ala  Pro  Asp  Asn  Thr  Asp  Val  Arg  Asp
          115                      120                      125

Phe  Ile  Asn  Glu  Arg  Leu  Lys  Glu  His  Asp  Leu  Asp  Pro  Thr  Ala  Pro
     130                      135                      140

Pro  Tyr  Asp  Ser  Leu  Ala  Thr  Tyr  Ala  Tyr  Glu  Gly  Asn  Asp  Ser  Ile
145                           150                 155                      160

Ala  Glu  Ser  Leu  Ser  Ser  Leu  Glu  Ser  Gly  Thr  Thr  Glu  Gly  Asp  Gln
                    165                      170                      175

Asn  Tyr  Asp  Tyr  Leu  Arg  Glu  Trp  Gly  Pro  Arg  Phe  Asn  Lys  Leu  Ala
          180                      185                      190

Glu  Met  Tyr  Gly  Gly  Gly  Glu  Ser  Asp  Lys  Asp  Ser  Arg  Arg  Ile  Tyr
          195                      200                      205

Val  Leu  Phe  Lys  Gln  Glu  Lys  Val  Thr  Leu  Pro  Met  Leu  Ser  Pro  Leu
     210                      215                      220

His  Asn  Ile  Tyr  Ser  Gly  Ala  Phe  Pro  Ala  Val  Ser  Thr  Ile  Phe  Phe
225                      230                      235                      240

Ser
```

( 2 ) INFORMATION FOR SEQ ID NO:57:

( i ) SEQUENCE CHARACTERISTICS:
        ( A ) LENGTH: 2625 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

| | | | | | | |
|---|---|---|---|---|---|---|
| CGGCAGCCCT | GACGTGATGA | GCTCAACCAG | CAGAGACATT | CCATCCCAAG | AGAGGTCTGC | 60 |
| GTGACGCGTC | CGGGAGGCCA | CCCTCAGCAA | GACCACCGTA | CAGTTGGTGG | AAGGGGTGAC | 120 |
| AGCTGCATTC | TCCTGTGCCT | ACCACGTAAC | CAAAAATGAA | GGAGAACTAC | TGTTTACAAG | 180 |
| CCGCCCTGGT | GTGCCTGGGC | ATGCTGTGCC | ACAGCCATGC | CTTTGCCCCA | GAGCGGCGGG | 240 |
| GGCACCTGCG | GCCCTCCTTC | CATGGGCACC | ATGAGAAGGG | CAAGGAGGGG | CAGGTGCTAC | 300 |
| AGCGCTCCAA | GCGTGGCTGG | GTCTGGAACC | AGTTCTTCGT | GATAGAGGAG | TACACCGGGC | 360 |
| CTGACCCCGT | GCTTGTGGGC | AGGCTTCATT | CAGATATTGA | CTCTGGTGAT | GGGAACATTA | 420 |
| AATACATTCT | CTCAGGGGAA | GGAGCTGGAA | CCATTTTGT | GATTGATGAC | AAATCAGGGA | 480 |
| ACATTCATGC | CACCAAGACG | TTGGATCGAG | AAGAGAGAGC | CCAGTACACG | TTGATGGCTC | 540 |
| AGGCGGTGGA | CAGGGACACC | AATCGGCCAC | TGGAGCCACC | GTCGGAATTC | ATTGTCAAGG | 600 |
| TCCAGGACAT | TAATGACAAC | CCTCCGGAGT | TCCTGCACGA | GACCTATCAT | GCCAACGTGC | 660 |
| CTGAGAGGTC | CAATGTGGGA | ACGTCAGTAA | TCCAGGTGAC | AGCTTCAGAT | GCAGATGACC | 720 |
| CCACTTATGG | AAATAGCGCC | AAGTTAGTGT | ACAGTATCCT | CGAAGGACAA | CCCTATTTTT | 780 |
| CGGTGGAAGC | ACAGACAGGT | ATCATCAGAA | CAGCCCTACC | CAACATGGAC | AGGGAGGCCA | 840 |
| AGGAGGAGTA | CCACGTGGTG | ATCCAGGCCA | AGGACATGGG | TGGACATATG | GGCGGACTCT | 900 |
| CAGGGACAAC | CAAAGTGACG | ATCACACTGA | CCGATGTCAA | TGACAACCCA | CCAAAGTTTC | 960 |
| CGCAGAGGCT | ATACCAGATG | TCTGTGTCAG | AAGCAGCCGT | CCCTGGGGAG | GAAGTAGGAA | 1020 |
| GAGTGAAAGC | TAAAGATCCA | GACATTGGAG | AAAATGGCTT | AGTCACATAC | AATATTGTTG | 1080 |
| ATGGAGATGG | TATGGAATCG | TTTGAAATCA | CAACGGACTA | TGAAACACAG | GAGGGGGTGA | 1140 |
| TAAAGCTGAA | AAAGCCTGTA | GATTTTGAAA | CCGAAAGAGC | CTATAGCTTG | AAGGTAGAGG | 1200 |
| CAGCCAACGT | GCACATCGAC | CCGAAGTTTA | TCAGCAATGG | CCCTTTCAAG | GACACTGTGA | 1260 |
| CCGTCAAGAT | CTCAGTAGAA | GATGCTGATG | AGCCCCCTAT | GTTCTTGGCC | CCAAGTTACA | 1320 |
| TCCACGAAGT | CCAAGAAAAT | GCAGCTGCTG | GCACCGTGGT | TGGGAGAGTG | CATGCCAAAG | 1380 |
| ACCCTGATGC | TGCCAACAGC | CCGATAAGGT | ATTCCATCGA | TCGTCACACT | GACCTCGACA | 1440 |
| GATTTTTCAC | TATTAATCCA | GAGGATGGTT | TTATTAAAAC | TACAAAACCT | CTGGATAGAG | 1500 |
| AGGAAACAGC | CTGGCTCAAC | ATCACTGTCT | TTGCAGCAGA | AATCCACAAT | CGGCATCAGG | 1560 |
| AAGCCCAAGT | CCCAGTGGCC | ATTAGGGTCC | TTGATGTCAA | CGATAATGCT | CCCAAGTTTG | 1620 |
| CTGCCCCTTA | TGAAGGTTTC | ATCTGTGAGA | GTGATCAGAC | CAAGCCACTT | TCCAACCAGC | 1680 |
| CAATTGTTAC | AATTAGTGCA | GATGACAAGG | ATGACACGGC | CAATGGACCA | AGATTTATCT | 1740 |
| TCAGCCTACC | CCCTGAAATC | ATTCACAATC | CAAATTTCAC | AGTCAGAGAC | AACCGAGATA | 1800 |
| ACACAGCAGG | CGTGTACGCC | CGGCGTGGAG | GGTTCAGTCG | GCAGAAGCAG | GACTTGTACC | 1860 |
| TTCTGCCCAT | AGTGATCAGC | GATGGCGGCA | TCCCGCCCAT | GAGTAGCACC | AACACCCTCA | 1920 |
| CCATCAAAGT | CTGCGGGTGC | GACGTGAACG | GGCACTGCTC | TCCTGCAAC | GCAGAGGCCT | 1980 |
| ACATTCTGAA | CGCCGGCCTG | AGCACAGGCG | CCCTGATCGC | CATCCTCGCC | TGCATCGTCA | 2040 |
| TTCTCCTGGT | CATTGTAGTA | TTGTTTGTGA | CCCTGAGAAG | GCAAAAGAAA | GAACCACTCA | 2100 |
| TTGTCTTTGA | GGAAGAAGAT | GTCCGTGAGA | ACATCATTAC | TTATGATGAT | GAAGGGGGTG | 2160 |
| GGGAAGAAGA | CACAGAAGCC | TTTGATATTG | CCACCCTCCA | GAATCCTGAT | GGTATCAATG | 2220 |
| GATTTATCCC | CCGCAAAGAC | ATCAAACCTG | AGTATCAGTA | CATGCCTAGA | CCTGGGCTCC | 2280 |

```
GGCCAGCGCC  CAACAGCGTG  GATGTCGATG  ACTTCATCAA  CACGAGAATA  CAGGAGGCAG    2340

ACAATGACCC  CACGGCTCCT  CCTTATGACT  CCATTCAAAT  CTACGGTTAT  GAAGGCAGGG    2400

GCTCAGTGGC  CGGGTCCCTG  AGCTCCCTAG  AGTCGGCCAC  CACAGATTCA  GACTTGGACT    2460

ATGATTATCT  ACAGAACTGG  GGACCTCGTT  TTAAGAAACT  AGCAGATTTG  TATGGTTCCA    2520

AAGACACTTT  TGATGACGAT  TCTTAACAAT  AACGATACAA  ATTTGGCCTT  AAGAACTGTG    2580

TCTGGCGTTC  TCAAGAATCT  AGAAGATGTG  TAACAGGTAT  TTTTT                     2625
```

( 2 ) INFORMATION FOR SEQ ID NO:58:

( i ) SEQUENCE CHARACTERISTICS:
        ( A ) LENGTH: 796 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met  Lys  Glu  Asn  Tyr  Cys  Leu  Gln  Ala  Ala  Leu  Val  Cys  Leu  Gly  Met
  1              5                    10                        15

Leu  Cys  His  Ser  His  Ala  Phe  Ala  Pro  Glu  Arg  Arg  Gly  His  Leu  Arg
              20                    25                        30

Pro  Ser  Phe  His  Gly  His  His  Glu  Lys  Gly  Lys  Glu  Gly  Gln  Val  Leu
              35                    40                        45

Gln  Arg  Ser  Lys  Arg  Gly  Trp  Val  Trp  Asn  Gln  Phe  Phe  Val  Ile  Glu
         50                    55                        60

Glu  Tyr  Thr  Gly  Pro  Asp  Pro  Val  Leu  Val  Gly  Arg  Leu  His  Ser  Asp
 65                        70                    75                        80

Ile  Asp  Ser  Gly  Asp  Gly  Asn  Ile  Lys  Tyr  Ile  Leu  Ser  Gly  Glu  Gly
                       85                    90                        95

Ala  Gly  Thr  Ile  Phe  Val  Ile  Asp  Asp  Lys  Ser  Gly  Asn  Ile  His  Ala
                 100                   105                       110

Thr  Lys  Thr  Leu  Asp  Arg  Glu  Glu  Arg  Ala  Gln  Tyr  Thr  Leu  Met  Ala
              115                   120                       125

Gln  Ala  Val  Asp  Arg  Asp  Thr  Asn  Arg  Pro  Leu  Glu  Pro  Pro  Ser  Glu
 130                       135                   140

Phe  Ile  Val  Lys  Val  Gln  Asp  Ile  Asn  Asp  Asn  Pro  Pro  Glu  Phe  Leu
145                        150                   155                       160

His  Glu  Thr  Tyr  His  Ala  Asn  Val  Pro  Glu  Arg  Ser  Asn  Val  Gly  Thr
                       165                   170                       175

Ser  Val  Ile  Gln  Val  Thr  Ala  Ser  Asp  Ala  Asp  Asp  Pro  Thr  Tyr  Gly
                 180                   185                       190

Asn  Ser  Ala  Lys  Leu  Val  Tyr  Ser  Ile  Leu  Glu  Gly  Gln  Pro  Tyr  Phe
              195                   200                       205

Ser  Val  Glu  Ala  Gln  Thr  Gly  Ile  Ile  Arg  Thr  Ala  Leu  Pro  Asn  Met
 210                       215                   220

Asp  Arg  Glu  Ala  Lys  Glu  Glu  Tyr  His  Val  Val  Ile  Gln  Ala  Lys  Asp
225                        230                   235                       240

Met  Gly  Gly  His  Met  Gly  Gly  Leu  Ser  Gly  Thr  Thr  Lys  Val  Thr  Ile
                       245                   250                       255

Thr  Leu  Thr  Asp  Val  Asn  Asp  Asn  Pro  Pro  Lys  Phe  Pro  Gln  Arg  Leu
                 260                   265                       270

Tyr  Gln  Met  Ser  Val  Ser  Glu  Ala  Ala  Val  Pro  Gly  Glu  Glu  Val  Gly
              275                   280                       285

Arg  Val  Lys  Ala  Lys  Asp  Pro  Asp  Ile  Gly  Glu  Asn  Gly  Leu  Val  Thr
 290                       295                   300
```

```
Tyr  Asn  Ile  Val  Asp  Gly  Asp  Gly  Met  Glu  Ser  Phe  Glu  Ile  Thr  Thr
305            310                 315                      320

Asp  Tyr  Glu  Thr  Gln  Glu  Gly  Val  Ile  Lys  Leu  Lys  Lys  Pro  Val  Asp
                325                      330                      335

Phe  Glu  Thr  Glu  Arg  Ala  Tyr  Ser  Leu  Lys  Val  Glu  Ala  Ala  Asn  Val
                340                 345                 350

His  Ile  Asp  Pro  Lys  Phe  Ile  Ser  Asn  Gly  Pro  Phe  Lys  Asp  Thr  Val
          355                      360                      365

Thr  Val  Lys  Ile  Ser  Val  Glu  Asp  Ala  Asp  Glu  Pro  Pro  Met  Phe  Leu
     370                      375                 380

Ala  Pro  Ser  Tyr  Ile  His  Glu  Val  Gln  Glu  Asn  Ala  Ala  Gly  Thr
385                      390                      395                      400

Val  Val  Gly  Arg  Val  His  Ala  Lys  Asp  Pro  Asp  Ala  Ala  Asn  Ser  Pro
               405                      410                      415

Ile  Arg  Tyr  Ser  Ile  Asp  Arg  His  Thr  Asp  Leu  Asp  Arg  Phe  Phe  Thr
                420                      425                      430

Ile  Asn  Pro  Glu  Asp  Gly  Phe  Ile  Lys  Thr  Thr  Lys  Pro  Leu  Asp  Arg
          435                      440                      445

Glu  Glu  Thr  Ala  Trp  Leu  Asn  Ile  Thr  Val  Phe  Ala  Ala  Glu  Ile  His
     450                      455                      460

Asn  Arg  His  Gln  Glu  Ala  Gln  Val  Pro  Val  Ala  Ile  Arg  Val  Leu  Asp
465                      470                      475                      480

Val  Asn  Asp  Asn  Ala  Pro  Lys  Phe  Ala  Ala  Pro  Tyr  Glu  Gly  Phe  Ile
                    485                      490                      495

Cys  Glu  Ser  Asp  Gln  Thr  Lys  Pro  Leu  Ser  Asn  Gln  Pro  Ile  Val  Thr
               500                      505                      510

Ile  Ser  Ala  Asp  Asp  Lys  Asp  Thr  Ala  Asn  Gly  Pro  Arg  Phe  Ile
          515                      520                      525

Phe  Ser  Leu  Pro  Pro  Glu  Ile  Ile  His  Asn  Pro  Asn  Phe  Thr  Val  Arg
     530                      535                      540

Asp  Asn  Arg  Asp  Asn  Thr  Ala  Gly  Val  Tyr  Ala  Arg  Arg  Gly  Gly  Phe
545                      550                      555                      560

Ser  Arg  Gln  Lys  Gln  Asp  Leu  Tyr  Leu  Leu  Pro  Ile  Val  Ile  Ser  Asp
               565                      570                      575

Gly  Gly  Ile  Pro  Pro  Met  Ser  Ser  Thr  Asn  Thr  Leu  Thr  Ile  Lys  Val
               580                      585                      590

Cys  Gly  Cys  Asp  Val  Asn  Gly  Ala  Leu  Leu  Ser  Cys  Asn  Ala  Glu  Ala
               595                      600                      605

Tyr  Ile  Leu  Asn  Ala  Gly  Leu  Ser  Thr  Gly  Ala  Leu  Ile  Ala  Ile  Leu
610                      615                      620

Ala  Cys  Ile  Val  Ile  Leu  Leu  Val  Ile  Val  Val  Leu  Phe  Val  Thr  Leu
625                      630                      635                      640

Arg  Arg  Gln  Lys  Lys  Glu  Pro  Leu  Ile  Val  Phe  Glu  Glu  Asp  Val
                    645                      650                      655

Arg  Glu  Asn  Ile  Ile  Thr  Tyr  Asp  Asp  Glu  Gly  Gly  Gly  Glu  Glu  Asp
               660                      665                      670

Thr  Glu  Ala  Phe  Asp  Ile  Ala  Thr  Leu  Gln  Asn  Pro  Asp  Gly  Ile  Asn
          675                      680                      685

Gly  Phe  Ile  Pro  Arg  Lys  Asp  Ile  Lys  Pro  Glu  Tyr  Gln  Tyr  Met  Pro
     690                      695                      700

Arg  Pro  Gly  Leu  Arg  Pro  Ala  Pro  Asn  Ser  Val  Asp  Val  Asp  Asp  Phe
705                      710                      715                      720

Ile  Asn  Thr  Arg  Ile  Gln  Glu  Ala  Asp  Asn  Asp  Pro  Thr  Ala  Pro  Pro
```

|     |     |     |     |     |     |     | 725 |     |     |     |     |     | 730 |     |     |     |     |     | 735 |
|-----|-----|-----|-----|-----|-----|-----|-----|-----|-----|-----|-----|-----|-----|-----|-----|-----|-----|-----|-----|

Tyr Asp Ser Ile Gln Ile Tyr Gly Tyr Glu Gly Arg Gly Ser Val Ala
                740                     745                 750

Gly Ser Leu Ser Ser Leu Glu Ser Ala Thr Thr Asp Ser Asp Leu Asp
            755                 760             765

Tyr Asp Tyr Leu Gln Asn Trp Gly Pro Arg Phe Lys Lys Leu Ala Asp
    770                 775                 780

Leu Tyr Gly Ser Lys Asp Thr Phe Asp Asp Asp Ser
785             790                 795

(2) INFORMATION FOR SEQ ID NO:59:

(i) SEQUENCE CHARACTERISTICS:
        (A) LENGTH: 2521 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

| | | | | | |
|---|---|---|---|---|---|
| CGGTGGAGGC | CACAGACACC | TCAAACCTGG | ATTCCACAAT | TCTACGTTAA | GTGTTGGAGT | 60 |
| TTTTATTACT | CTGCTGTAGG | AAAGCCTTTG | CCAATGCTTA | CAAGGAACTG | TTTATCCCTG | 120 |
| CTTCTCTGGG | TTCTGTTTGA | TGGAGGTCTC | CTAACACCAC | TACAACCACA | GCCACAGCAG | 180 |
| ACTTTAGCCA | CAGAGCCAAG | AGAAAATGTT | ATCCATCTGC | CAGGACAACG | GTCACATTTC | 240 |
| CAACGTGTTA | AACGTGGCTG | GGTATGGAAT | CAATTTTTTG | TGCTGGAAGA | ATACGTGGGC | 300 |
| TCCGAGCCTC | AGTATGTGGG | AAAGCTCCAT | TCCGACTTAG | ACAAGGGAGA | GGGCACTGTG | 360 |
| AAATACACCC | TCTCAGGAGA | TGGCGCTGGC | ACCGTTTTTA | CCATTGATGA | AACCACAGGG | 420 |
| GACATTCATG | CAATAAGGAG | CCTAGATAGA | GAAGAGAAAC | CTTTCTACAC | TCTTCGTGCT | 480 |
| CAGGCTGTGG | ACATAGAAAC | CAGAAAGCCC | CTGGAGCCTG | AATCAGAATT | CATCATCAAA | 540 |
| GTGCAGGATA | TTAATGATAA | TGAGCCAAAG | TTTTGGATG | GACCTTATGT | TGCTACTGTT | 600 |
| CCAGAAATGT | CTCCTGTGGG | TGCATATGTA | CTCCAGGTCA | AGGCCACAGA | TGCAGATGAC | 660 |
| CCGACCTATG | GAAACAGTGC | CAGAGTCGTT | TACAGCATTC | TTCAGGGACA | ACCTTATTTC | 720 |
| TCTATTGATC | CAAGACAGG | TGTTATTAGA | ACAGCTTTGC | CAAACATGGA | CAGAGAAGTC | 780 |
| AAAGAACAAT | ATCAAGTACT | CATCCAAGCC | AAGGATATGG | GAGGACAGCT | TGGAGGATTA | 840 |
| GCCGGAACAA | CAATAGTCAA | CATCACTCTC | ACCGATGTCA | ATGACAATCC | ACCTCGATTC | 900 |
| CCCAAAAGCA | TCTTCCACTT | GAAAGTTCCT | GAGTCTTCCC | CTATTGGTTC | AGCTATTGGA | 960 |
| AGAATAAGAG | CTGTGGATCC | TGATTTTGGA | CAAAATGCAG | AAATTGAATA | CAATATTGTT | 1020 |
| CCAGGAGATG | GGGAAATTT | GTTGACATC | GTCACAGATG | AGGATACACA | AGAGGGAGTC | 1080 |
| ATCAAATTGA | AAAAGCCTTT | AGATTTTGAA | ACAAAGAAGG | CATACACTTT | CAAAGTTGAG | 1140 |
| GCTTCCAACC | TTCACCTTGA | CCACCGGTTT | CACTCGGCGG | GCCCTTTCAA | AGACACAGCT | 1200 |
| ACGGTGAAGA | TCAGCGTGCT | GGACGTAGAT | GAGCCACCGG | TTTTCAGCAA | GCCGCTCTAC | 1260 |
| ACCATGGAGG | TTTATGAAGA | CACTCCGGTA | GGGACCATCA | TTGGCGCTGT | CACTGCTCAA | 1320 |
| GACCTGGATG | TAGGCAGCGG | TGCTGTTAGG | TACTTCATAG | ATTGGAAGAG | TGATGGGGAC | 1380 |
| AGCTACTTTA | CAATAGATGG | AAATGAAGGA | ACCATCGCCA | CTAATGAATT | ACTAGACAGA | 1440 |
| GAAAGCACTG | CGCAGTATAA | TTTCTCCATA | ATTGCGAGTA | AAGTTAGTAA | CCCTTTATTG | 1500 |
| ACCAGCAAAG | TCAATATACT | GATTAATGTC | TTAGATGTAA | ATGAATTTCC | TCCAGAAATA | 1560 |
| TCTGTGCCAT | ATGAGACAGC | CGTGTGTGAA | AATGCCAAGC | CAGGACAGAT | AATTCAGATA | 1620 |

```
GTCAGTGCTG CAGACCGAGA TCTTTCACCT GCTGGGCAAC AATTCTCCTT TAGATTATCA    1680
CCTGAGGCTG CTATCAAACC AAATTTTACA GTTCGTGACT TCAGAAACAA CACAGCGGGG    1740
ATTGAAACCC GAAGAAATGG ATACAGCCGC AGGCAGCAAG AGTTGTATTT CCTCCCTGTT    1800
GTAATAGAAG ACAGCAGCTA CCCTGTCCAG AGCAGCACAA ACACAATGAC TATTCGAGTC    1860
TGTAGATGTG ACTCTGATGG CACCATCCTG TCTTGTAATG TGGAAGCAAT TTTTCTACCT    1920
GTAGGACTTA GCACTGGGGC GTTGATTGCA ATTCTACTAT GCATTGTTAT ACTCTTAGCC    1980
ATAGTTGTAC TGTATGTAGC ACTGCGAAGG CAGAAGAAAA AGCACACCCT GATGACCTCT    2040
AAAGAAGACA TCAGAGACAA CGTCATCCAT TACGATGATG AAGGAGGTGG GGAGGAAGAT    2100
ACCCAGGCTT TCGACATCGG GGCTCTGAGA AACCCAAAAG TGATTGAGGA GAACAAAATT    2160
CGCAGGGATA TAAAACCAGA CTCTCTCTGT TTACCTCGTC AGAGACCACC CATGGAAGAT    2220
AACACAGACA TAAGGGATTT CATTCATCAA AGGCTACAGG AAAATGATGT AGATCCAACT    2280
GCCCCACCAA TCGATTCACT GGCCACATAT GCCTACGAAG GGAGTGGGTC CGTGGCAGAG    2340
TCCCTCAGCT CTATAGACTC TCTCACCACA GAAGCCGACC AGGACTATGA CTATCTGACA    2400
GACTGGGGAC CCCGCTTTAA AGTCTTGGCA GACATGTTTG GCGAAGAAGA GAGTTATAAC    2460
CCTGATAAAG TCACTTAAGG GAGTCGTGGA GGCTAAAATA CAACCGAGAG GGAGATTTT    2520
T                                                                   2521
```

( 2 ) INFORMATION FOR SEQ ID NO:60:

( i ) SEQUENCE CHARACTERISTICS:
        ( A ) LENGTH: 794 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Met Leu Thr Arg Asn Cys Leu Ser Leu Leu Leu Trp Val Leu Phe Asp
 1               5                  10                  15

Gly Gly Leu Leu Thr Pro Leu Gln Pro Gln Pro Gln Gln Thr Leu Ala
             20                  25                  30

Thr Glu Pro Arg Glu Asn Val Ile His Leu Pro Gly Gln Arg Ser His
         35                  40                  45

Phe Gln Arg Val Lys Arg Gly Trp Val Trp Asn Gln Phe Phe Val Leu
     50                  55                  60

Glu Glu Tyr Val Gly Ser Glu Pro Gln Tyr Val Gly Lys Leu His Ser
65                  70                  75                  80

Asp Leu Asp Lys Gly Glu Gly Thr Val Lys Tyr Thr Leu Ser Gly Asp
                85                  90                  95

Gly Ala Gly Thr Val Phe Thr Ile Asp Glu Thr Thr Gly Asp Ile His
            100                 105                 110

Ala Ile Arg Ser Leu Asp Arg Glu Glu Lys Pro Phe Tyr Thr Leu Arg
        115                 120                 125

Ala Gln Ala Val Asp Ile Glu Thr Arg Lys Pro Leu Glu Pro Glu Ser
    130                 135                 140

Glu Phe Ile Ile Lys Val Gln Asp Ile Asn Asp Asn Glu Pro Lys Phe
145                 150                 155                 160

Leu Asp Gly Pro Tyr Val Ala Thr Val Pro Glu Met Ser Pro Val Gly
                165                 170                 175

Ala Tyr Val Leu Gln Val Lys Ala Thr Asp Ala Asp Asp Pro Thr Tyr
            180                 185                 190
```

```
Gly  Asn  Ser  Ala  Arg  Val  Val  Tyr  Ser  Ile  Leu  Gln  Gly  Gln  Pro  Tyr
          195                      200                    205

Phe  Ser  Ile  Asp  Pro  Lys  Thr  Gly  Val  Ile  Arg  Thr  Ala  Leu  Pro  Asn
     210                      215                    220

Met  Asp  Arg  Glu  Val  Lys  Glu  Gln  Tyr  Gln  Val  Leu  Ile  Gln  Ala  Lys
225                           230                    235                      240

Asp  Met  Gly  Gly  Gln  Leu  Gly  Gly  Leu  Ala  Gly  Thr  Thr  Ile  Val  Asn
               245                      250                              255

Ile  Thr  Leu  Thr  Asp  Val  Asn  Asp  Asn  Pro  Pro  Arg  Phe  Pro  Lys  Ser
               260                      265                    270

Ile  Phe  His  Leu  Lys  Val  Pro  Glu  Ser  Ser  Pro  Ile  Gly  Ser  Gly  Ile
          275                      280                    285

Gly  Arg  Ile  Arg  Ala  Val  Asp  Pro  Asp  Phe  Gly  Gln  Asn  Ala  Glu  Ile
290                           295                    300

Glu  Tyr  Asn  Ile  Val  Pro  Gly  Asp  Gly  Gly  Asn  Leu  Phe  Asp  Ile  Val
305                      310                    315                      320

Thr  Asp  Glu  Asp  Thr  Gln  Glu  Gly  Val  Ile  Lys  Leu  Lys  Lys  Pro  Leu
               325                      330                    335

Asp  Phe  Glu  Thr  Lys  Lys  Ala  Tyr  Thr  Phe  Lys  Val  Glu  Ala  Ser  Asn
               340                      345                    350

Leu  His  Leu  Asp  His  Arg  Phe  His  Ser  Ala  Gly  Pro  Phe  Lys  Asp  Thr
          355                      360                    365

Ala  Thr  Val  Lys  Ile  Ser  Val  Leu  Asp  Val  Asp  Glu  Pro  Pro  Val  Phe
370                           375                    380

Ser  Lys  Pro  Leu  Tyr  Thr  Met  Glu  Val  Tyr  Glu  Asp  Thr  Pro  Val  Gly
385                      390                    395                      400

Thr  Ile  Ile  Gly  Ala  Val  Thr  Ala  Gln  Asp  Leu  Asp  Val  Gly  Ser  Gly
               405                      410                    415

Ala  Val  Arg  Tyr  Phe  Ile  Asp  Trp  Lys  Ser  Asp  Gly  Asp  Ser  Tyr  Phe
               420                      425                    430

Thr  Ile  Asp  Gly  Asn  Glu  Gly  Thr  Ile  Ala  Thr  Asn  Glu  Leu  Leu  Asp
               435                      440                    445

Arg  Glu  Ser  Thr  Ala  Gln  Tyr  Asn  Phe  Ser  Ile  Ile  Ala  Ser  Lys  Val
450                           455                    460

Ser  Asn  Pro  Leu  Leu  Thr  Ser  Lys  Val  Asn  Ile  Leu  Ile  Asn  Val  Leu
465                      470                    475                      480

Asp  Val  Asn  Glu  Phe  Pro  Pro  Glu  Ile  Ser  Val  Pro  Tyr  Glu  Thr  Ala
               485                      490                    495

Val  Cys  Glu  Asn  Ala  Lys  Pro  Gly  Gln  Ile  Ile  Gln  Ile  Val  Ser  Ala
               500                      505                    510

Ala  Asp  Arg  Asp  Leu  Ser  Pro  Ala  Gly  Gln  Gln  Phe  Ser  Phe  Arg  Leu
               515                      520                    525

Ser  Pro  Glu  Ala  Ala  Ile  Lys  Pro  Asn  Phe  Thr  Val  Arg  Asp  Phe  Arg
     530                      535                    540

Asn  Asn  Thr  Ala  Gly  Ile  Glu  Thr  Arg  Arg  Asn  Gly  Tyr  Ser  Arg  Arg
545                      550                    555                      560

Gln  Gln  Glu  Leu  Tyr  Phe  Leu  Pro  Val  Val  Ile  Glu  Asp  Ser  Ser  Tyr
               565                      570                    575

Pro  Val  Gln  Ser  Ser  Thr  Asn  Thr  Met  Thr  Ile  Arg  Val  Cys  Arg  Cys
               580                      585                    590

Asp  Ser  Asp  Gly  Thr  Ile  Leu  Ser  Cys  Asn  Val  Glu  Ala  Ile  Phe  Leu
          595                      600                    605

Pro  Val  Gly  Leu  Ser  Thr  Gly  Ala  Leu  Ile  Ala  Ile  Leu  Leu  Cys  Ile
```

|      |      |      |      | 610  |      |      |      | 615  |      |      |      | 620  |      |      |      |
|------|------|------|------|------|------|------|------|------|------|------|------|------|------|------|------|
| Val  | Ile  | Leu  | Leu  | Ala  | Ile  | Val  | Val  | Leu  | Tyr  | Val  | Ala  | Leu  | Arg  | Arg  | Gln  |
| 625  |      |      |      | 630  |      |      |      | 635  |      |      |      |      |      |      | 640  |
| Lys  | Lys  | Lys  | His  | Thr  | Leu  | Met  | Thr  | Ser  | Lys  | Glu  | Asp  | Ile  | Arg  | Asp  | Asn  |
|      |      |      |      | 645  |      |      |      | 650  |      |      |      |      |      | 655  |      |
| Val  | Ile  | His  | Tyr  | Asp  | Asp  | Glu  | Gly  | Gly  | Gly  | Glu  | Glu  | Asp  | Thr  | Gln  | Ala  |
|      |      |      | 660  |      |      |      |      | 665  |      |      |      |      | 670  |      |      |
| Phe  | Asp  | Ile  | Gly  | Ala  | Leu  | Arg  | Asn  | Pro  | Lys  | Val  | Ile  | Glu  | Glu  | Asn  | Lys  |
|      |      | 675  |      |      |      |      | 680  |      |      |      |      | 685  |      |      |      |
| Ile  | Arg  | Arg  | Asp  | Ile  | Lys  | Pro  | Asp  | Ser  | Leu  | Cys  | Leu  | Pro  | Arg  | Gln  | Arg  |
|      | 690  |      |      |      |      | 695  |      |      |      |      | 700  |      |      |      |      |
| Pro  | Pro  | Met  | Glu  | Asp  | Asn  | Thr  | Asp  | Ile  | Arg  | Asp  | Phe  | Ile  | His  | Gln  | Arg  |
| 705  |      |      |      |      | 710  |      |      |      |      | 715  |      |      |      |      | 720  |
| Leu  | Gln  | Glu  | Asn  | Asp  | Val  | Asp  | Pro  | Thr  | Ala  | Pro  | Pro  | Ile  | Asp  | Ser  | Leu  |
|      |      |      |      | 725  |      |      |      |      | 730  |      |      |      |      | 735  |      |
| Ala  | Thr  | Tyr  | Ala  | Tyr  | Glu  | Gly  | Ser  | Gly  | Ser  | Val  | Ala  | Glu  | Ser  | Leu  | Ser  |
|      |      |      | 740  |      |      |      |      | 745  |      |      |      |      | 750  |      |      |
| Ser  | Ile  | Asp  | Ser  | Leu  | Thr  | Thr  | Glu  | Ala  | Asp  | Gln  | Asp  | Tyr  | Asp  | Tyr  | Leu  |
|      |      | 755  |      |      |      |      | 760  |      |      |      |      | 765  |      |      |      |
| Thr  | Asp  | Trp  | Gly  | Pro  | Arg  | Phe  | Lys  | Val  | Val  | Ala  | Asp  | Met  | Phe  | Gly  | Glu  |
|      | 770  |      |      |      |      | 775  |      |      |      |      | 780  |      |      |      |      |
| Glu  | Glu  | Ser  | Tyr  | Asn  | Pro  | Asp  | Lys  | Val  | Thr  |      |      |      |      |      |      |
| 785  |      |      |      |      | 790  |      |      |      |      |      |      |      |      |      |      |

( 2 ) INFORMATION FOR SEQ ID NO:61:

( i ) SEQUENCE CHARACTERISTICS:
        ( A ) LENGTH: 2690 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

| | | | | | |
|---|---|---|---|---|---|
| CTTCAAGGTT | TTGCTGACTC | AGTCTGGTAG | TCAGAGTCTG | CAGGAGAAGA | CAGTTCAAGG | 60 |
| CAGGGCCTGG | AGGATTGGAT | CAGTTTAGGG | ACAGGTCAAA | GGCTGGCTTA | GAGACCTTAG | 120 |
| AGGCAGGTTG | CTTGGGTCGT | TGAATGCTAG | TCTGGTCCTG | AGAGCCCTTT | TCTCTGGCAA | 180 |
| CTGTGGACTC | AGAGCTAACC | AATTGTAGTT | GGCAGTGGGG | GTGAAGGGTG | ATCCAGAGGC | 240 |
| CTGAGCTGCA | GAGGGCACAA | GAGAGAAAAG | ATGTCTTAGA | AAGAGCTTTG | AGAACATGCC | 300 |
| TTGGCTGCTG | GCAGGGACCT | TGGATGGGGT | AGTCTACACC | CGGAAGTGCC | TGCCTGCCAT | 360 |
| CCTCTAGTGG | CTGCCTTGCA | AAATATGCTC | AGTGCAGCCG | CGTGCATGAA | TGAAAACGCC | 420 |
| GCCGGGCGCT | TCTAGTCGGA | CAAAATGCAG | CCGAGAACTC | CGCTCGTTCT | GTGCGTTCTC | 480 |
| CTGTCCCAGG | TGCTGCTGCT | AACATCTGCA | GAAGATTTGG | ACTGCACTCC | TGGATTTCAG | 540 |
| CAGAAAGTGT | TCCATATCAA | TCAGCCAGCT | GAATTCATTG | AGGACCAGTC | AATTCTAAAC | 600 |
| TTGACCTTCA | GTGACTGTAA | GGGAAACGAC | AAGCTACGCT | ATGAGGTCTC | GAGCCCATAC | 660 |
| TTCAAGGTGA | ACAGCGATGG | CGGCTTAGTT | GCTCTGAGAA | ACATAACTGC | AGTGGGCAAA | 720 |
| ACTCTGTTCG | TCCATGCACG | GACCCCCCAT | GCGGAAGATA | TGGCAGAACT | CGTGATTGTC | 780 |
| GGGGGGAAAG | ACATCCAGGG | CTCCTTGCAG | GATATATTTA | AATTTGCAAG | AACTTCTCCT | 840 |
| GTCCCAAGAC | AAAAGAGGTC | CATTGTGGTA | TCTCCCATTT | TAATTCCAGA | GAATCAGAGA | 900 |
| CAGCCTTTCC | CAAGAGATGT | TGGCAAGGTA | GTCGATAGTG | ACAGGCCAGA | AAGGTCCAAG | 960 |

| | | | | |
|---|---|---|---|---|
| TTCCGGCTCA | CTGGAAAGGG | AGTGGATCAA | GAGCCTAAAG | GAATTTTCAG AATCAATGAG | 1020 |
| AACACAGGGA | GCGTCTCCGT | GACACGGACC | TTGGACAGAG | AAGTAATCGC TGTTTATCAA | 1080 |
| CTATTTGTGG | AGACCACTGA | TGTCAATGGC | AAAACTCTCG | AGGGGCCGGT GCCTCTGGAA | 1140 |
| GTCATTGTGA | TTGATCAGAA | TGACAACCGA | CCGATCTTTC | GGGAAGGCCC CTACATCGGC | 1200 |
| CACGTCATGG | AAGGGTCACC | CACAGGCACC | ACAGTGATGC | GGATGACAGC CTTTGATGCA | 1260 |
| GATGACCCAG | CCACCGATAA | TGCCCTCCTG | CGGTATAATA | TCCGTCAACA GACGCCTGAC | 1320 |
| AAGCCATCTC | CCAACATGTT | CTACATCGAT | CCTGAGAAAG | GAGACATTGT CACTGTTGTG | 1380 |
| TCACCTGCGC | TGCTGGACCG | AGAGACTCTG | GAAAATCCCA | AGTATGAACT GATCATCGAG | 1440 |
| GCTCAAGATA | TGGCTGGACT | GGATGTTGGA | TTAACAGGCA | CGGCCACAGC CACGATCATG | 1500 |
| ATCGATGACA | AAAATGATCA | CTCACCAAAA | TTCACCAAGA | AAGAGTTTCA AGCCACAGTC | 1560 |
| GAGGAAGGAG | CTGTGGGAGT | TATTGTCAAT | TTGACAGTTG | AAGATAAGGA TGACCCCACC | 1620 |
| ACAGGTGCAT | GGAGGGCTGC | CTACACCATC | ATCAACGGAA | ACCCCGGGCA GAGCTTTGAA | 1680 |
| ATCCACACCA | ACCCTCAAAC | CAACGAAGGG | ATGCTTTCTG | TTGTCAAACC ATTGGACTAT | 1740 |
| GAAATTTCTG | CCTTCCACAC | CCTGCTGATC | AAAGTGGAAA | ATGAAGACCC ACTCGTACCC | 1800 |
| GACGTCTCCT | ACGGCCCCAG | CTCCACAGCC | ACCGTCCACA | TCACTGTCCT GGATGTCAAC | 1860 |
| GAGGGCCCAG | TCTTCTACCC | AGACCCCATG | ATGGTGACCA | GGCAGGAGGA CCTCTCTGTG | 1920 |
| GGCAGCGTGC | TGCTGACAGT | GAATGCCACG | GACCCCGACT | CCCTGCAGCA TCAAACCATC | 1980 |
| AGGTATTCTG | TTTACAAGGA | CCCAGCAGGT | TGGCTGAATA | TTAACCCCAT CAATGGGACT | 2040 |
| GTTGACACCA | CAGCTGTGCT | GGACCGTGAG | TCCCCATTTG | TCGACAACAG CGTGTACACT | 2100 |
| GCTCTCTTCC | TGGCAATTGA | CAGTGGCAAC | CCTCCCGCTA | CGGGCACTGG GACTTTGCTG | 2160 |
| ATAACCCTGG | AGGACGTGAA | TGACAATGCC | CCGTTCATTT | ACCCCACAGT AGCTGAAGTC | 2220 |
| TGTGATGATG | CCAAAAACCT | CAGTGTAGTC | ATTTTGGGAG | CATCAGATAA GGATCTTCAC | 2280 |
| CCGAATACAG | ATCCTTTCAA | ATTTGAAATC | CACAAACAAG | CTGTTCCTGA TAAAGTCTGG | 2340 |
| AAGATCTCCA | AGATCAACAA | TACACACGCC | CTGGTAAGCC | TTCTTCAAAA TCTGAACAAA | 2400 |
| GCAAACTACA | ACCTGCCCAT | CATGGTGACA | GATTCAGGGA | ACCACCCAT GACGAATATC | 2460 |
| ACAGATCTCA | GGGTACAAGT | GTGCTCCTGC | AGGAATTCCA | AAGTGGACTG CAACGCGGCG | 2520 |
| GGGGCCCTGC | GCTTCAGCCT | GCCCTCAGTC | CTGCTCCTCA | GCCTCTTCAG CTTAGCTTGT | 2580 |
| CTGTGAGAAC | TCCTGACGTC | TGAAGCTTGA | CTCCCAAGTT | TCCATAGCAA CAGGAAAAAA | 2640 |
| AAAAAATCTA | TCCAAATCTG | AAGATTGCGG | TTTACAGCTA | TCGAACTTCG | 2690 |

( 2 ) INFORMATION FOR SEQ ID NO:62:

( i ) SEQUENCE CHARACTERISTICS:
        ( A ) LENGTH: 713 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

```
Met Gln Pro Arg Thr Pro Leu Val Leu Cys Val Leu Leu Ser Gln Val
1               5                   10                  15

Leu Leu Leu Thr Ser Ala Glu Asp Leu Asp Cys Thr Pro Gly Phe Gln
            20                  25                  30

Gln Lys Val Phe His Ile Asn Gln Pro Ala Glu Phe Ile Glu Asp Gln
            35                  40                  45

Ser Ile Leu Asn Leu Thr Phe Ser Asp Cys Lys Gly Asn Asp Lys Leu
```

|     |     |     |     | 50  |     |     |     |     | 55  |     |     |     |     | 60  |     |     |     |     |     |
|---|---|---|---|---|---|---|---|---|---|---|---|---|---|---|---|---|---|---|---|
| Arg 65 | Tyr | Glu | Val | Ser | Ser 70 | Pro | Tyr | Phe | Lys | Val 75 | Asn | Ser | Asp | Gly | Gly 80 |
| Leu | Val | Ala | Leu | Arg 85 | Asn | Ile | Thr | Ala | Val 90 | Gly | Lys | Thr | Leu | Phe 95 | Val |
| His | Ala | Arg | Thr 100 | Pro | His | Ala | Glu | Asp 105 | Met | Ala | Glu | Leu | Val 110 | Ile | Val |
| Gly | Gly | Lys 115 | Asp | Ile | Gln | Gly | Ser 120 | Leu | Gln | Asp | Ile | Phe 125 | Lys | Phe | Ala |
| Arg | Thr 130 | Ser | Pro | Val | Pro | Arg 135 | Gln | Lys | Arg | Ser | Ile 140 | Val | Val | Ser | Pro |
| Ile 145 | Leu | Ile | Pro | Glu | Asn 150 | Gln | Arg | Gln | Pro | Phe 155 | Pro | Arg | Asp | Val | Gly 160 |
| Lys | Val | Val | Asp | Ser 165 | Asp | Arg | Pro | Glu | Arg 170 | Ser | Lys | Phe | Arg | Leu 175 | Thr |
| Gly | Lys | Gly | Val 180 | Asp | Gln | Glu | Pro | Lys 185 | Gly | Ile | Phe | Arg | Ile 190 | Asn | Glu |
| Asn | Thr | Gly 195 | Ser | Val | Ser | Val | Thr 200 | Arg | Thr | Leu | Asp | Arg 205 | Glu | Val | Ile |
| Ala | Val 210 | Tyr | Gln | Leu | Phe | Val 215 | Glu | Thr | Thr | Asp | Val 220 | Asn | Gly | Lys | Thr |
| Leu 225 | Glu | Gly | Pro | Val | Pro 230 | Leu | Glu | Val | Ile | Val 235 | Ile | Asp | Gln | Asn | Asp 240 |
| Asn | Arg | Pro | Ile | Phe 245 | Arg | Glu | Gly | Pro | Tyr 250 | Ile | Gly | His | Val | Met 255 | Glu |
| Gly | Ser | Pro | Thr 260 | Gly | Thr | Thr | Val | Met 265 | Arg | Met | Thr | Ala | Phe 270 | Asp | Ala |
| Asp | Asp | Pro 275 | Ala | Thr | Asp | Asn | Ala 280 | Leu | Leu | Arg | Tyr | Asn 285 | Ile | Arg | Gln |
| Gln | Thr 290 | Pro | Asp | Lys | Pro | Ser 295 | Pro | Asn | Met | Phe | Tyr 300 | Ile | Asp | Pro | Glu |
| Lys 305 | Gly | Asp | Ile | Val | Thr 310 | Val | Val | Ser | Pro | Ala 315 | Leu | Leu | Asp | Arg | Glu 320 |
| Thr | Leu | Glu | Asn | Pro 325 | Lys | Tyr | Glu | Leu | Ile 330 | Ile | Glu | Ala | Gln | Asp 335 | Met |
| Ala | Gly | Leu | Asp 340 | Val | Gly | Leu | Thr | Gly 345 | Thr | Ala | Thr | Ala | Thr 350 | Ile | Met |
| Ile | Asp | Asp 355 | Lys | Asn | Asp | His | Ser 360 | Pro | Lys | Phe | Thr | Lys 365 | Lys | Glu | Phe |
| Gln | Ala 370 | Thr | Val | Glu | Glu | Gly 375 | Ala | Val | Gly | Val | Ile 380 | Val | Asn | Leu | Thr |
| Val 385 | Glu | Asp | Lys | Asp | Asp 390 | Pro | Thr | Thr | Gly | Ala 395 | Trp | Arg | Ala | Ala | Tyr 400 |
| Thr | Ile | Ile | Asn | Gly 405 | Asn | Pro | Gly | Gln | Ser 410 | Phe | Glu | Ile | His | Thr 415 | Asn |
| Pro | Gln | Thr | Asn 420 | Glu | Gly | Met | Leu | Ser 425 | Val | Val | Lys | Pro | Leu 430 | Asp | Tyr |
| Glu | Ile | Ser 435 | Ala | Phe | His | Thr | Leu 440 | Leu | Ile | Lys | Val | Glu 445 | Asn | Glu | Asp |
| Pro | Leu 450 | Val | Pro | Asp | Val | Ser 455 | Tyr | Gly | Pro | Ser | Ser 460 | Thr | Ala | Thr | Val |
| His 465 | Ile | Thr | Val | Leu | Asp 470 | Val | Asn | Glu | Gly | Pro 475 | Val | Phe | Tyr | Pro | Asp 480 |

|     |     |     |     |     |     |     |     |     |     |     |     |     |     |
|-----|-----|-----|-----|-----|-----|-----|-----|-----|-----|-----|-----|-----|-----|
| Pro | Met | Met | Val | Thr<br>485 | Arg | Gln | Glu | Asp | Leu<br>490 | Ser | Val | Gly | Ser | Val<br>495 | Leu |
| Leu | Thr | Val | Asn<br>500 | Ala | Thr | Asp | Pro | Asp<br>505 | Ser | Leu | Gln | His | Gln<br>510 | Thr | Ile |
| Arg | Tyr | Ser<br>515 | Val | Tyr | Lys | Asp | Pro<br>520 | Ala | Gly | Trp | Leu | Asn<br>525 | Ile | Asn | Pro |
| Ile | Asn<br>530 | Gly | Thr | Val | Asp | Thr<br>535 | Thr | Ala | Val | Leu | Asp<br>540 | Arg | Glu | Ser | Pro |
| Phe<br>545 | Val | Asp | Asn | Ser | Val<br>550 | Tyr | Thr | Ala | Leu | Phe<br>555 | Leu | Ala | Ile | Asp | Ser<br>560 |
| Gly | Asn | Pro | Pro | Ala<br>565 | Thr | Gly | Thr | Gly | Thr<br>570 | Leu | Leu | Ile | Thr | Leu<br>575 | Glu |
| Asp | Val | Asn | Asp<br>580 | Asn | Ala | Pro | Phe | Ile<br>585 | Tyr | Pro | Thr | Val | Ala<br>590 | Glu | Val |
| Cys | Asp | Asp<br>595 | Ala | Lys | Asn | Leu | Ser<br>600 | Val | Val | Ile | Leu | Gly<br>605 | Ala | Ser | Asp |
| Lys | Asp<br>610 | Leu | His | Pro | Asn | Thr<br>615 | Asp | Pro | Phe | Lys | Phe<br>620 | Glu | Ile | His | Lys |
| Gln<br>625 | Ala | Val | Pro | Asp | Lys<br>630 | Val | Trp | Lys | Ile | Ser<br>635 | Lys | Ile | Asn | Asn | Thr<br>640 |
| His | Ala | Leu | Val | Ser<br>645 | Leu | Leu | Gln | Asn | Leu<br>650 | Asn | Lys | Ala | Asn | Tyr<br>655 | Asn |
| Leu | Pro | Ile | Met<br>660 | Val | Thr | Asp | Ser | Gly<br>665 | Lys | Pro | Pro | Met<br>670 | Thr | Asn | Ile |
| Thr | Asp | Leu<br>675 | Arg | Val | Gln | Val | Cys<br>680 | Ser | Cys | Arg | Asn | Ser<br>685 | Lys | Val | Asp |
| Cys | Asn<br>690 | Ala | Ala | Gly | Ala | Leu<br>695 | Arg | Phe | Ser | Leu | Pro<br>700 | Ser | Val | Ile | Leu |
| Leu<br>705 | Ser | Leu | Phe | Ser | Leu<br>710 | Ala | Cys | Leu |     |     |     |     |     |     |     |

What is claimed is:

1. A purified and isolated full length human cadherin polypeptide selected from the group consisting of the cadherin-5 polypeptide of SEQ ID NO: 50, the cadherin-8 polypeptide of SEQ ID NO: 54, the cadherin-11 polypeptide of SEQ ID NO: 58, the cadherin-12 polypeptide of SEQ ID NO: 60, and the cadherin-13 polypeptide of SEQ ID NO: 62.

2. A purified and isolated rat cadherin-8 polypeptide selected from the group consisting of the cadherin of SEQ ID NO: 42 and the cadherin of SEQ ID NO: 44.

3. A purified and isolated rat cadherin polypeptide selected from the group consisting of, the cadherin-5 of SEQ ID NO: 12 or SEQ ID NO: 30, the cadherin-11 of SEQ ID NO: 24 or SEQ ID NO: 40, and the cadherin-13 of SEQ ID NO: 26.

* * * * *

UNITED STATES PATENT AND TRADEMARK OFFICE
CERTIFICATE OF CORRECTION

PATENT NO. : 5,646,250
DATED : July 8, 1997
INVENTOR(S) : Shintaro Suzuki

It is certified that error appears in the above-identified patent and that said Letters Patent is hereby corrected as shown below:

Column 1, line 48 replace "eatenins" with --catenins--;

Column 6, line 27 replace "international" with --International--;

Column 9, line 60 delete "The";

Column 9, line 62 replace "cells" with --L-cells--;

Column 11, line 11 replace "CMF-PBS PBS" with --CMF-PBS--;

Column 15, line 42 replace "used" with --used to--;

Column 17, line 38 replace " Crissue Tek " with --(Tissue Tek)--;

SEQ ID NO: 41, nucleotide 1118 replace "G" with --C--.

Signed and Sealed this

Eighth Day of February, 2000

Attest:

Q. TODD DICKINSON

Attesting Officer

Commissioner of Patents and Trademarks